United States Patent
Browne et al.

(10) Patent No.: US 8,562,615 B2
(45) Date of Patent: Oct. 22, 2013

(54) APPARATUS FOR INTRODUCING PORTALS IN BONE HAVING TRANSVERSELY MOVABLE BONE PROBE

(71) Applicant: Pyng Medical Corp., Richmond (CA)

(72) Inventors: Gregory Vincent Browne, Victoria (CA); Werner Reinhard Simbeck, Victoria (CA); Christopher Grant Denny, Victoria (CA); David Brian Bonar, Delta (CA); Terence Gilhuly, Vancouver (CA)

(73) Assignee: Pyng Medical Corp., Richmond (CA)

( * ) Notice: Subject to any disclaimer, the term of this patent is extended or adjusted under 35 U.S.C. 154(b) by 0 days.

(21) Appl. No.: 13/757,569

(22) Filed: Feb. 1, 2013

(65) Prior Publication Data

US 2013/0158484 A1    Jun. 20, 2013

Related U.S. Application Data

(63) Continuation of application No. 12/851,546, filed on Aug. 5, 2010, now Pat. No. 8,388,623, which is a continuation of application No. 12/745,557, filed as application No. PCT/CA2008/002146 on Dec. 5, 2008, now Pat. No. 8,333,769.

(60) Provisional application No. 61/012,372, filed on Dec. 7, 2007, provisional application No. 61/104,684, filed on Oct. 10, 2008.

(51) Int. Cl.
*A61F 2/46* (2006.01)
*A61B 17/34* (2006.01)

(52) U.S. Cl.
USPC ........................................ 606/86 R; 606/186

(58) Field of Classification Search
USPC ......... 606/79, 80, 84–87, 108, 167, 172, 179, 606/181–186; 604/117, 158–170.03, 181, 604/187; 83/699.1; 30/321, 363; 144/360, 144/367, 1.1, 2.1, 3.1
See application file for complete search history.

(56) References Cited

U.S. PATENT DOCUMENTS

| | | | | |
|---|---|---|---|---|
| 3,815,605 A | * | 6/1974 | Schmidt et al. | 606/182 |
| 4,403,989 A | * | 9/1983 | Christensen et al. | 604/137 |
| 4,530,695 A | * | 7/1985 | Phillips et al. | 604/184 |
| 4,676,781 A | * | 6/1987 | Phillips et al. | 604/135 |
| 5,116,324 A | * | 5/1992 | Brierley et al. | 604/180 |
| 5,817,052 A | * | 10/1998 | Johnson et al. | 604/506 |
| 5,868,711 A | * | 2/1999 | Kramer et al. | 604/136 |
| 5,960,797 A | * | 10/1999 | Kramer et al. | 128/899 |
| 6,102,887 A | * | 8/2000 | Altman | 604/22 |
| 6,346,099 B1 | * | 2/2002 | Altman | 604/528 |
| 6,761,726 B1 | * | 7/2004 | Findlay et al. | 606/182 |

(Continued)

*Primary Examiner* — Todd Manahan
*Assistant Examiner* — Eric S Gibson
(74) *Attorney, Agent, or Firm* — Oyen Wiggs Green & Mutala LLP

(57) ABSTRACT

An apparatus for introducing a bone portal into a bone is described herein. An example apparatus for introducing portals into bone includes a stylet and a handle. The stylet is configured to support an infusion tube assembly. The infusion tube assembly comprises a bone portal. The handle is drivingly coupled to the stylet by a release mechanism. The release mechanism comprises a bone probe that, in a first configuration, extends generally parallel to the stylet. The release mechanism is operative to uncouple the driving coupling between the handle and the stylet upon axial motion of the bone probe relative to the handle. The stylet and bone probe are movable apart from one another to a second configuration.

20 Claims, 47 Drawing Sheets

(56) References Cited

U.S. PATENT DOCUMENTS

| | | | |
|---|---|---|---|
| 7,347,840 B2 * | 3/2008 | Findlay et al. | 604/187 |
| 7,879,057 B2 * | 2/2011 | Sakata et al. | 606/182 |
| 8,142,365 B2 * | 3/2012 | Miller | 600/566 |
| 8,333,769 B2 * | 12/2012 | Browne et al. | 606/86 R |
| 8,388,623 B2 * | 3/2013 | Browne et al. | 606/86 R |
| 2003/0229308 A1 * | 12/2003 | Tsals et al. | 604/116 |
| 2005/0131345 A1 * | 6/2005 | Miller | 604/117 |
| 2005/0148940 A1 * | 7/2005 | Miller | 604/187 |
| 2009/0124931 A1 * | 5/2009 | Sakata et al. | 600/583 |
| 2010/0298830 A1 * | 11/2010 | Browne et al. | 606/79 |
| 2010/0312246 A1 * | 12/2010 | Browne et al. | 606/87 |

* cited by examiner

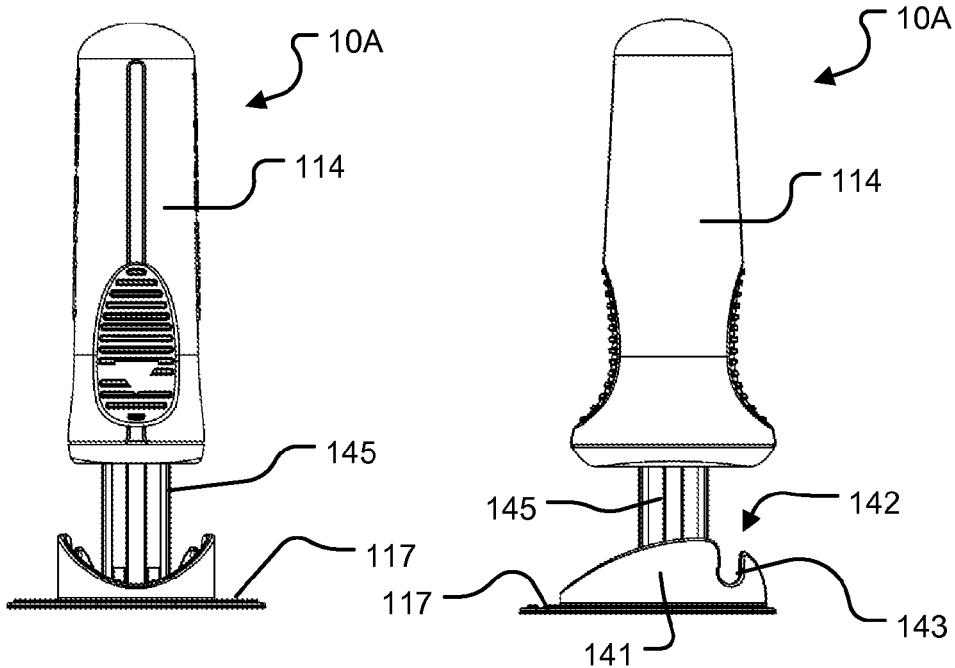
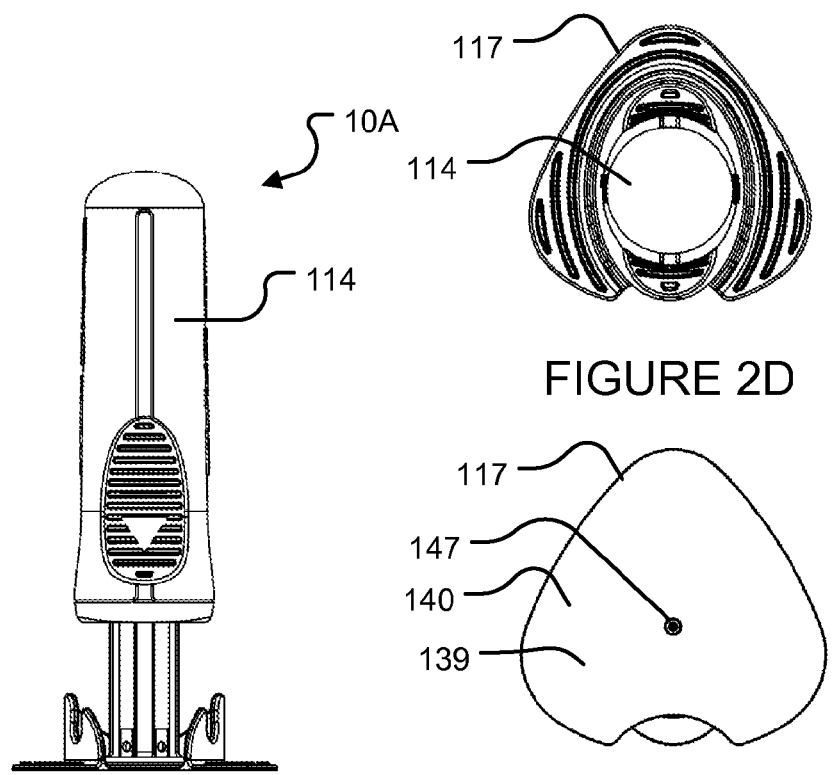
FIGURE 2A
FIGURE 2B
FIGURE 2C
FIGURE 2D
FIGURE 2E

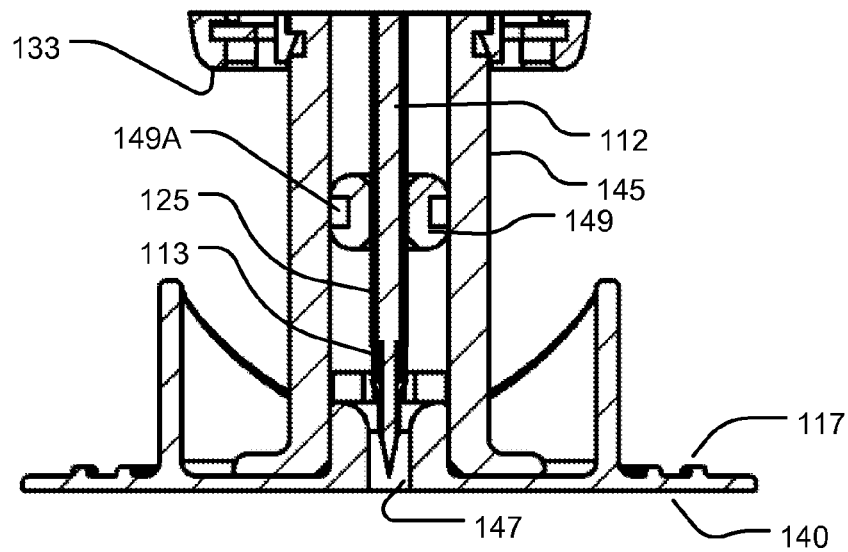
FIGURE 2K
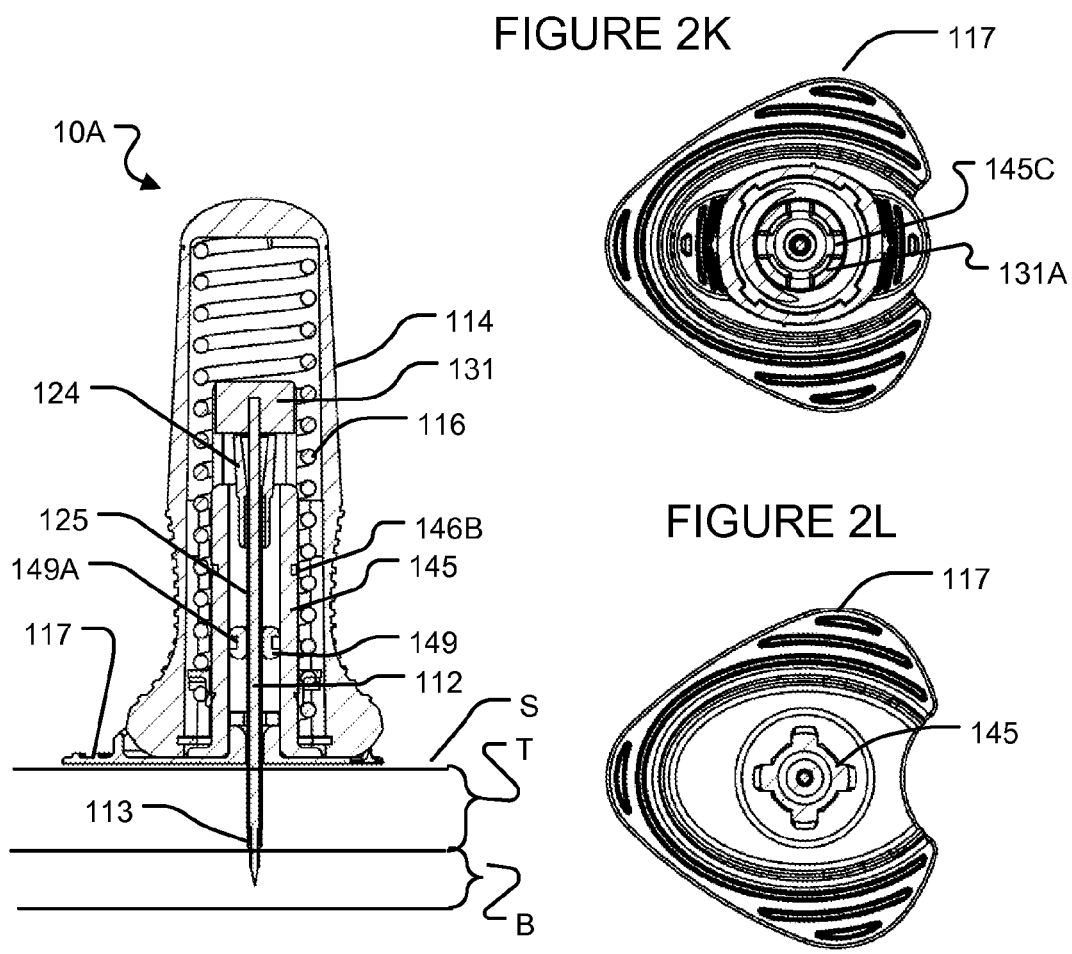
FIGURE 2L
FIGURE 2J
FIGURE 2M

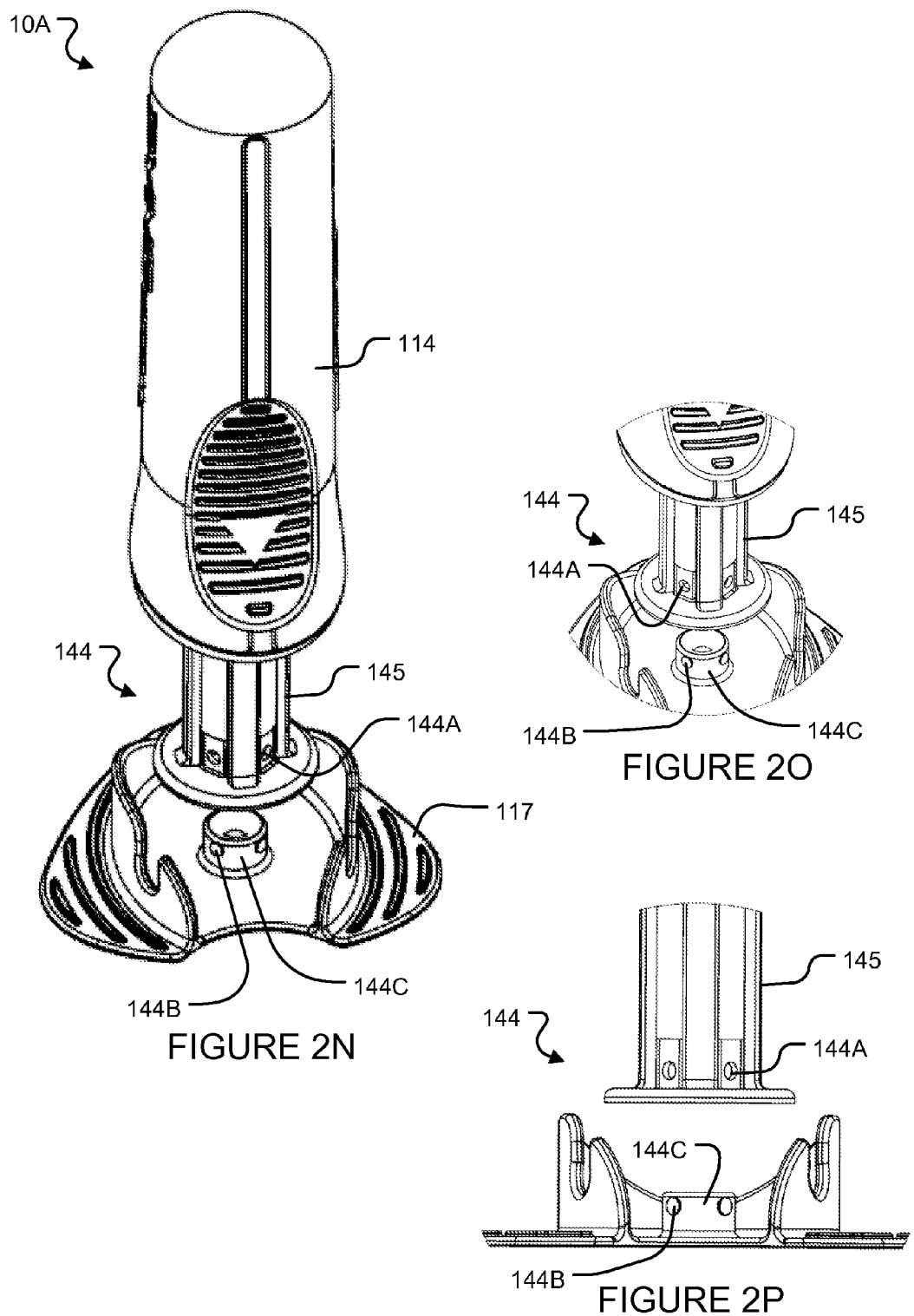

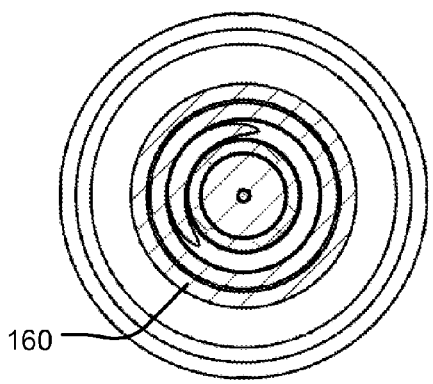
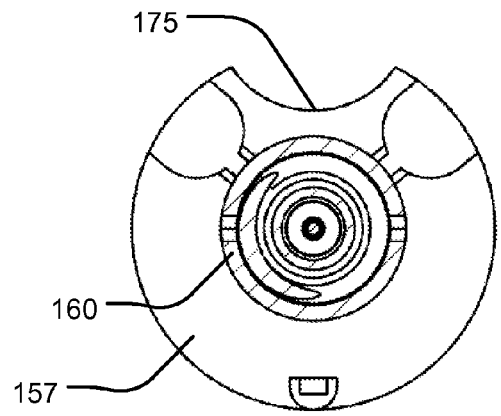
FIGURE 3I  FIGURE 3J
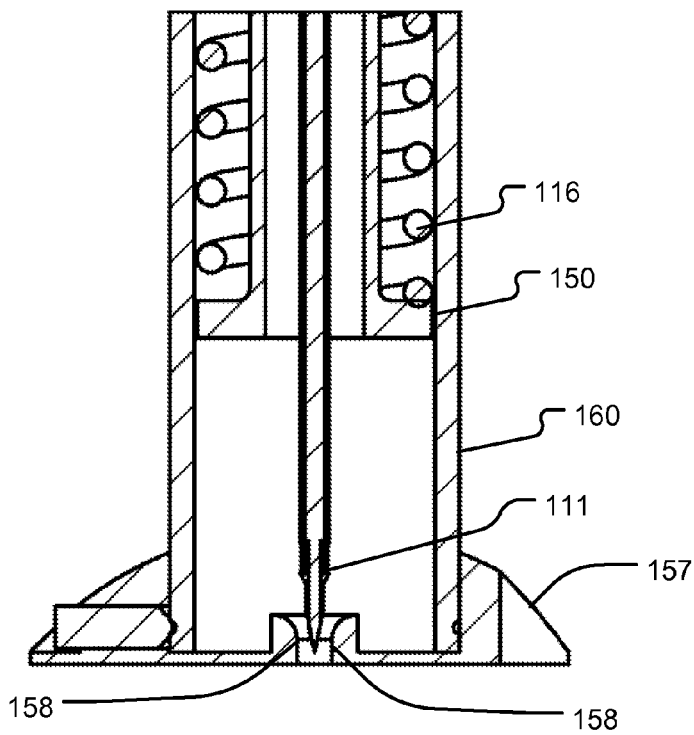
FIGURE 3K

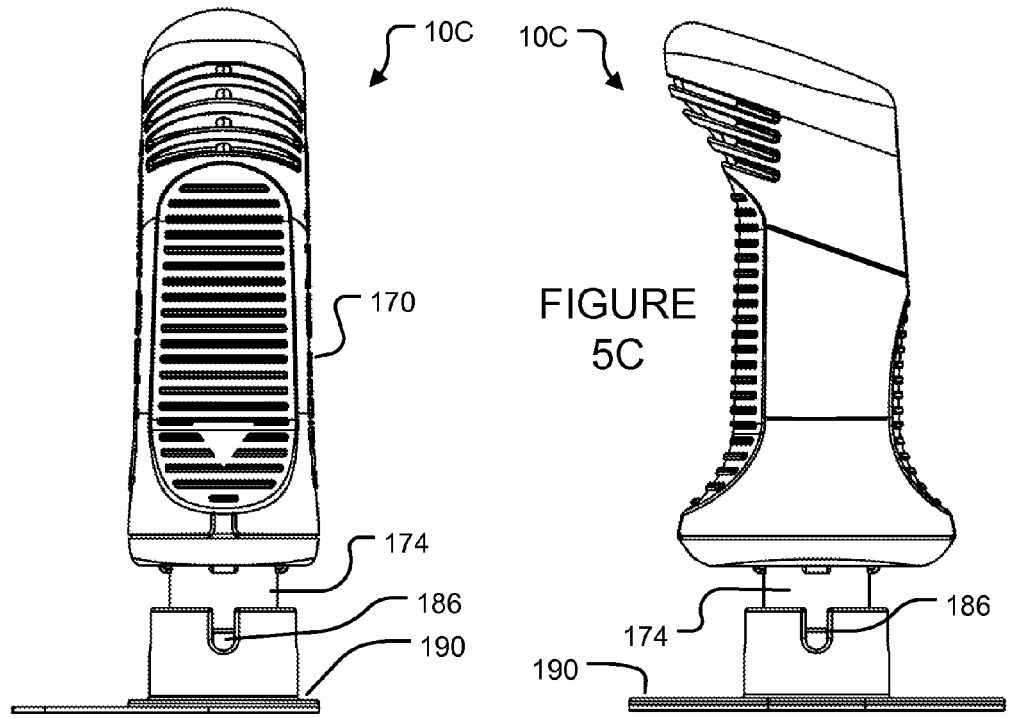
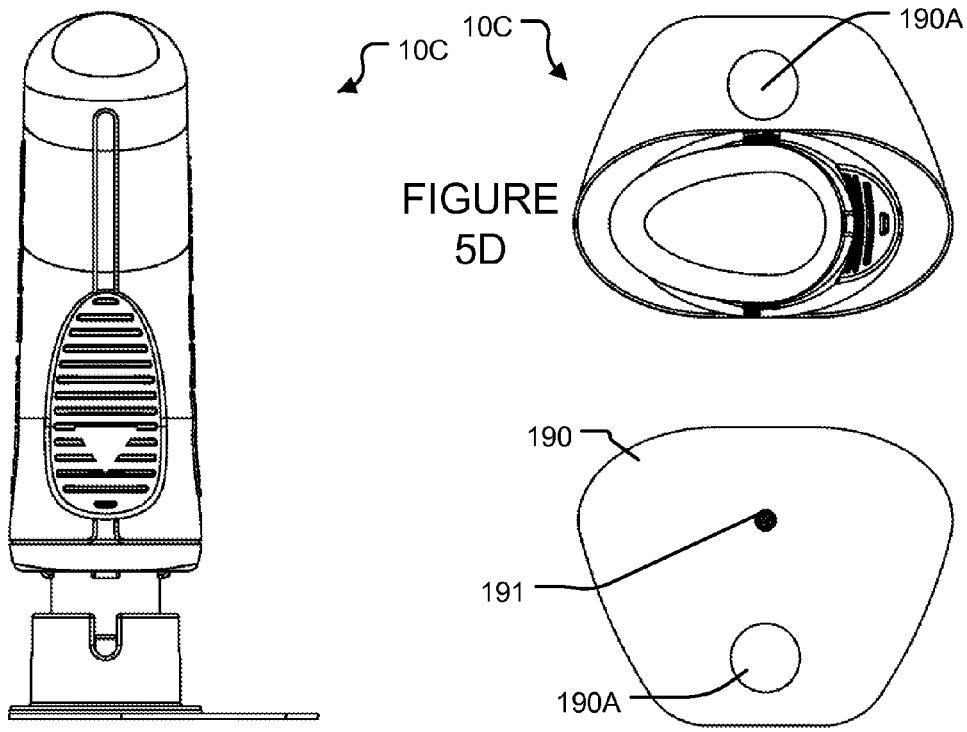

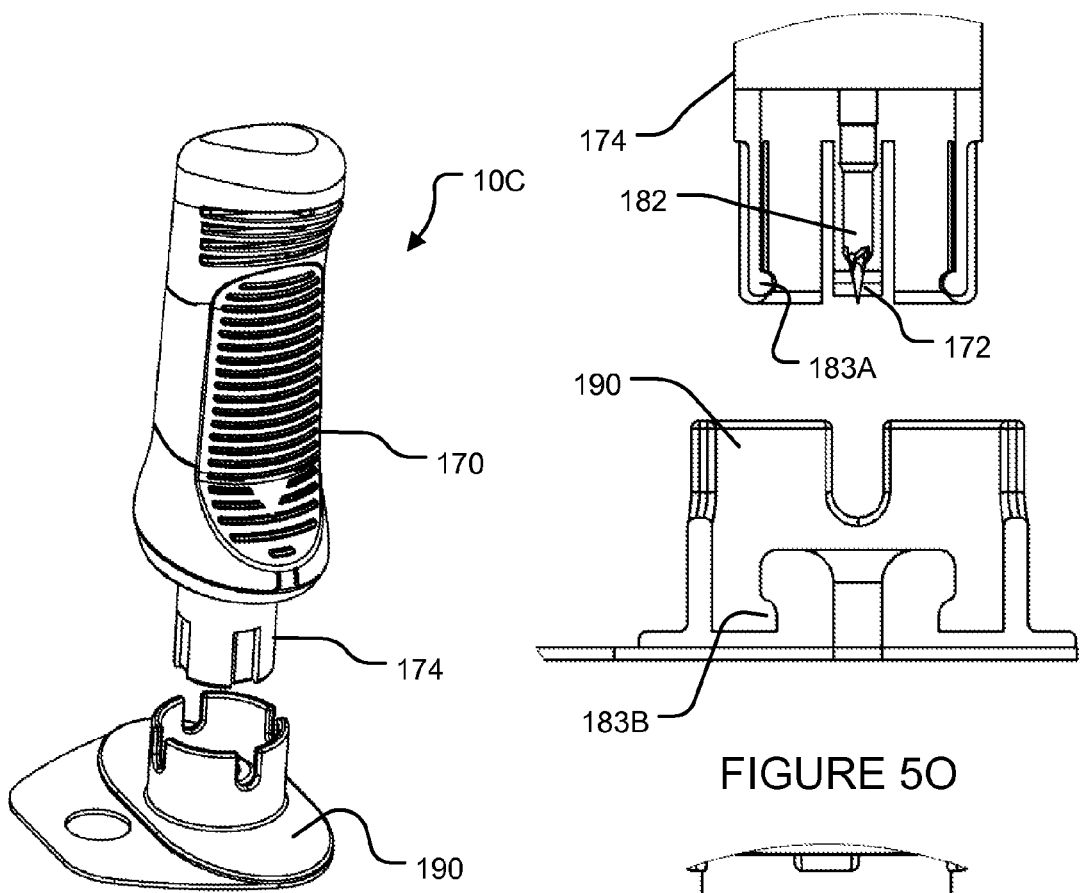
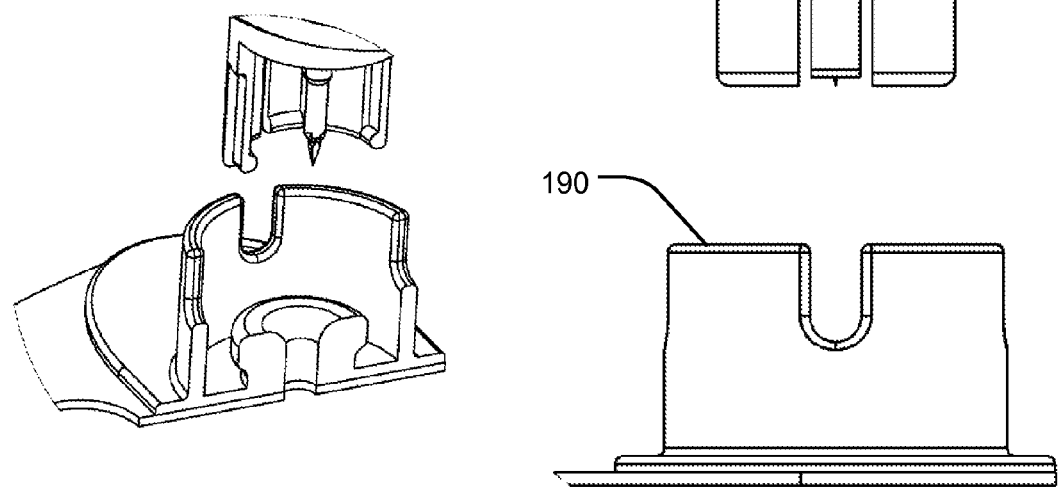
FIGURE 5N
FIGURE 5O
FIGURE 5P
FIGURE 5Q

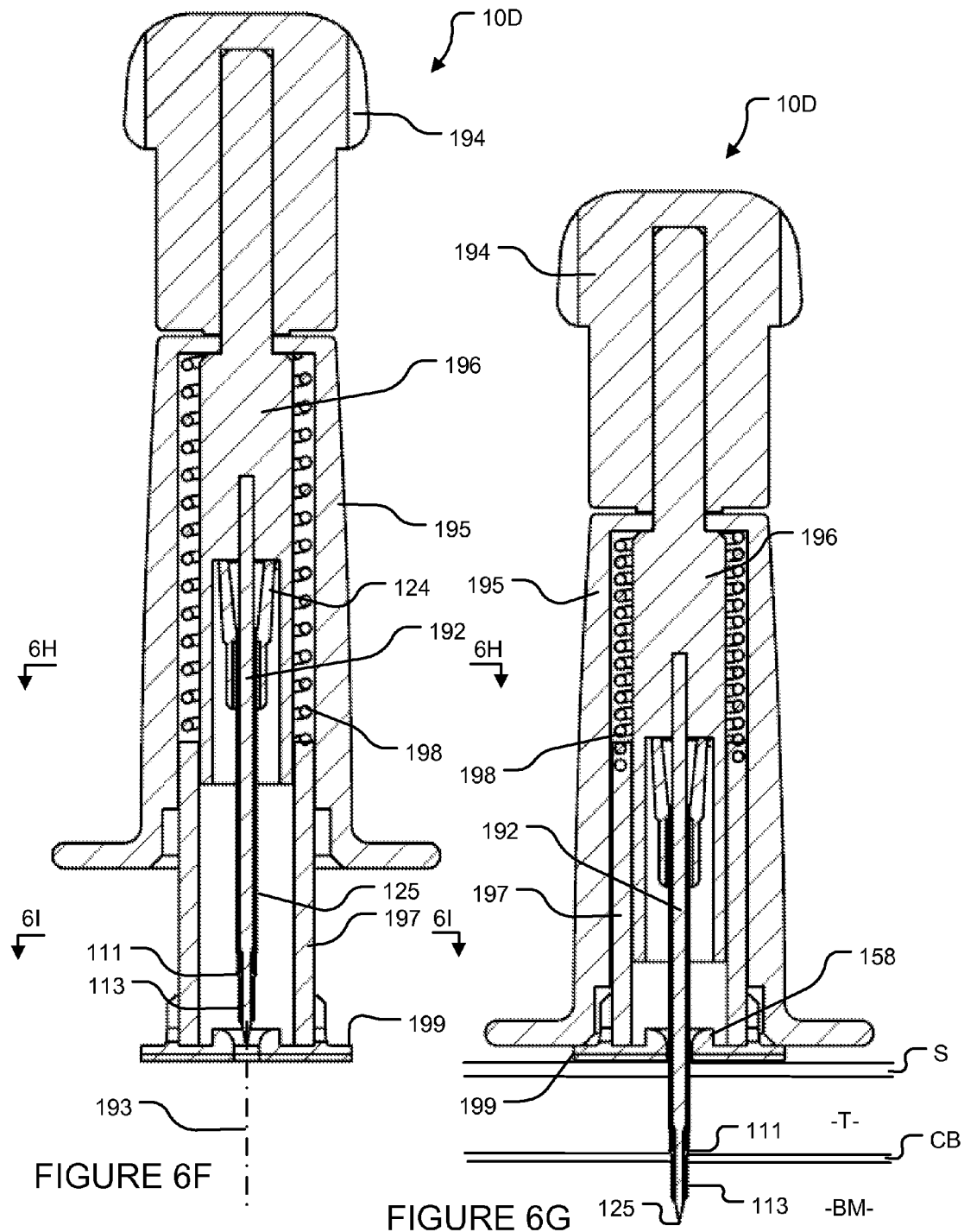

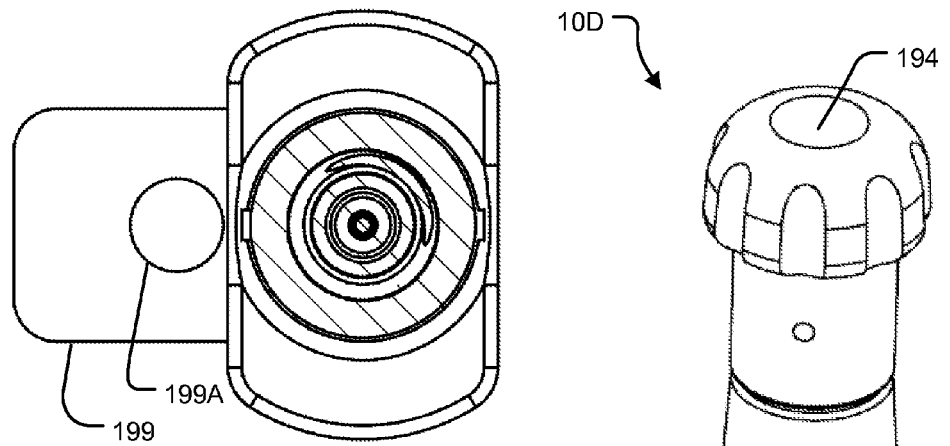
FIGURE 6H
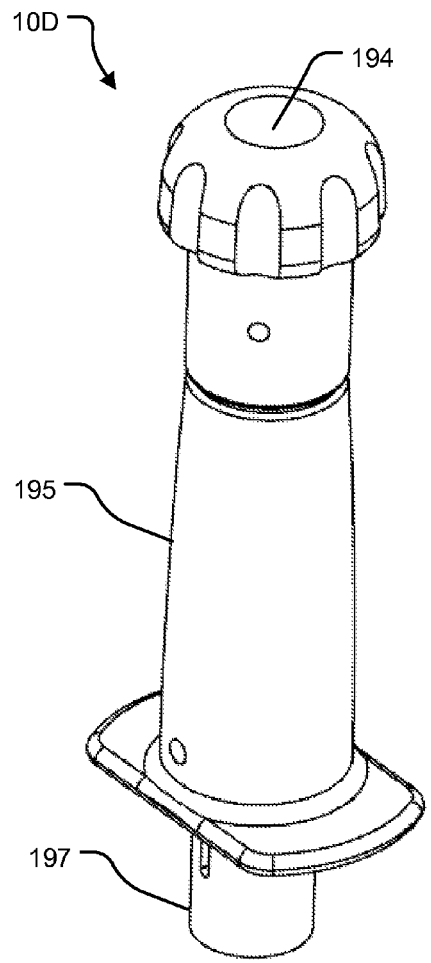
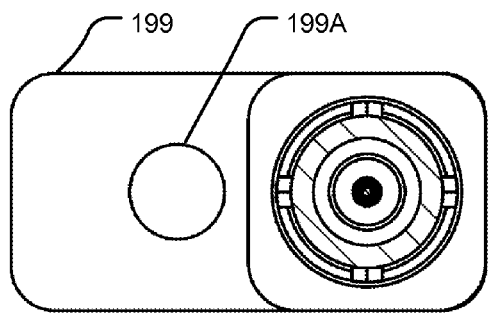
FIGURE 6I
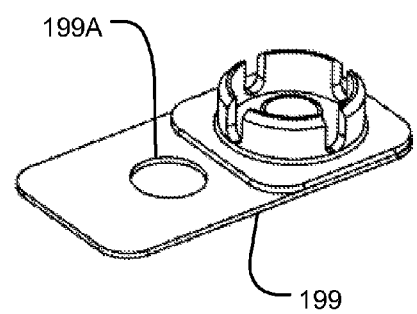
FIGURE 6J

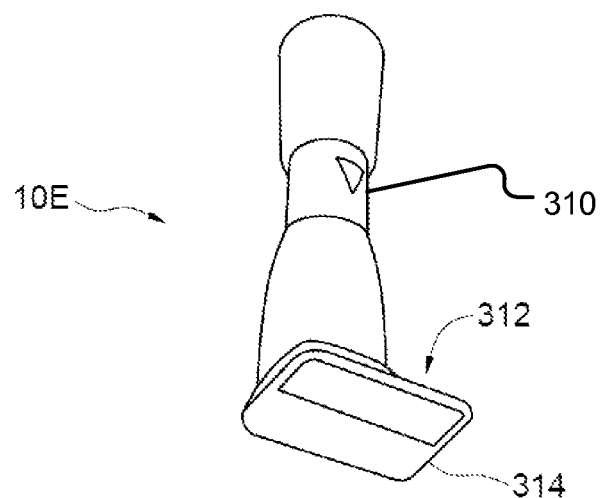
FIGURE 8A
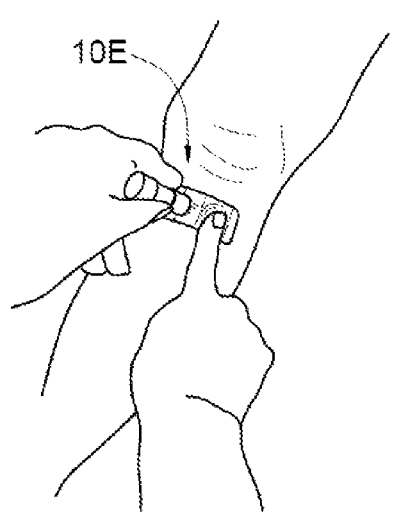 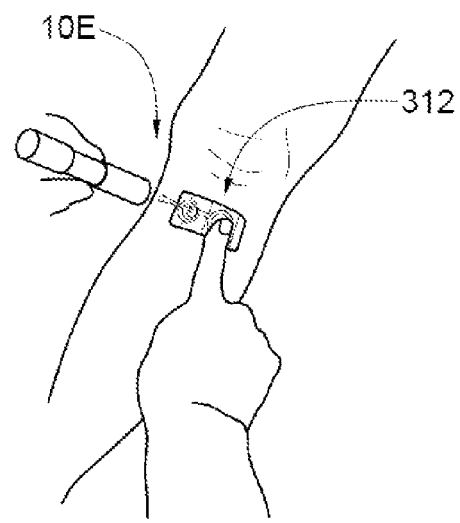
FIGURE 8B                FIGURE 8C

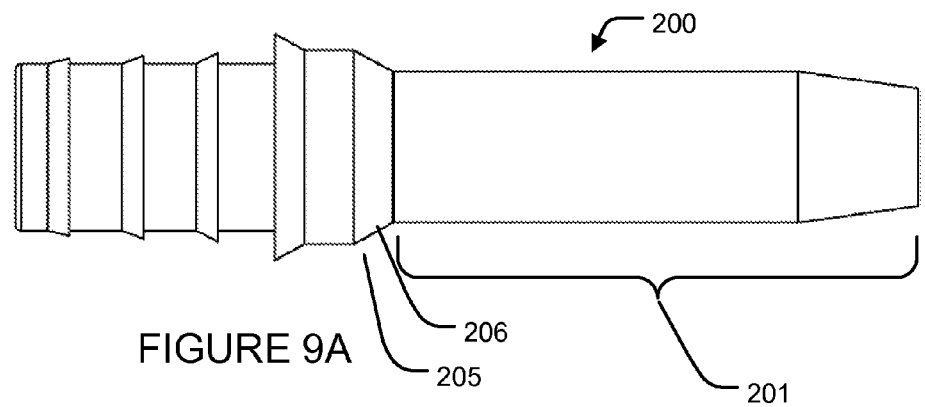
FIGURE 9A
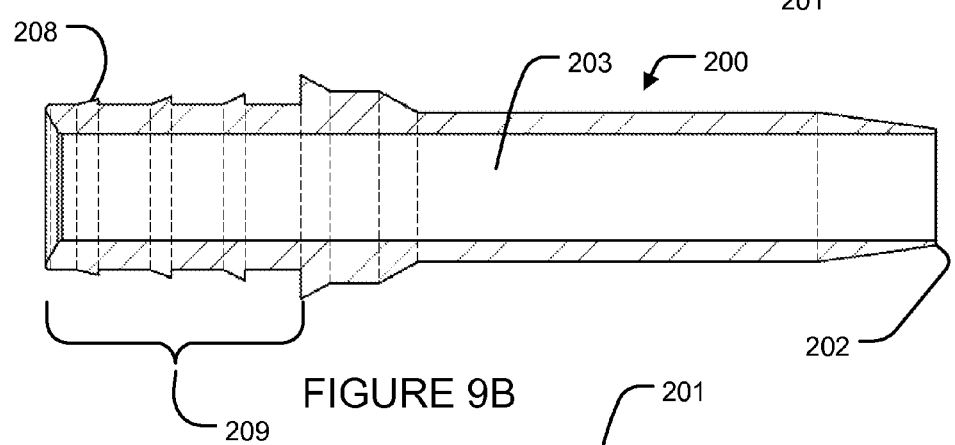
FIGURE 9B
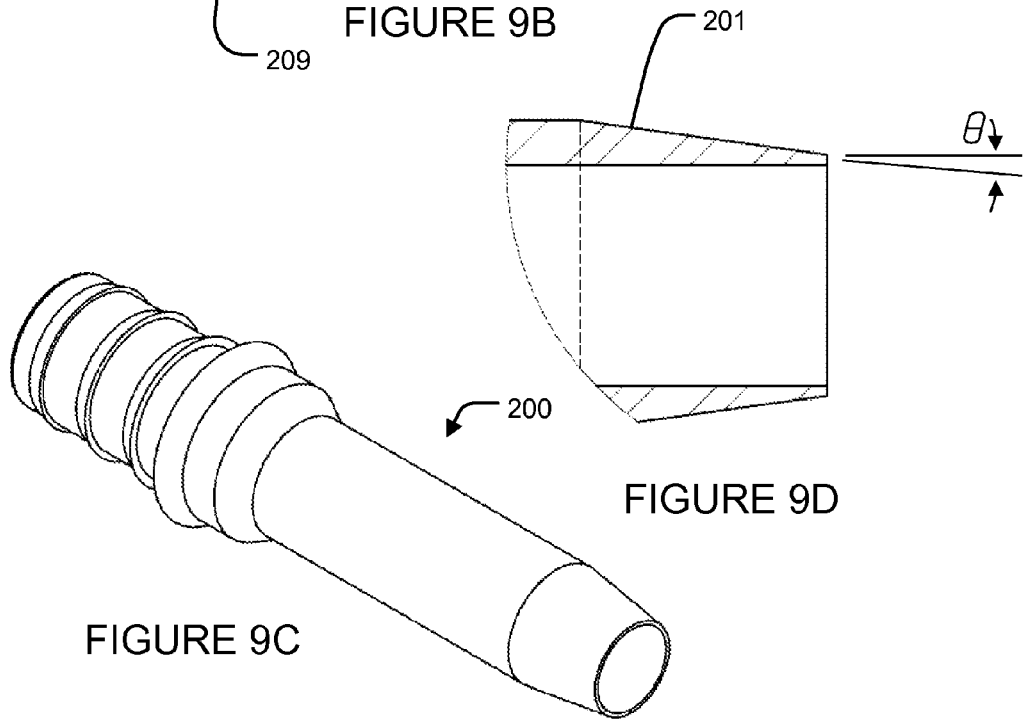
FIGURE 9C
FIGURE 9D

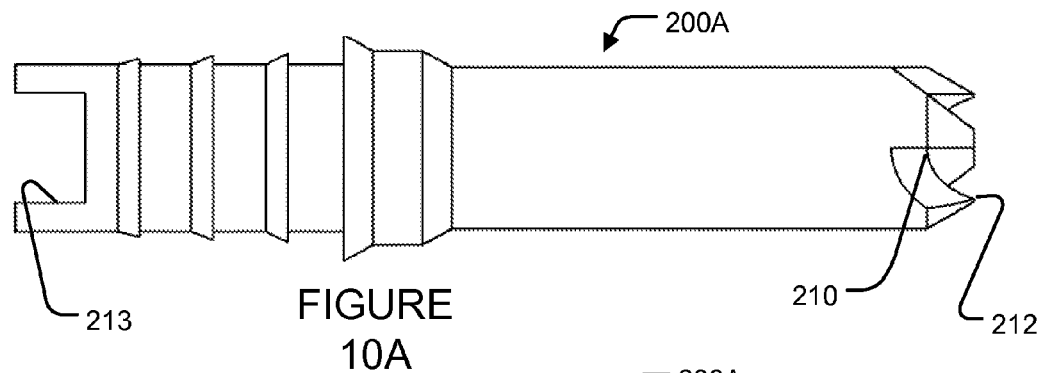
FIGURE 10A
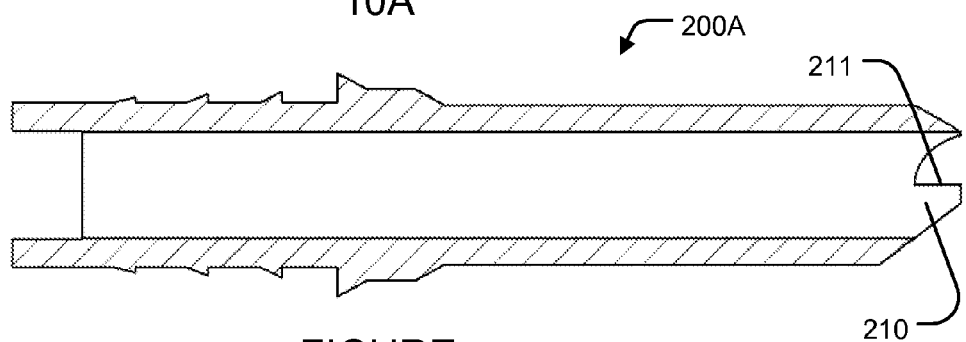
FIGURE 10B
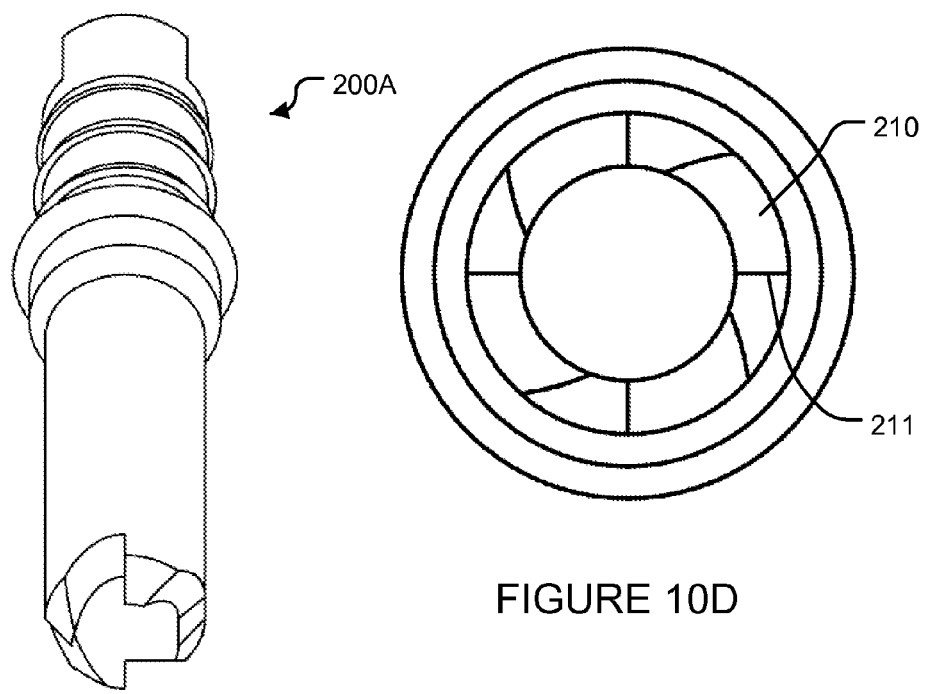
FIGURE 10D
FIGURE 10C

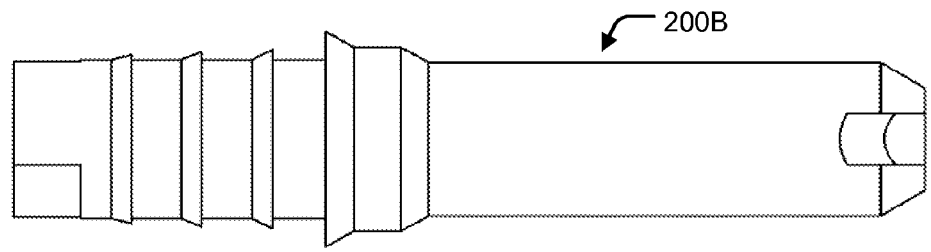
FIGURE
11A
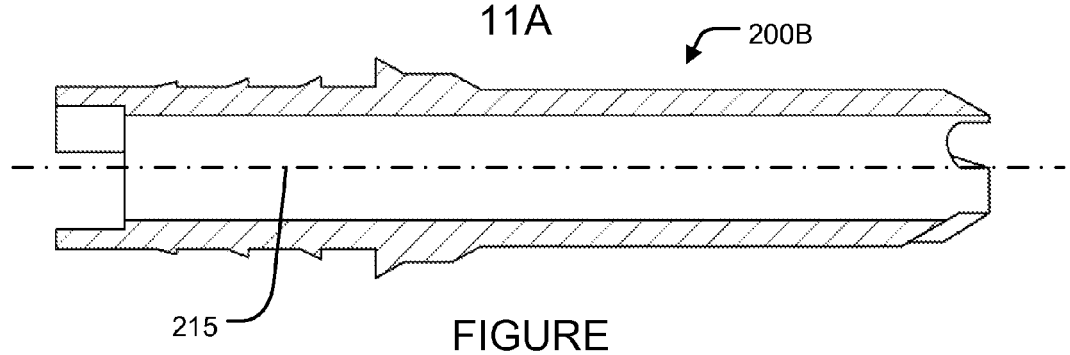
215
FIGURE
11B
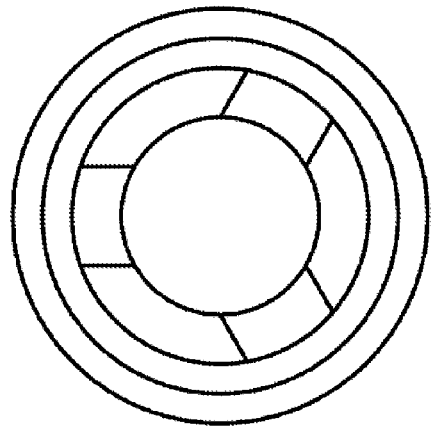
FIGURE 11D
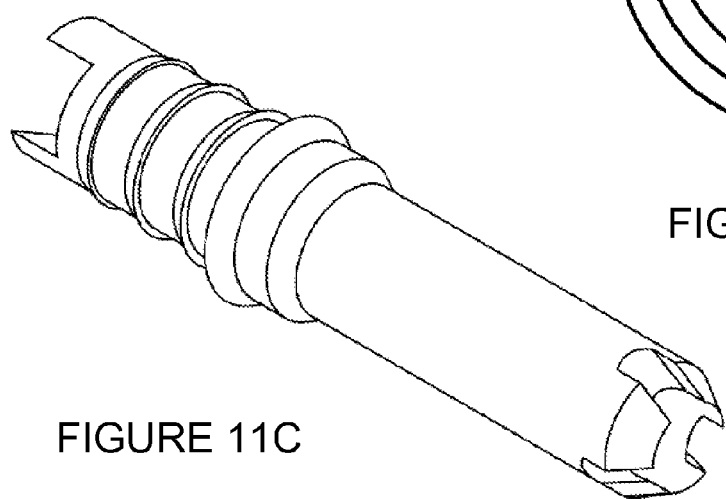
FIGURE 11C

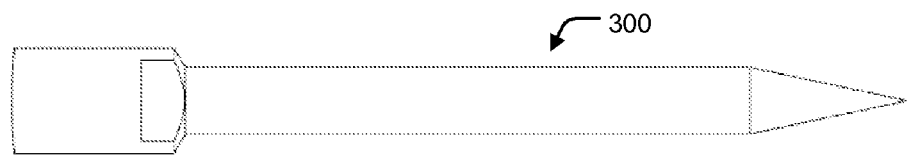
FIGURE
15A
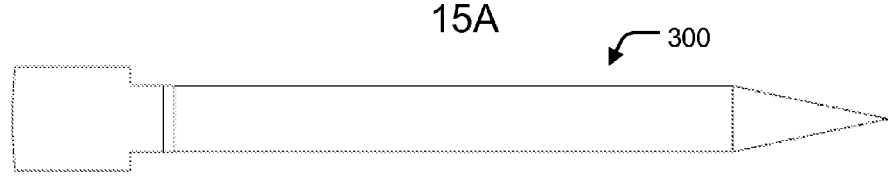
FIGURE
15B
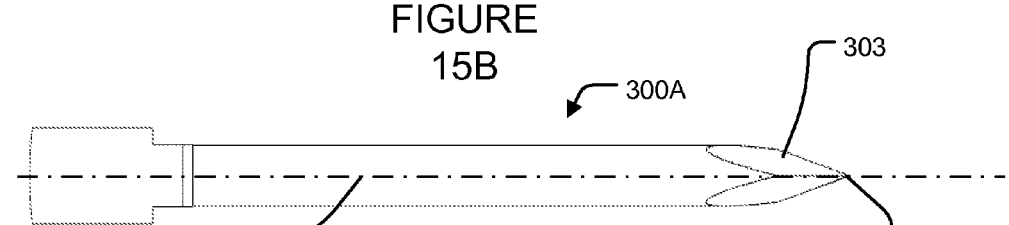
FIGURE
16A
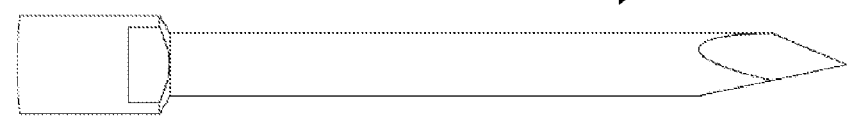
FIGURE
16B
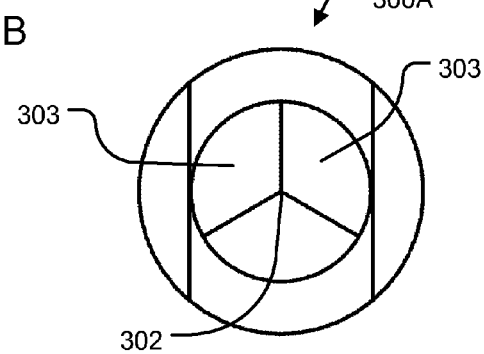
FIGURE 16C

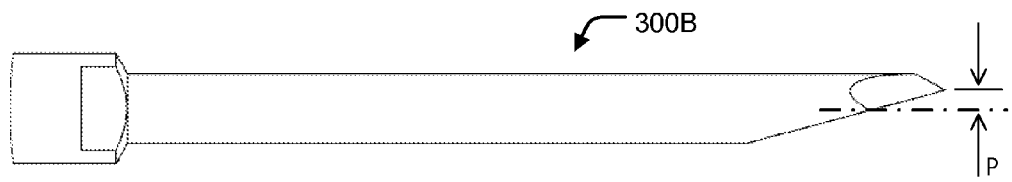
FIGURE
17A
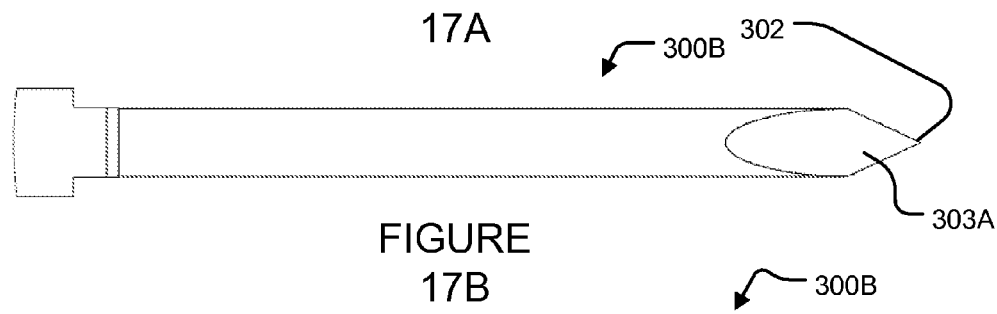
FIGURE
17B
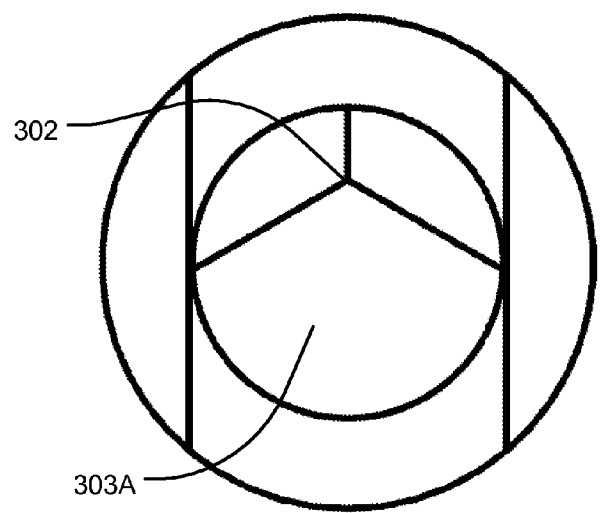
FIGURE 17D
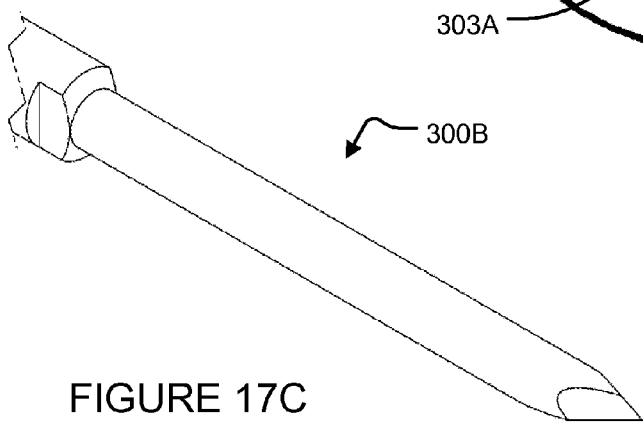
FIGURE 17C

APPARATUS FOR INTRODUCING PORTALS IN BONE HAVING TRANSVERSELY MOVABLE BONE PROBE

RELATED APPLICATIONS

This application is a continuation of U.S. patent application Ser. No. 12/851,546 filed 5 Aug. 2010, which is a continuation of U.S. patent application Ser. No. 12/745,557 filed 31 May 2010, which is a 371 of International Application No. PCT/CA2008/002146 filed 5 Dec. 2008, which claims priority to U.S. Patent Application Ser. No. 61/012,372 filed 7 Dec. 2007 and U.S. Patent Application Ser. No. 61/104,684 filed 10 Oct. 2008, each of which is hereby incorporated by reference in its entirety. For purposes of the United States of America, this application claims the benefit under 35 U.S.C. §119 of U.S. Patent Application Ser. No. 61/012,372 filed 7 Dec. 2007 and U.S. Patent Application Ser. No. 61/104,684 filed 10 Oct. 2008.

TECHNICAL FIELD

This invention relates to methods and apparatus for introducing portals into bone. The methods and apparatus may be applied, for example, to introduce a portal or a device such as an infusion tube into the sternum, tibia, or other bones for the purpose of intraosseous infusion. Embodiments of the invention provide: bone portals; introducer tools for introducing portals into bones; stylets for penetrating bones; and methods for introducing portals into bones.

BACKGROUND

There are various circumstances under which it is desirable to introduce drugs or other liquids into the marrow of a subject's bone. For example, in cases where a subject has suffered from serious trauma or cardiac arrest it may not be practical to deliver liquids by way of intravenous (IV) infusions. Intraosseous infusion may also be useful for delivering fluids to newborns and small children in which suitable blood vessels are difficult to access. Intraosseous infusion may be used to deliver fluids into a subject's sternum, femur, tibia, or other bone. Intraosseous infusion has the advantage that, with appropriate technology, a pathway for intraosseous infusion can be established very rapidly. This can save lives in critical situations. Portals in bone may also be applied to withdraw or aspirate fluid from within the bone.

Findlay et al. U.S. Pat. No. 6,761,726 entitled Method and Apparatus for the Intraosseous Introduction of a Device Such as an Infusion Tube describes apparatus capable of introducing an infusion tube to a predetermined depth in the marrow of a bone. Apparatus generally like that described in Findlay et al. has been marketed under the trademark FAST 1 by Pyng Medical Corp. of Richmond, British Columbia Canada and has achieved significant commercial success. Intraosseous infusion apparatus and techniques are also disclosed in WO 97/24151 and U.S. Pat. No. 5,817,052.

SUMMARY OF THE INVENTION

This invention has a range of aspects that may be applied in various combinations or individually. These aspects include:
  introducer tools having a handle coupled to a stylet by a force-limiting mechanism;
  methods for inserting a bone portal using an introducer tool having a handle coupled to a stylet by a force-limiting mechanism;
  introducer tools having a release mechanism comprising a split ring;
  introducer tools having a bone probe that can be moved away from a stylet to allow removal of a Luer fitting;
  introducer tools having a cartridge that becomes locked inside a handle after use;
  introducer tools having guide features on a base (possibly in combination with guide features on a handle);
  introducer tools designed for two-handed operation comprising a stylet rotatable by turning a knob and a base;
  introducer tools having a bone portal that is keyed to rotate with a stylet;
  introducer tools having an adhesive base and a stylet held (e.g. by way of a shield) at a desired angle (e.g. a right angle or a desired non-perpendicular angle) relative to the base);
  assemblies including a fitting such as a Luer fitting having an integrated strain relief member (possibly in combination with a base having an attachment for the strain relief member);
  depth control mechanisms useful, inter alia, for controlling depth of penetration of a portal or infusion tube being introduced into a subject's bone;
  portals having configurations including teeth and bone stops;
  detachable base assemblies for an introducer tool and associated mechanism;
  sharps protection systems;
  strain relief mechanisms;
  pivotally-mounted stylets;
  stylets that are movable relative to a bone probe in a transverse direction;
  stylets having offset points and introducer tools having such stylets; and
  dual use packaging having a portion including adhesive that can be applied to cover an insertion site.

One aspect of the invention provides apparatus for introducing a bone portal into a bone of a subject. The apparatus comprises a handle; a driving member adapted to support a bone portal; and, a force-limiting coupling operatively connecting the handle to the driving member.

Another aspect of the invention provides methods for placing a bone portal into a bone of a subject. The methods comprise placing against a subject an apparatus comprising: a handle; a driving member adapted to carry a bone portal; a force-limiting coupling operatively connecting the handle to the driving member; and a bone portal assembly comprising a bone portal supported on the driving member. The bone portal comprises a bone-penetrating portion projecting past a bone stop portion. The methods involve applying a force to the handle; allowing the force to be transmitted to the bone probe by way of the force-limiting coupling to drive the bone portal through tissue over the bone and to drive the bone-penetrating portion into the bone until the bone stop contacts the bone; and, subsequently operating the force-limiting coupling to limit the force transmitted from the handle to the driving member to a force insufficient to drive the bone stop of the bone portal into the bone.

Another aspect of the invention provides apparatus for introducing a bone portal into a bone of a subject. The apparatus comprises: a handle; a base; and a driving member. The driving member is movable between a first position wherein the driving member is retracted behind the base to a second position wherein the driving member projects past the base by operating the handle and the base is detachable from the handle.

Another aspect of the invention provides stylets for use in introducing a bone portal into a bone. The stylets comprise a shaft having a centerline and a tip at a first end of the shaft. The tip comprises a plurality of facets meeting at a point that is offset from the centerline.

Another aspect of the invention provides apparatus for introducing a bone portal into a bone. The apparatus comprises: a handle, and a carrier assembly comprising a driving member. The carrier assembly is slidably received within the handle and prevented from moving toward a distal end of the handle by a release mechanism. The release mechanism comprises: a split ring projecting radially out of a circumferential groove in the carrier assembly to engage an abutting surface of the handle. The split ring has a gap between two ends thereof. A sliding block is at least partly within the gap of the split ring. The sliding block is slidably movable out of the gap against a first bias force. A bone probe is coupled to the sliding block. The first bias force is insufficient to drive the bone probe into the bone.

Another aspect of the invention provides apparatus for introducing a bone portal into a bone. The apparatus comprises: a stylet capable of supporting an infusion tube assembly comprises a bone portal and a handle drivingly coupled to the stylet by a release mechanism. The release mechanism comprises a bone probe extending generally parallel to the stylet. The release mechanism is operative to uncouple the driving coupling between the handle and the stylet upon longitudinal motion of the bone probe. The stylet and the bone probe are moveable, for example, pivotally movable, relative to one another.

Another aspect of the invention provides apparatus for introducing a bone portal into a bone. The apparatus comprises a carriage assembly slidably received within the handle and prevented from moving toward a distal end of the handle by a release mechanism. The carriage assembly comprises a stylet projecting from the handle. A ratchet mechanism is connected between the carriage assembly and the handle. The ratchet mechanism is configured to permit the carriage assembly to move toward the distal end of the handle upon operation of the release mechanism and to prevent subsequent withdrawal of the carriage assembly.

Another aspect of the invention provides bone portals for placement in a bone of subjects. The bone portals comprise a body having a proximal end and a distal end. The body comprises a tubular bone-penetrating portion comprises an annular leading edge having cutting features defined therein at the proximal end. The bone-penetrating portion projects from a bone stop. The bone portal has a drive coupling at the distal end.

Another aspect of the invention provides packaging which may be used for medical devices. The packaging comprises first and second portions sealed together to enclose an interior volume for holding the medical device. The first portion comprises a generally planar flange bearing adhesive and a release sheet covering the adhesive.

Another aspect of the invention provides apparatus for introducing a bone portal into a bone of a subject. The apparatus comprises: a handle; a driving member configured to support a bone portal operatively connected to the handle; a retractable shield extending from the handle; and a base coupled to the shield. The base comprises at least one guide feature to indicate a desired alignment with at least one anatomical feature of the subject.

Another aspect of the invention provides apparatus for introducing a bone portal into a bone of a subject. The apparatus comprises: a handle and a stylet coupled to be driven in rotation by a knob on the handle. The stylet is slidably supported within a shield that is biased to project from the handle. The apparatus includes a base coupled at a proximal end of the shield.

Another aspect of the invention provides infusion tube assemblies. The infusion tube assemblies comprise a bone portal, a fitting, a flexible tube coupling the bone portal to the fitting, and a strain relief member extending from the fitting.

Further aspects of the invention and non-limiting example embodiments of the invention are described below and illustrated in the accompanying drawings.

BRIEF DESCRIPTION OF DRAWINGS

Example embodiments illustrating the application of a range of aspects of the invention are illustrated in the attached drawings. The embodiments disclosed herein are illustrative and non-limiting.

FIGS. 2A to 2P are views of an introducer tool according to an example embodiment. FIGS. 2A, 2B, 2C, 2D and 2E are respectively front, side, rear, top and bottom views of the introducer tool. FIG. 2J, is a cross-sectional side elevation view of the introducer tool in an extended configuration. FIG. 2K is a detail cross-sectional view showing stylet guides in a base. FIGS. 2L and 2M are respectively cross-sectional views in the planes 2L-2L and 2M-2M shown in FIG. 2I. FIG. 2N is an isometric view of the introducer tool with its base removed. FIGS. 2O and 2P are respectively isometric and elevation detail views showing the interface between a shield and base of the introducer tool.

FIGS. 3A to 3N are views of an introducer tool according to another example embodiment. FIGS. 3A, 3B, 3C, 3D and 3E are respectively front, side, rear, top and bottom views of the introducer tool. FIGS. 3I and 3J are respectively cross-sectional views in the planes 3I-3I and 3J-3J shown in FIG. 3L. FIG. 3K is a detail cross-sectional view showing stylet guides in a base.

FIGS. 3L, 3M and 3N are cross-sectional elevational views. FIG. 3L shows the introducer tool in an initial configuration. FIG. 3M shows the introducer tool with its stylet partially extended. FIG. 3N shows the introducer tool with the stylet fully extended.

FIG. 4A is a side elevation view with the enclosure cut away to show the introducer tool. FIG. 4B is an exploded isometric view. FIGS. 4C and 4D are side and front elevation views. FIG. 4E is a top view.

FIGS. 5A to 5Q are views showing an introducer tool according to another embodiment of the invention. FIGS. 5A, 5B, 5C, 5D and 5E are respectively front, rear, side, top and bottom views of the introducer tool. FIG. 5N is an isometric view of the introducer tool with its base portion removed. FIGS. 5O, 5P and 5Q are respectively cross-sectional elevation, cut-away isometric and elevation detail views showing the interface between a shield and base of the introducer tool.

FIGS. 6A to 6J show an introducer tool according to another embodiment of the invention. FIG. 6A is a front elevation view of the introducer tool. FIG. 6B is a side elevation view of the introducer tool. FIG. 6C is an isometric view of the introducer tool. FIGS. 6D and 6E are respectively bottom and top views of the introducer tool. FIGS. 6F and 6G are cross-sectional elevation views of the introducer tool in its initial and extended configurations. FIGS. 6H and 6I are transverse cross sections of the introducer tool respectively as seen in the planes 6H-6H and 6I-6I indicated in FIG. 6F. FIG. 6J is an isometric view of the introducer tool with its base detached.

FIG. 7A is an isometric view of the portal and stylet combination. FIG. 7B is a side elevation view of the portal and stylet combination.

FIGS. 8A to 8C show an introducer tool according to another embodiment of the invention. FIG. 8A is a isometric view of the introducer tool. FIGS. 8B and 8C show a use of the introducer tool on a tibial target site.

FIGS. 9A to 9D are views of a portal according to an embodiment of the invention. FIGS. 9A, 9B and 9C are respectively side, cross-sectional side and perspective views of the portal. FIG. 9 is a cross-sectional detail view of the leading edge of the portal.

FIGS. 10A to 10D are views of a portal according to another embodiment of the invention. FIGS. 10A, 10B, 10C and 10D are respectively side, cross-sectional side, perspective and front views of the portal.

FIGS. 11A to 11D are views of a portal according to another embodiment of the invention. FIGS. 11A, 11B, 11C and 11D are respectively side, cross-sectional side, perspective and front views of the portal.

FIGS. 12A, 12B, 12C, 12D and 12E are respectively side, cross-sectional side, rear, front and perspective views of the portal.

FIGS. 15A and 15B are views of a sharp stylet having a conical tip according to an embodiment of the invention.

FIGS. 16A to 16C are views of a faceted stylet having a symmetrical point. FIGS. 16A and 16B are side views of the stylet. FIG. 16C is a front view of the stylet.

FIGS. 17A to 17D are views of a faceted stylet having an asymmetrical point. FIGS. 17A and 17B are side views of the stylet. FIGS. 17C and 17D are respectively perspective and front views of the stylet.

Figure 1:
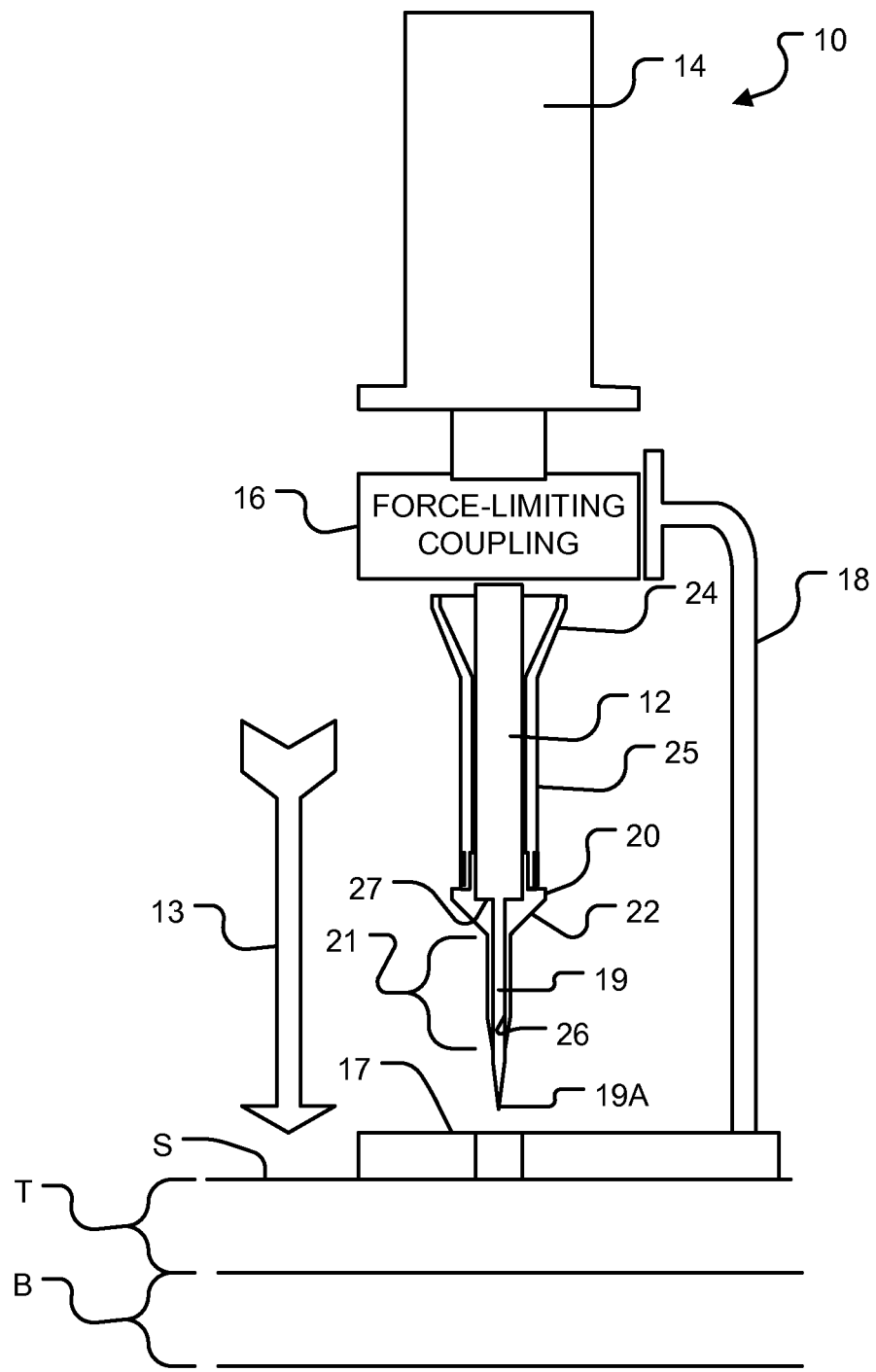
FIG. 1 shows schematically an introducer tool for placing bone portals according to an example embodiment of the invention.
Figures 2F, 2G:
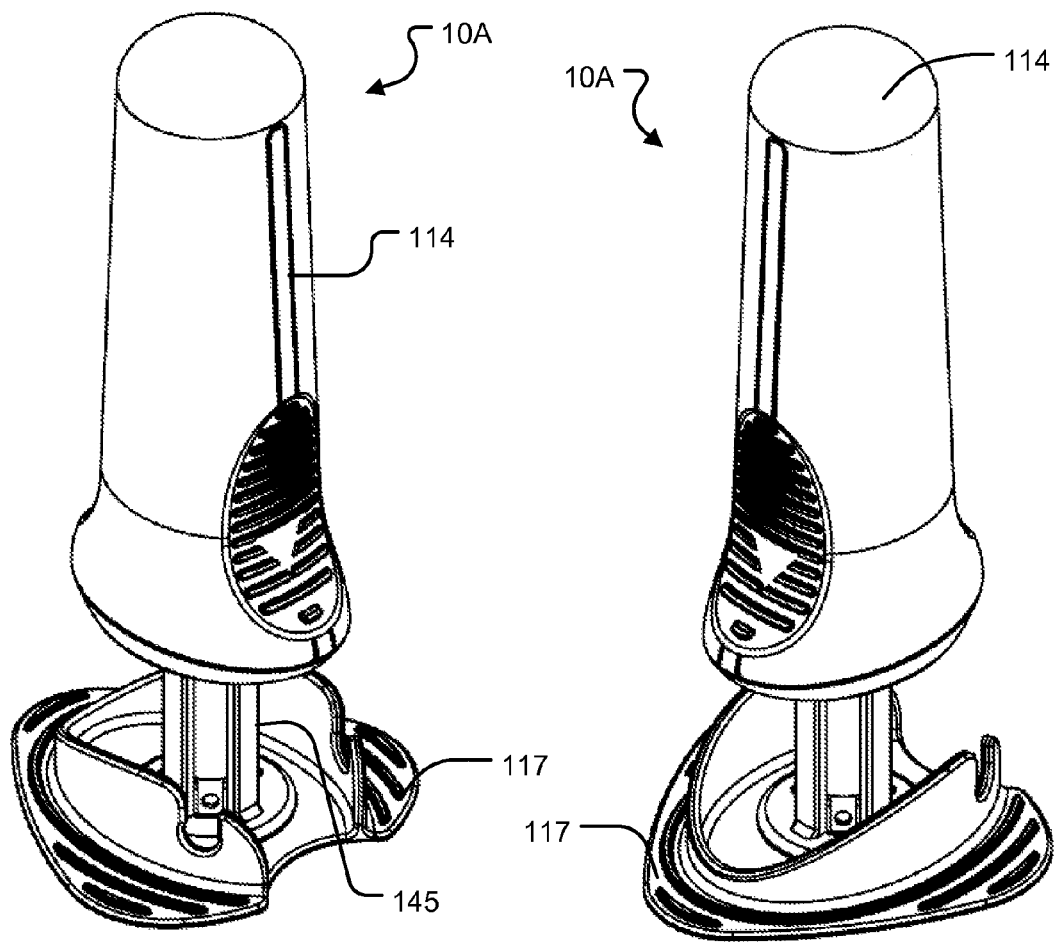
FIGS. 2F and 2G are isometric views of the introducer tool.
Figure 2H:
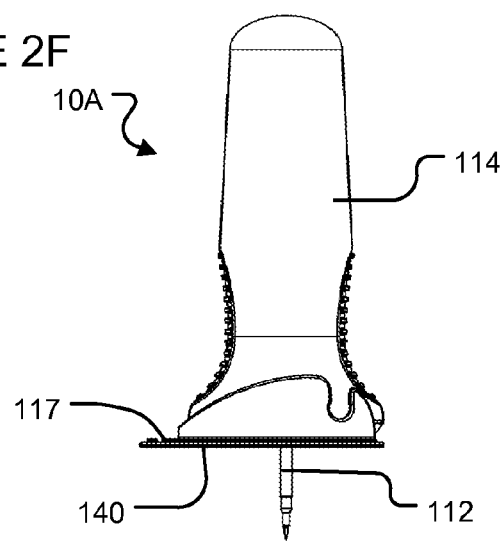
FIG. 2H is a side view of the introducer tool in an extended configuration.
Figure 2I:
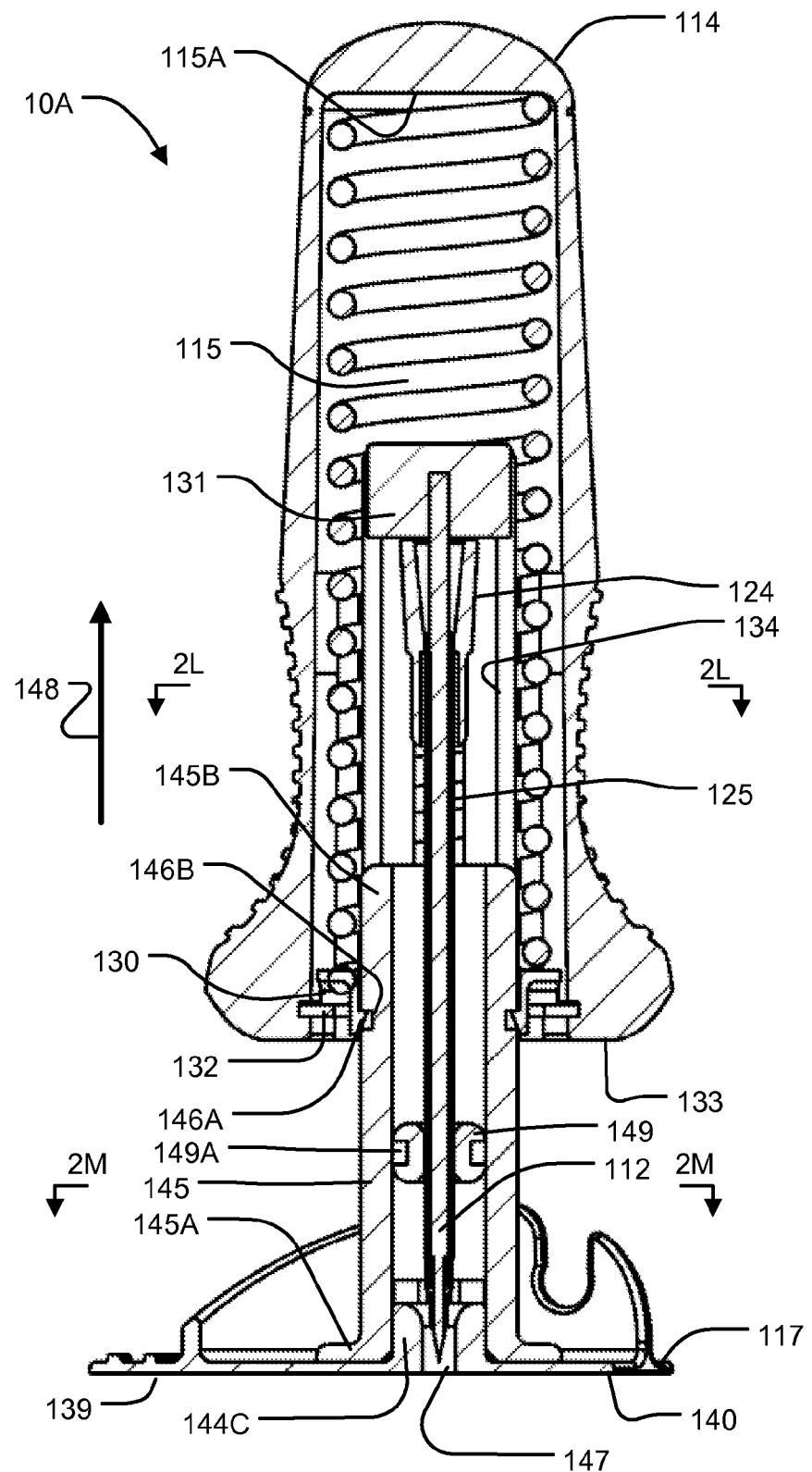
FIG. 2I is a cross-sectional side elevation view of the introducer tool.

| List of Reference Characters | |
|---|---|
| subject's bone | B |
| offset of stylet point | P |
| subject's skin | S |
| soft tissue | T |
| subject's cortical bone | CB |
| subject's bone marrow | BM |
| introducer tool | 10 |
| introducer tool | 10A |
| introducer tool | 10B |
| introducer tool | 10C |
| introducer tool | 10D |
| introducer tool | 10E |
| introducer tool | 10F |
| driving member | 12 |
| direction | 13 |
| handle | 14 |
| force limiting coupling | 16 |
| base | 17 |
| guide | 18 |
| stylet | 19 |
| stylet tip | 19A |
| bone portal | 20 |
| bone penetrating portion | 21 |
| bone stop | 22 |
| fitting | 24 |
| flexible tube | 25 |
| longitudinal bore | 26 |
| shoulder | 27 |
| bone stop | 111 |
| stylet | 112 |
| portal | 113 |
| handle | 114 |
| cavity | 115 |
| end | 115A |
| coil spring | 116 |
| base | 117 |
| fitting | 124 |
| tube | 125 |
| shoulder | 130 |
| stylet support member | 131 |
| retainer | 132 |
| proximal end | 133 |
| bore | 134 |
| adhesive | 139 |
| face | 140 |
| wall on base | 141 |
| strain relief fitting | 142 |
| notch | 143 |
| detachable coupling | 144 |
| projections | 144A |
| recesses | 144B |
| wall | 144C |
| shield | 145 |
| distal end | 145A |
| proximal end | 145B |
| teeth | 146A |
| recesses | 146B |
| opening in base | 147 |
| direction | 148 |
| spacer | 149 |

-continued

| List of Reference Characters | |
|---|---|
| groove in spacer | 149A |
| flange | 150 |
| stylet support member | 152 |
| stylet | 153 |
| spring retaining member | 154 |
| flange | 155 |
| pin | 156 |
| base | 157 |
| guide | 158 |
| longitudinal grooves | 159 |
| shield | 160 |
| pins | 161 |
| handle | 162 |
| longitudinal slots | 164 |
| sterile enclosure | 168 |
| first part | 168A |
| second part | 168B |
| handle | 170 |
| stylet | 172 |
| spacer | 172 |
| longitudinal axis | 173 |
| shield | 174 |
| open-sided recess | 175 |
| spring | 176 |
| spacers | 178 |
| tube | 180 |
| bone portal | 182 |
| projection | 183A |
| groove | 183B |
| fitting | 184 |
| groove | 185 |
| strain relief fittings | 186 |
| base | 190 |
| aperture | 190A |
| hole | 191 |
| stylet | 192 |
| axis | 193 |
| knob | 194 |
| handle | 195 |
| stylet support member | 196 |
| shield | 197 |
| spring | 198 |
| base | 199 |
| aperture | 199A |
| bone portal | 200 |
| bone portal | 200A |
| portal | 200B |
| portal | 200C |
| bone penetrating portion | 201 |
| leading edge | 202 |
| passage | 203 |
| facets | 204 |
| bone stop | 205 |
| tapered front face | 206 |
| cutting teeth | 207 |
| barbs | 208 |
| shank portion of portal | 209 |
| teeth | 210 |
| cutting edges | 211 |
| leading edge | 212 |
| key or notch | 213 |
| longitudinal axis | 215 |
| cutting teeth | 220 |
| stylet | 300 |
| stylet | 300A |
| stylet | 300C |
| symmetry | 301 |
| point | 302 |
| handle | 310 |
| base | 312 |
| release sheet | 314 |
| handle | 412 |
| grip | 412A |
| resilient surface | 412B |
| base | 414 |
| infusion tube assembly | 415 |
| bone portal | 415A |
| infusion tube | 415B |

-continued

| List of Reference Characters | |
|---|---|
| fitting | 415C |
| strain relief member | 415D |
| aperture | 415E |
| ferrule | 415F |
| shield | 416 |
| bottom surface of base | 418 |
| adhesive | 419 |
| release sheet | 419A |
| stylet | 420 |
| stylet tip | 420A |
| bone probe | 422 |
| tip of bone probe | 422A |
| spring | 424 |
| locking pin assembly | 425 |
| locking pin | 425A |
| carrier assembly | 430 |
| release mechanism | 431 |
| sleeve | 432 |
| cavity | 433 |
| coupling | 434 |
| release ring | 436 |
| angled surface | 437 |
| groove for release ring | 438 |
| gap in release ring | 439 |
| sliding block | 440 |
| sliding carrier | 442 |
| spring | 444 |
| pin | 445 |
| pawl | 447 |
| recesses | 448 |
| mounting base | 449 |
| stiffener | 450 |
| tab on shield416 | 452A |
| recess in sleeve 432 | 452B |
| block on shield 416 | 453A |
| abutment surface on sleeve 432 | 453B |
| groove in shield416 | 454A |
| rib on sleeve 432 | 454B |
| base release mechanism | 460 |
| tab | 462 |
| barb | 462A |
| recess | 462B |
| actuating member | 464 |
| finger | 464A |
| profile | 464B |
| holding feature | 465 |
| raised surface | 467 |
| guide aperture | 468 |
| guide aperture | 469 |
| wall | 470 |
| strain relief fitting | 474 |
| hook | 475 |
| guide plate | 476 |
| edge of base | 477 |
| section of base edge | 478 |
| recess | 479 |
| wall | 480 |
| stylet base | 482 |
| cavity | 484 |
| packaging | 490 |
| lid portion | 492 |
| flange | 494 |
| adhesive | 495 |
| release sheet | 496 |

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

This disclosure describes a wide range of embodiments of introducer tools for bone portals, bone portals, bases for use in conjunction with introducer tools for bone portals, stylets for use in introducers for bone portals as well as other applications, dual use packaging for use in introducers for bone portals as well as other applications, strain relief fittings for use in introducers for bone portals as well as other applications, and associated methods. Various embodiments are described in which specific combinations of features are present. Except as otherwise stated or necessarily implied, the features described herein may be combined in combinations other than those expressly described in the example embodiments discussed herein and depicted in the accompanying drawings. All such combinations and sub-combinations thereof are included within the scope of inventive subject matter described herein.

FIG. 1 shows schematically an introducer tool 10 according to an example embodiment of the invention for placing a bone portal 20. Bone portal 20 comprises a bone-penetrating portion 21 and a bone stop 22. In this description, 'distal' refers to a direction toward a handle of an introducer tool, and 'proximal' refers to a direction toward a base of an introducer tool.

Introducer tool 10 comprises a driving member 12 that engages bone portal 20, a handle 14 to which a user can apply force to drive bone-penetrating portion 21 of portal 20 in direction 13 into a bone. A force-limiting coupling 16 couples handle 14 to driving member 12.

Introducer tool 10 may be applied to drive portal 20 into a subject's bone by:
  placing portal 20 over the location on the bone at which it is desired to insert portal 20;
  supporting tool 10 so that portal 20 is at a desired angle to a surface of the subject at the insertion site (The desired angle may be, for example, approximately perpendicular or a non-perpendicular angle suitable for the insertion protocol. In some non-limiting example cases the non-perpendicular angle is 60° or less or 40° or less from perpendicular—the desired angle will depend on the site at which portal 20 is being introduced.) to the surface of the bone into which bone portal 20 is to be inserted; and
  pushing handle 14 in direction 13.

Force-limiting coupling 16 transmits force from handle 14 to driving member 12. The transmitted force is sufficient to push bone-penetrating portion 21 through the soft tissue T overlying the subject's bone B. The transmitted force is also sufficient to drive bone-penetrating portion 21 into the subject's bone B and to force bone stop 22 through the overlying soft tissues T.

Force-limiting coupling 16 prevents the force applied to driving member 12 from being large enough to drive bone stop 22 into the subject's bone. Therefore, application of tool 10 can reliably introduce portal 20 into the bone without the risk of over-penetration. The length of bone-penetrating portion 21 is chosen to permit the delivery of fluids and the like into the marrow space of the subject's bone. After it has been inserted, bone-penetrating portion 21 extends to a desired depth below the surface of bone B at which bone stop 22 stops. Bone stop 22 has a surface area sufficient to prevent it from penetrating bone B under a maximum force exerted by force-limiting coupling 16. The desired depth can vary depending upon the location which portal 20 is being introduced and the age of the subject. Bone penetrating portion 21 typically projects into the bone by several millimeters when it is fully inserted. Bone portal 20 defines a passage through which fluids can be infused into the bone marrow or, in the alternative, drawn out of the bone marrow.

The force required to drive the bone-penetrating portion of a portal into a subject's bone will depend on a range of factors including the dimensions and configuration of the driving member, the dimensions and configuration of the bone-penetrating portion of the portal, the dimensions of the bone stop of the portal that passes through the subject's soft tissues, the characteristics of the subject's bone at the insertion site, and the thickness of tissue overlying the insertion site. In some example embodiments force-limiting mechanism 16 transmits a force of up to at least 20 pounds force. In some example embodiments force-limiting mechanism 16 transmits a force of up to at least 30 pounds force (approximately 135 Newtons).

The length of bone-penetrating portion 21 of portal 20 may be tailored for the intended site of insertion and for the intended subject. Some bones have thicker cortical layers than others. For example, a portal designed for insertion into the tibia of an adult human may have a bone-penetrating portion that is somewhat longer than that of a portal designed for insertion into the sternum of an adult human. The cortical layer of bone tends to be thicker at the tibial site than it is in the sternum site in typical subjects. The bone-penetrating portions in bone portals intended for use in pediatric subjects may be shorter than the bone-penetrating portions in similar portals for use in adult subjects since the bones in infants are smaller than they are in adults.

In addition to the basic elements described above, the illustrated introducer tool 10 comprises a base 17 that can be brought to bear against the surface of the subject's skin S. A guide 18 is attached to base 17 so that, when base 17 is engaged against the subject's skin S, introducer tool 10, and in particular driving member 12 and bone portal 20 are held at a desired angle relative to the subject's bone B.

Base 17 may be connected to force-limiting coupling 16 by guide 18 or some other structure such that any force applied to handle 14 over and above the force at which force-limiting coupling 16 limits the force transmitted to portal 20 is distributed over base 17. Guide 18 may for example be a shield, sheath, guard and the like. Base 17 may optionally comprise an adhesive that may be used to hold base 17 in place on a subject's skin.

In the illustrated embodiment, bone portal 20 is connected to a fitting 24 by a tube 25. Fitting 24 may comprise, for example, a standard Luer fitting. Tube 25 is preferably a flexible tube. Tube 25 preferably connects to portal 20 at a location that is close to bone stop 22 so that the point of connection of flexible tube 25 to portal 20 is below the surface S of the subject's skin when bone portal 20 is inserted into bone B. That is, a distance between bone stop 22, which is at the surface of the subject's bone when bone portal 20 has been fully inserted, is spaced apart from the point at which tube 25 is flexible by a distance that is smaller than the expected depth soft tissue T overlying bone B. The thickness of overlying tissue varies significantly with factors such as the subject's sex, age, size and level of obesity as well as the site in question. For example, where the bone B is a subject's sternum, the overlying tissues may have a depth in the range of about 4 mm to 25 mm or so.

Advantageously, in some embodiments, the connection between bone portal 20 and tube 25 occurs at a distance of 5 mm or less, preferably 4 mm or less from bone stop 22. In such embodiments, the connection between bone portal 20 and tube 25 will typically be at a subcutaneous location after insertion of the bone portal 20.

In the illustrated embodiment, driving member 12 comprises a stylet 19 having a pointed tip 19A that projects through a longitudinal bore 26 in bone portal 20. A shoulder 27 or the like on stylet 12 may engage bone portal 20 to permit bone portal 20 to be pushed into the subject's bone B by introducer tool 10. Some example stylet configurations are described below.

Stylet 19 may have any suitable configuration. In some embodiments tip 19A of stylet 19 is conical or generally conical. In some such embodiments stylet 19 has a faceted tip. When the tip of the stylet is faceted, the number of facets on the tip of the stylet may be varied. For example, the stylet may have two, three, four, or more facets.

In preferred embodiments, the tip of the stylet forms an angle or angles in the range of 10-15 degrees with the center line of the stylet.

Force-limiting coupling 16 may comprise any of a variety of structures that allow force on handle 14 to be transmitted to driving member 12 but which limit that force to not exceed a maximum amount when introducer tool 10 is being used to introduce a portal 20. For example, force-limiting coupling 16 may comprise;
- a spring, for example a compression spring or an extension spring;
- a elastomeric or other resilient force transmission member which undergoes deformation in response to applied forces;
- a gas cartridge, bladder, or other pneumatic force-limiting assembly;
- a fluid-filled chamber fitted with a pressure-relief valve; or the like.

FIGS. 2A to 2L show a portal introducer tool 10A according to a more specific example embodiment of the invention. In introducer tool 10A, handle 114 is connected to a stylet 112 by a coil spring 116. Stylet 112 carries a bone portal 113.

In the illustrated embodiment, handle 114 has a blind inner cavity 115. One end of spring 116 bears against an end 115A of cavity 115. A second end of spring 116 bears against a shoulder 130 on a stylet support member 131. Stylet support member 131 is confined within cavity 115 by a retainer 132 but is free to slide within cavity 115 toward end 115A against the force exerted by spring 116.

Handle 114 is dimensioned such that proximal end 133 of handle 114 contacts base 117 before spring 116 is fully compressed and before stylet support member 131 can contact end 115A of cavity 115. This is illustrated in FIG. 2J.

In some embodiments, the travel of handle 114 is limited to a distance which is sufficient to drive a bone portal into a subject's bone in all expected circumstances. This travel should ideally be somewhat more than the expected maximum thickness of soft tissues T overlying the bone B into which the portal is to be introduced. In some embodiments the travel is about 20 mm or 25 mm or more. In other embodiments the travel may be greater than or less than this amount. Although it is typically not necessary, an embodiment could be made in which the travel is adjustable. For example, a moveable or replaceable stop could be provided on base 117. The stop may be located to engage end 133 at the end of the travel.

The maximum force applied to stylet 112 is determined by the force exerted by spring 116 on stylet support member 131 when handle 114 is pressed in until end 133 contacts base 117. Any additional force exerted on handle 114 will merely press base 117 against the skin S of a subject. Since base 117 can have a relatively large surface area, the pressure exerted by base 117 against the subject is not excessive under any ordinary circumstances.

Spring 116 is sized to provide sufficient force to insert bone portal 20 in subjects having a range of bone hardness and overlying-tissue thickness, including the thickest expected overlying tissue and the toughest expected bone. On the other hand, the force is limited such that it is not likely to drive the bone stop on a bone portal through the cortical layer of bone of a subject, including a subject having the thinnest expected overlying tissue and the softest expected bone.

The concept of providing an introducer tool comprising a force-limiting coupling is not limited to contexts in which a bone stop is provided on a bone portal although it is especially advantageous in such contexts. The concept could also be applied to introducer tools in which other bone stops are provided. For example, the concept could be applied in an introducer tool having one or more needle-like bone stops near to or surrounding a stylet. Some examples of such arrangements of bone stop are described in U.S. Pat. No. 6,761,726 and discussed below.

In the illustrated embodiment, base 117 has adhesive 139 on its face 140 that bears against a subject's skin S. This permits base 117 to be stuck to the subject's skin over the location at which it is desired to insert a bone portal. Introducer tool 10A may be detached from base 117 after the bone portal has been inserted. Base 117 may remain adhered to the subject for use as a strain relief and/or to protect the site at which the portal has been introduced.

An audible or tactile click or other indication may be provided when handle 114 has reached, or almost reached, contact with base 117. This provides audible and/or tactile feedback that the downward travel required to introduce a bone portal has been completed. The indication may be provided by a detent or other suitable mechanism, for example, operable in response to the motion of stylet support member 131 relative to the handle 117.

After the bone portal has been inserted, handle 114 may be removed from base 117 by pulling in direction 148. The adhesive 139 between base 117 and the subject's skin holds base 117 in place while handle 114 is pulled away. Additionally, a user may hold base 117 down by placing the user's fingers on the parts of base 117 that project outwardly from handle 114.

FIGS. 2N through 2P show an example of a detachable coupling 144 that may be provided between base 117 and shield 145. Coupling 144 comprises projections or recesses 144A on shield 145 that are biased to engage with corresponding recesses or projections 144B on a wall 144C projecting from base 117.

As shown in FIG. 2B, base 117 includes strain relief fittings 142. An infusion tube may be coupled to one or more strain relief fittings 142 so that any tension applied to the infusion tube will be transmitted to base 117 and will not pull on the implanted bone portal. In the illustrated embodiment, the strain relief fittings 142 are provided by an upwardly-projecting wall 141 having notches 143 dimensioned to receive a strain relief member that projects from tubing that is either directly or indirectly coupled to an implanted bone portal. Alternative strain relief fittings such as tube clamps of any suitable kind, hook(s) that engage a loop on an infusion tube assembly, loop(s) that engage a hook on an infusion tube assembly or the like may be provided.

Introducer tool 10A has a shield 145 that is received telescopically within stylet support member 131. Shield 145 surrounds the projecting portion of stylet 112. Shield 145 may have multiple functions. On one hand, shield 145 may shield stylet 112 from view prior to and while a bone portal is being inserted. Some subjects, or persons accompanying the subjects may be uncomfortable at the sight of a bone portal. To provide this function, shield 145 should be opaque or translucent.

A second function of shield 145 may be to prevent needle stick injuries by the sharp end of stylet 112 after introducer tool 10A has been used to insert a bone portal and has been removed from base 117. In the illustrated embodiment, a distal end 145A of shield 145 is initially detachably coupled to base 117. The proximal end 145B of shield 145 is received within stylet support member 131 and slides relative to stylet support member 131 while a bone portal is being inserted. It is not mandatory that shield 145 be free from apertures.

A third function of shield 145 in the illustrated embodiment is to support handle 114 and stylet support member 131 so that the stylet will be held in a desired orientation relative to the subject. In the illustrated embodiment, distal end 145A of shield 145 is flared and bears against base 117; this, in combination with the engagement of wall 144C inside shield 145 holds shield 145 at the desired angle to base 117. In the illustrated embodiment, shield 145 has external splines 145C which slide between internal splines 131A of stylet support member 131. Splines 145C stiffen shield 145 and preserve the orientation of handle 114, shield 145 and base 117.

In the illustrated embodiment, the detachable connection between distal end 145A of shield 145 and base 117 is strong enough to pull distal end 145A outwardly relative to stylet support member 131. As this occurs, proximal end 145B is pulled toward the opening of stylet support member 131. When this occurs, proximal end 145B of shield 145 becomes locked in place relative to stylet support member 131 such that the sharp tip of stylet 112 is protected by shield 145 which is now locked in place and cannot be readily retracted. After shield 145 has been pulled to its fully-extended position by withdrawing handle 114, the distal end of shield 145 becomes disengaged from base 117 and handle 114 containing shield 145 and stylet 112 may be disposed of safely or processed for re-use. In alternative embodiments a spring or the like may be provided to urge shield 145 into an extended position after insertion of a bone portal.

Various alternative mechanisms may be supplied for holding shield 145 in place once it has been pulled to its extended position. For example, a ratchet mechanism or the like may be supplied between shield 145 and stylet support member 131. In the illustrated embodiment, teeth 146A engage recesses 146B when shield 145 is fully extended (See FIG. 2I in which teeth 146A are engaged in recesses 146B). A locking mechanism which prevents shield 145 from being retracted after it has been fully extended may optionally be provided.

Stylet 112 is typically long and relatively thin in cross-section. Consequently, in some embodiments, means are provided to prevent buckling of stylet 112 during insertion of a bone portal. These means may include, for example, one or more spacers which fit between stylet 112 and the bore 134 of stylet support member 131 and/or the inside of shield 145. The spacers are free to slide within bore 134 to permit removal of handle 114 from the implanted bone portal and its associated tubing and fitting, if present. A spacer 149 having a circumferential groove 149A is shown.

In some embodiments, a support member such as fitting 124 is dimensioned to bear against the walls of bore 134 of stylet support member 131 and to therefore support stylet 112. In these and other embodiments, additional support members (such as spacers 149 for example) may be provided between tube 125 and the walls of the bore of stylet support member 131. Additional support members may comprise: a part of tube 125, an expanded member that is slidable on tube 125, or an expanded member that is affixed at a location on tube 125 or confined to slide on a section of tube 125.

In some embodiments, the expanded member is dimensioned to be received in notches 143 or other strain relief fittings 142 so that the expanded portion serves double purpose as a strain relief member and as a support that assists in preventing stylet 112 from buckling under the forces exerted on stylet 112 during the insertion of a bone portal. Support member 149 may be attached to a tube 125, for example and groove 149A may be dimensioned to allow support member 149 to snap into one of notches 143.

In some embodiments, an additional guide for stylet 112 is provided on base 117. For example, as shown in FIG. 2K, base 117 may comprise a central opening 147 to receive the tip of stylet 112. Opening 147 may be a close fit to the outside of tube 125. The opening may be tapered or otherwise shaped to guide stylet 112 and the associated bone portal and tube 125 during insertion of the bone portal so that the bone portal is inserted in a linear motion. The close engagement between the sides of opening 147 and the outside of tube 125 helps to centralize and further support stylet 112 during introduction of a bone portal.

Another benefit of having opening 147 a relatively close fit to the outer diameter of tube 125 is that there is very little room for any dirt to enter between the tube and the base. This helps to keep the insertion site clean and to protect the tissues at the insertion site from contact with foreign objects.

FIGS. 3A to 3M show an introducer tool 10B according to another embodiment of the invention. Introducer tool 10B is similar to the introducer tool of FIGS. 2A to 2L with the main exception that a different mechanism is provided to guide the motion of spring 116 and a shield is located outside of spring 116 instead of inside of spring 116 as in the introducer tool 10A described above.

Figures 3A, 3B:
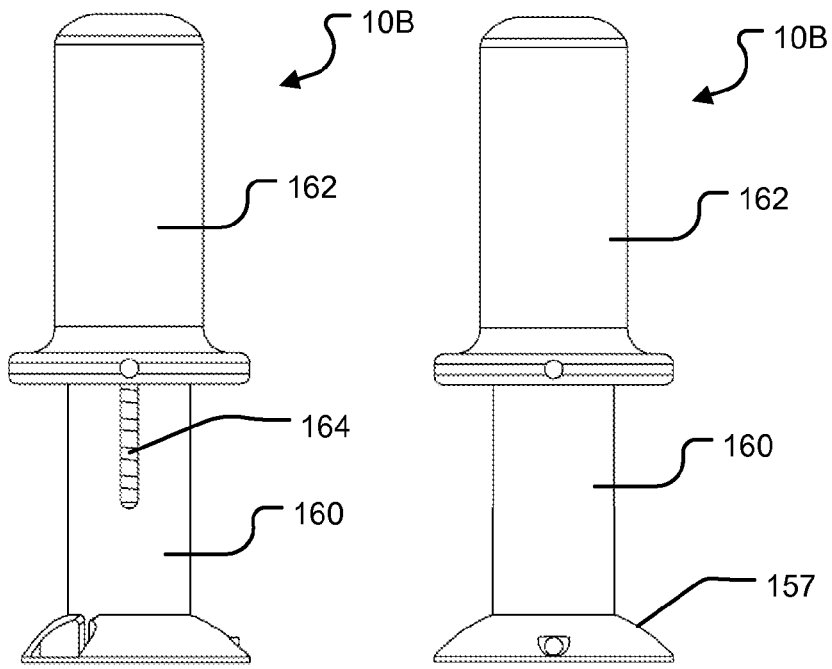
Figures 3C, 3E:
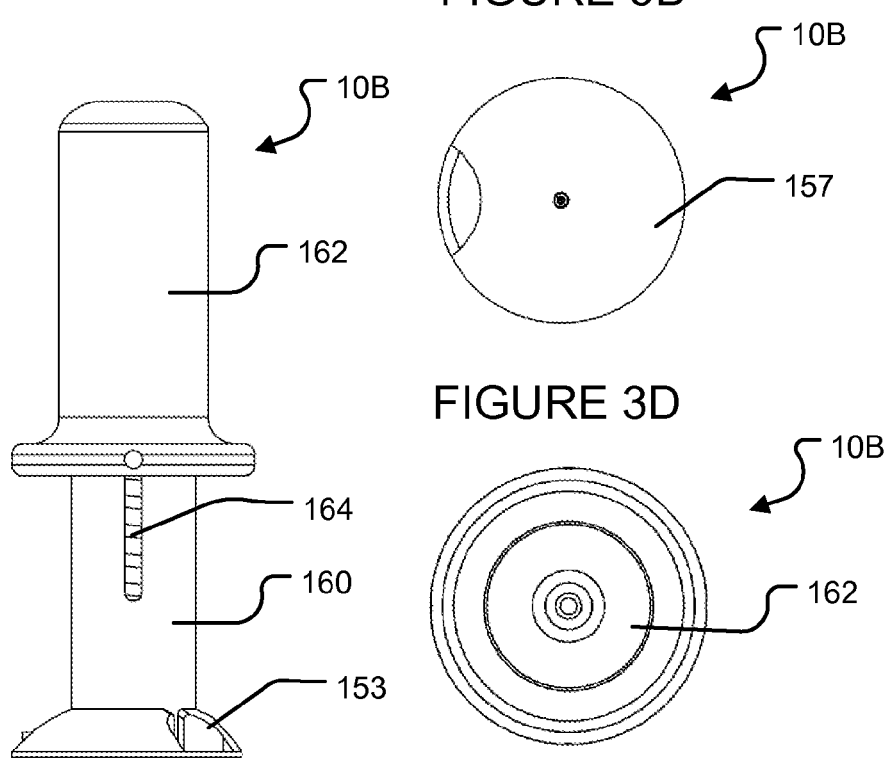
Figures 3F, 3G:
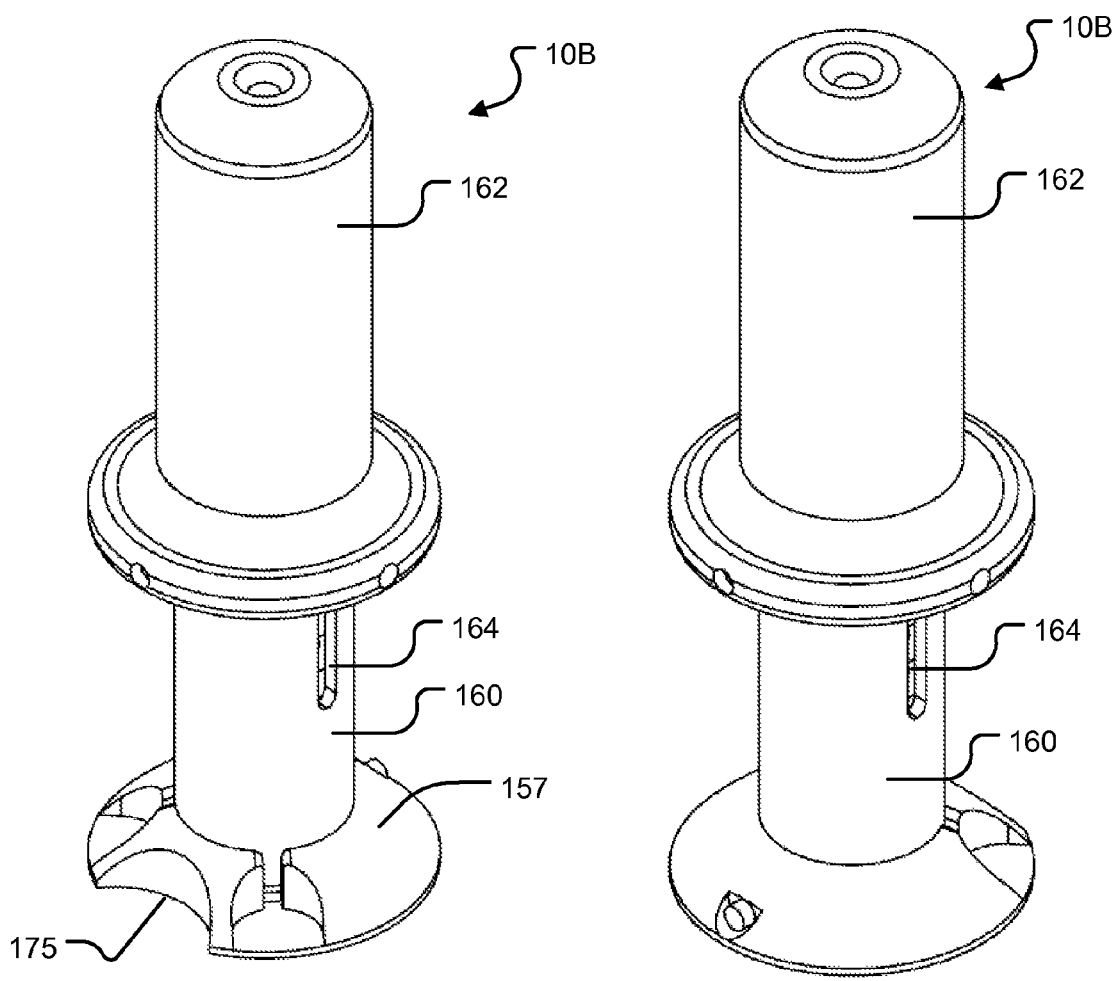
FIGS. 3F and 3G are isometric views of the introducer tool.
Figure 3H:
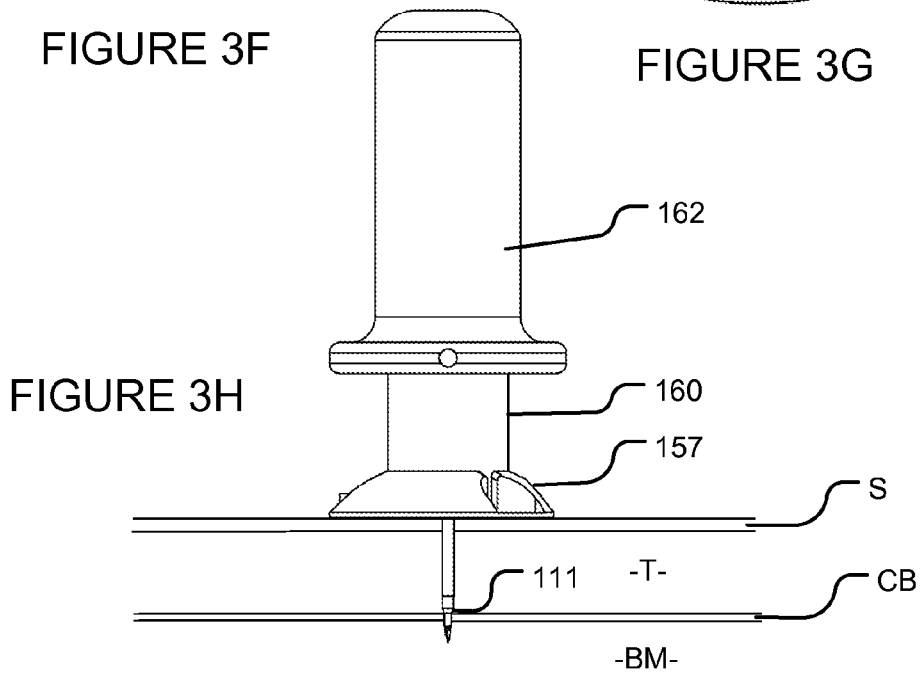
FIG. 3H is a side view of the introducer tool in an extended configuration.
Figure 3L:
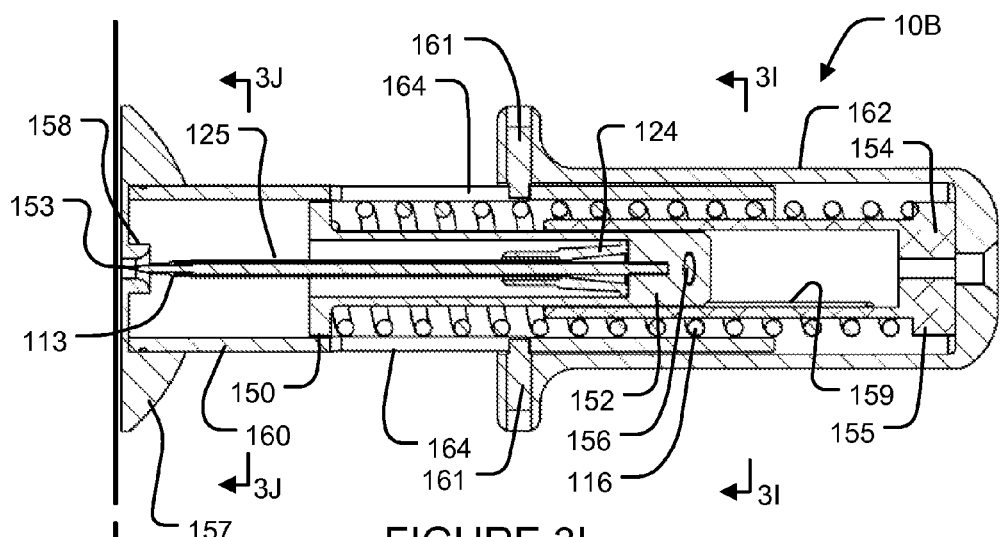

Introducer tool 10B confines a spring 116 between a stylet support member 152 and a spring retaining member 154 (See FIG. 3L). Spring retaining member 154 is attached to handle 162. In the illustrated embodiment, the fastening is provided by a screw or other fastener. However, spring retaining member 154 could be integral with handle 162 or affixed in some other way to handle 162.

Spring 116 is compressed between a flange 150 on stylet support member 152 and a flange 155 on spring retaining member 154. Stylet support member 152 and spring retaining member 154 can telescope relative to one another. A pin 156 extends through one end of stylet support member 152 into longitudinal grooves 159 in spring support member 154. Pin 156 keeps the assembly of spring 116, and members 152 and 154 together.

The spring assembly comprising spring 116 and members 152 and 154 is received within a shield 160 that is slidably coupled to handle 162. In the illustrated embodiment, shield 160 is held to handle 162 by means of pins 161 which engage longitudinal slots 164. The slots permit handle 162 to be moved toward base 157 through a limited range of motion sufficient to insert bone portal 113 into a subject. The force is delivered from handle 162 to stylet 153 by way of spring 116. This limits the amount of force delivered to stylet 153 and also ensures that the amount of force on stylet 153 is constant as long as sufficient pressure is exerted on handle 162.

Figure 3M:
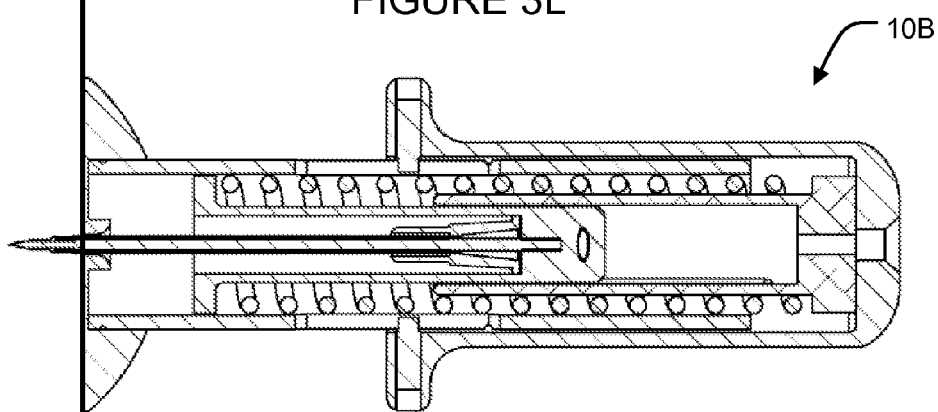
Figure 3N:
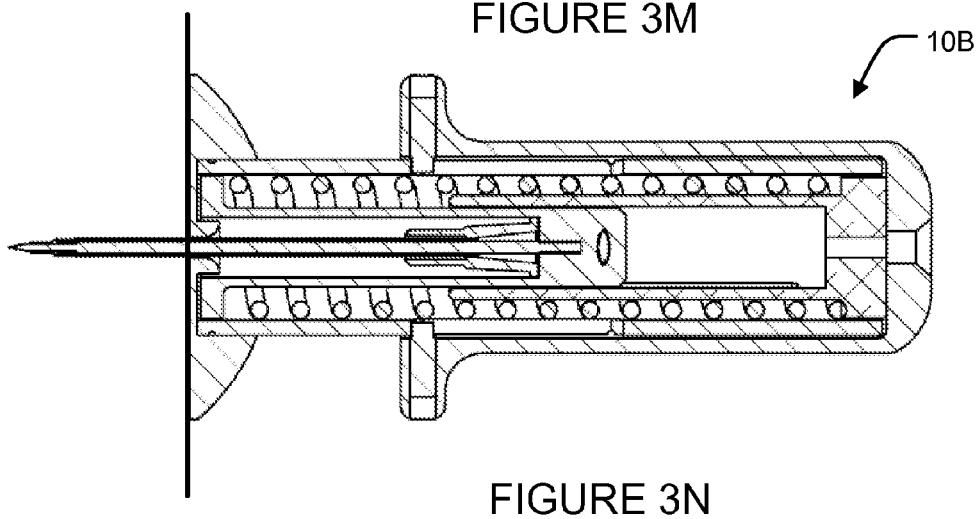
Figure 4A:
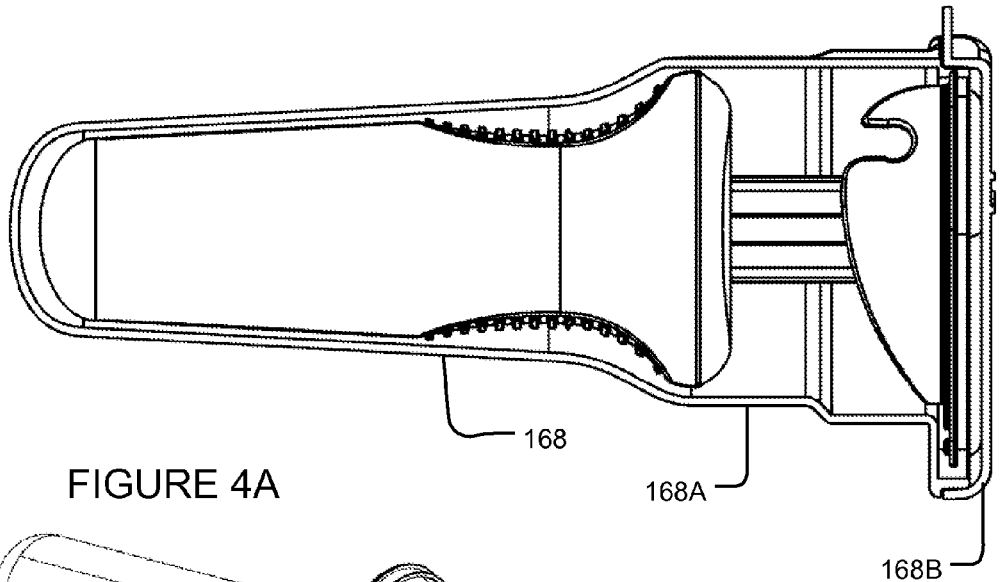
FIGS. 4A to 4E show an introducer tool in a sterile enclosure.
Figure 4B:
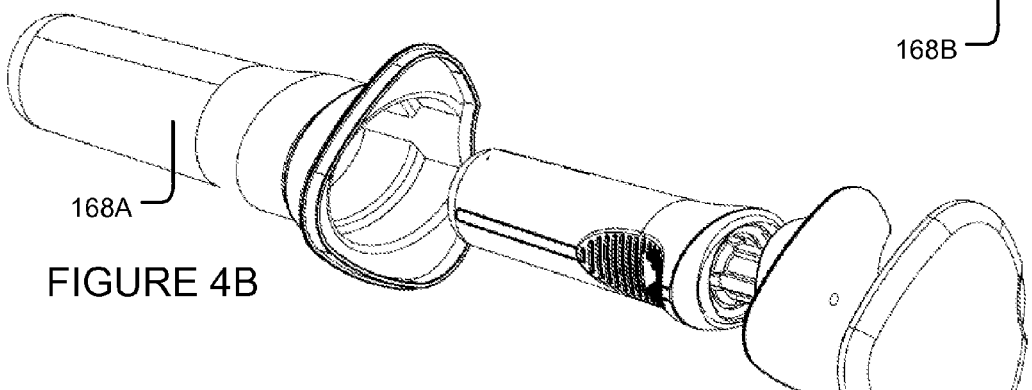
Figures 4C, 4D, 4E:
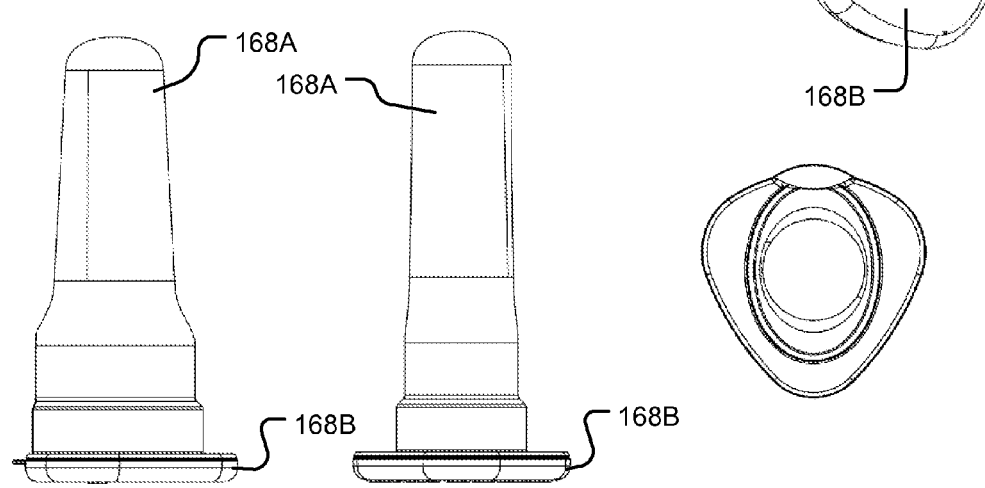

FIGS. 3L through 3N respectively show introducer tool 10B in its initial configuration, in a partially-extended configuration, and in a fully-extended configuration. In the fully-extended configuration pins 161 bear against the proximal ends of slots 164. Any additional pressure on handle 162 merely applies force to base 157 and does not cause further projection of stylet 153 from the lower side of base 157.

After a bone portal 113 has been implanted, when it is desired to remove introducer tool 10B, handle 162 is pulled away from base 157. As this occurs, spring retaining member 154 together with spring 116, stylet support member 152 and stylet 153 are all pulled away from base 157 up into shield 160. A ratchet mechanism or other means (not shown) may be provided to keep stylet 153 retained within shield 160 after it has been fully retracted into shield 160 by pulling upwardly on handle 162. With enough pull, shield 160 detaches from base 157. Introducer tool 10B can then be discarded or sent to be prepared for re-use. Base 157 may remain adherent to the subject's skin to protect the insertion site, and act as a strain relief.

Introducer tools 10A and 10B may be used in similar ways to introduce bone portals. A method of using introducer tool 10B to insert a bone portal according to an example embodiment of the invention is described next.

Introducer tool 10B is removed from its sterile covering and adhesive beneath base 117 is exposed by peeling off a release sheet. Introducer tool 10B is brought to a desired location over the bone of a subject. To assist in positioning introducer tool 10B, base 157 may be equipped with guide features which may be aligned with anatomical features of the subject. For example, base 157 may have an open-sided recess 175 (shown in FIG. 3J) or an aperture to be aligned over an anatomical landmark and/or one or more arrows or other marked indicia arranged to indicate a desired alignment of base 157 with one or more anatomical landmarks. A person using introducer tool 10B can engage a finger with recess 175 and position introducer tool 10B so that the finger that is engaging recess 175 can feel the sternal notch of the subject, to position tool 10B just below the sternal notch. The user can then press base 157 against the subject's skin so that base 157 is adhered in place over the subject's sternum.

When base 157 is positioned over a target location the user can press down on handle 162. In doing so, spring retaining member 154 and spring 116 are pushed downward, which in turn causes stylet 153 to be pushed downward, penetrating through the subject's skin S and tissue T carrying with it bone portal 113. As shown in FIG. 3H, stylet 153 penetrates the cortical bone CB and carries bone portal 113 such that the bone-penetrating part of bone portal 113 extends into the bone marrow BM. As the user continues to push on handle 162, stylet 153 forces bone portal 113 through the subject's tissues T until the flared bone stop 111 of bone portal 113 lodges against the cortical bone CB of the subject's bone, preventing bone portal 113 from being pushed completely through the cortical bone CB into the bone marrow BM. At this point, the force which spring 116 permits to be delivered to stylet 153 is too small to move bone portal 113 further into the bone. Any additional force exerted by the user on handle 162 is, due to the bottoming out of pins 161 in longitudinal slots 164, carried through shield 160 to base 157 where it compresses the subject's tissues T slightly without causing portal 113 to advance significantly further into the subject's bone.

A guide 158 (shown in FIG. 3K) on base 157 centers and prevents buckling of stylet 153 so that it enters straight into the subject's tissues T. It can be appreciated that in embodiments described above wherein the base is attached to the introducer tool, the base provides a stable platform for inserting a bone portal and can aid greatly in maintaining proper alignment perpendicular to the bone into which the portal should be introduced. The base may be mounted at a desired angle other than perpendicular to the stylet to facilitate guiding introduction of a bone portal at a desired non-perpendicular angle. Having a base integral with an introducer tool advantageously reduces the number of separate parts that are required to introduce a bone portal.

The base may be made of a stiff material, such as plastic, to assist in firmly supporting the introducer tool at the desired angle relative to the subject's skin and also to transfer any excessive forces to a reasonably large area of the subject's skin during insertion. The base is not necessarily rigid although it is quite stiff in some embodiments. The base may have some or even a significant degree of flexibility in some embodiments.

In some embodiments the base has some parts that are more rigid than others. For example, a base suitable for use with an introducer tool may have a more-rigid part and a less-rigid part. The less-rigid part may optionally be initially curled up or folded so that the introducer tool can be provided in a more compact package. The less-rigid part can then be unrolled or folded out during deployment of the introducer tool. In some embodiments, the base, or a portion of the base, comprises a moldable material that can be formed to match contours of the subject's body over or around the desired insertion site.

Bone portal 113 can thereby be fully inserted into the subject's bone B with the bone stop lodged against the cortical bone CB of the subject's bone.

After bone portal 113 has been introduced, handle 162 is pulled away from the subject. This lifts stylet 153 upwards out of bone portal 113 and out of infusion tube 125 that is connected to bone portal 113. Stylet 153 is pulled back until the tip of stylet 153 is protected within shield 160, limiting exposure of the tip of stylet 153 to needle stick injury.

Continued pulling on handle 162 disengages shield 160 from base 157. The user may use one hand to hold the base 157 down while the other hand is used to firmly pull handle 162 and shield 160 from base 157. In some embodiments, as discussed below, base 157 may be coupled to shield 160 by a mechanism which automatically uncouples base 117 from shield 160 upon use to implant a bone portal. Introducer tool 10B may then be discarded or processed for re-use. Infusion tube 125 extending from the now implanted bone portal 113 may be clipped to strain relief fittings on base 157 as described above. Fluids may be delivered to the subject or withdrawn from the subject by way of infusion tube 125 (e.g. a Luer fitting on infusion tube 125 may be fitted to a standard IV connector).

The application of the apparatus described above is not limited to inserting a bone portal into a subject's sternum. Introducer tools 10A and 10B have some features that are particularly advantageous for use on the subject's sternum. These advantageous features include:

- It is particularly desirable to avoid over-penetration of the sternum; the combination of a portal having a bone stop with a force-limiting coupling prevents over-penetration.
- The limited travel of the handle of the introducer tools described above relative to the base limits the maximum depth to which a stylet can enter a subject. This is a safety feature.
- Base 157 has a guide feature (recess or indentation in these embodiments) along one edge thereof that is useful for aligning base 157 over an insertion site in a subject's sternum. The guide feature may, for example, be complementary in size to a sternal notch so that the base can be positioned by aligning the guide feature with the subject's sternal notch. The distance separating the guide feature in the base and the point which the stylet will enter the subject is an appropriate distance for obtaining proper insertion of a bone portal into the subject's sternum.

FIGS. 4A to 4E show that an introducer tool may be conveniently packed in an enclosure 168. Enclosure 168 may maintain sterility of the packed introducer tool and may also keep the introducer tool conveniently together with associated supplies such as swabs or wipes that may be desirable to have during use of the introducer tool. In the embodiment illustrated in FIGS. 4A to 4E, the introducer tool is like the introducer tool 10A described above. Enclosure 168 in the illustrated embodiment has a first part 168A that covers a handle of the introducer tool and a second part 168B that covers the base of the introducer tool. In some embodiments, removing second part 168B automatically exposes an adhesive on the base. In other embodiments, removing second part 168B exposes one or more release sheets which can be peeled off to expose an adhesive on the base. A sterile bone portal equipped with an infusion tube and a suitable fitting may be pre-loaded onto the introducer tool.

In some embodiments, a sterile swab, sponge wipe or the like, which may be impregnated with a cleaning agent, which may comprise a biocide, is provided inside sterile enclosure 168. In such embodiments, a user may open enclosure 168, swab the subject's skin at the intended insertion site with the swab, and then use the introducer tool to insert a bone portal into the subject's bone at the insertion site.

Figures 5F, 5G:
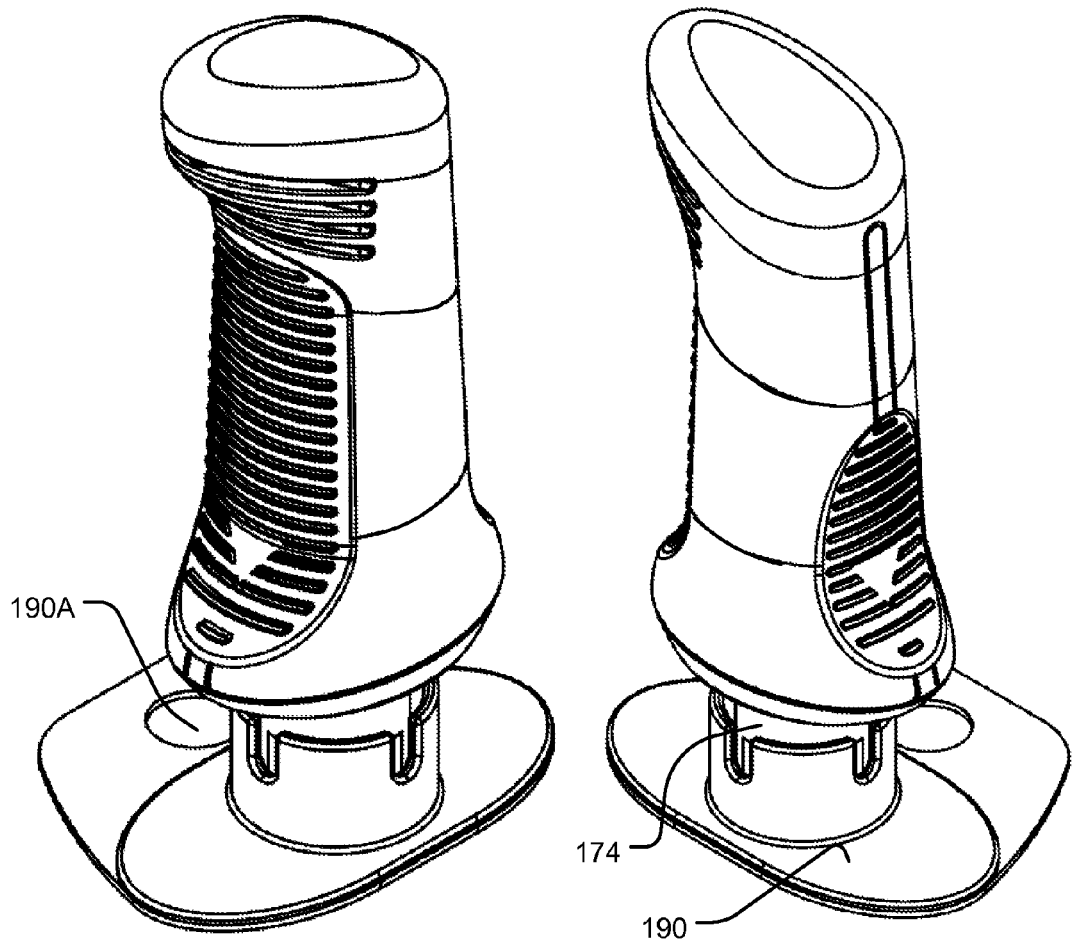
FIGS. 5F and 5G are isometric views of the introducer tool.
Figure 5H:
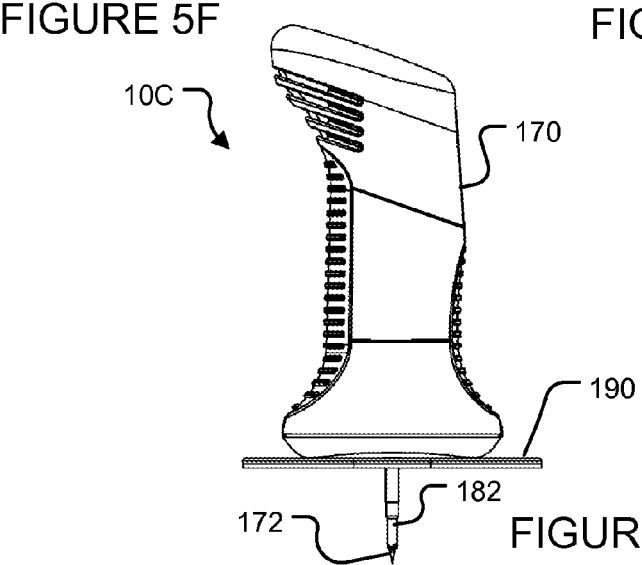
FIG. 5H is a side view of the introducer tool in an extended configuration.
Figure 5I:
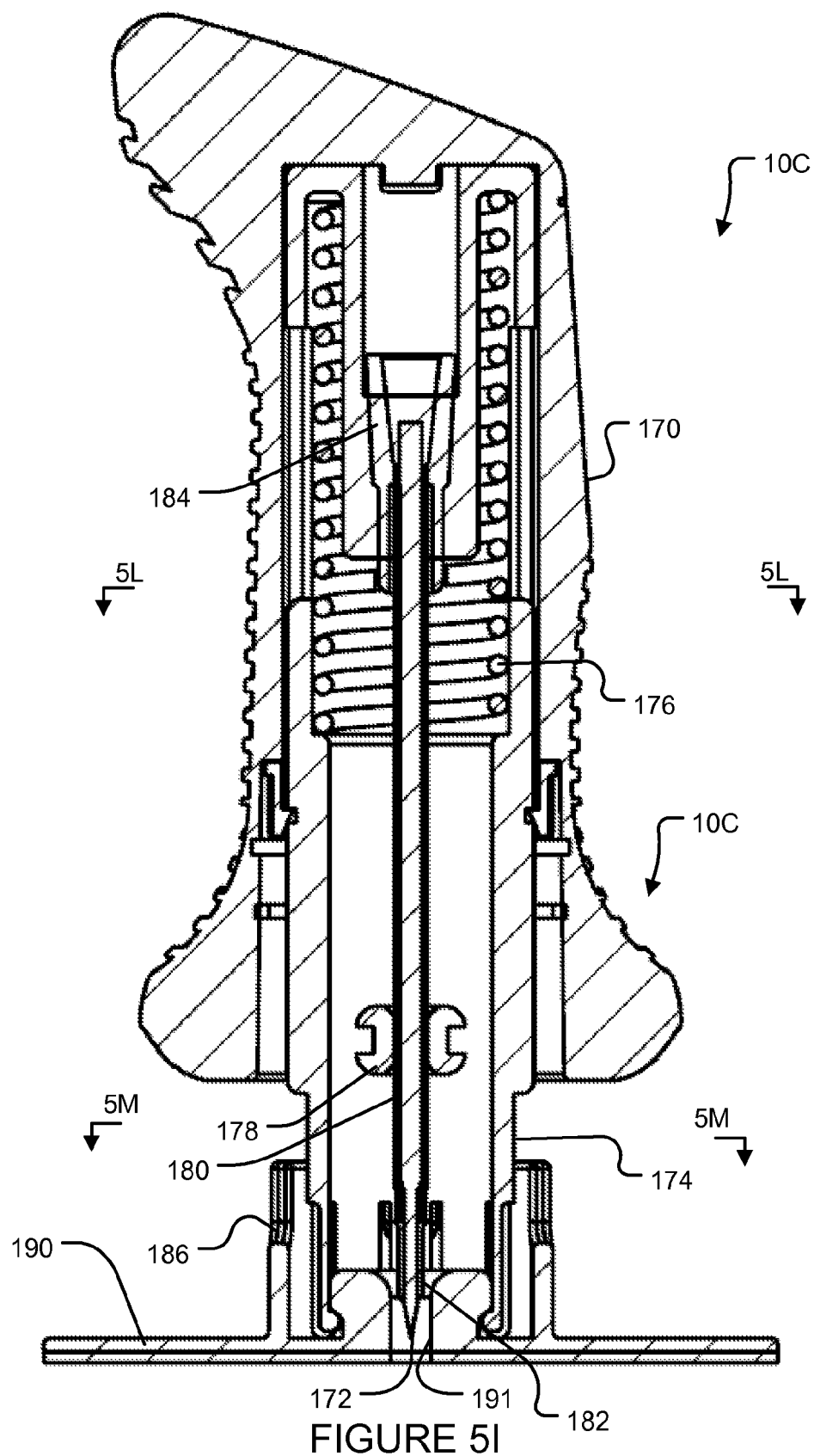
FIG. 5I is a cross-sectional side elevation view of the introducer tool.
Figures 5J, 5K, 5L, 5M:
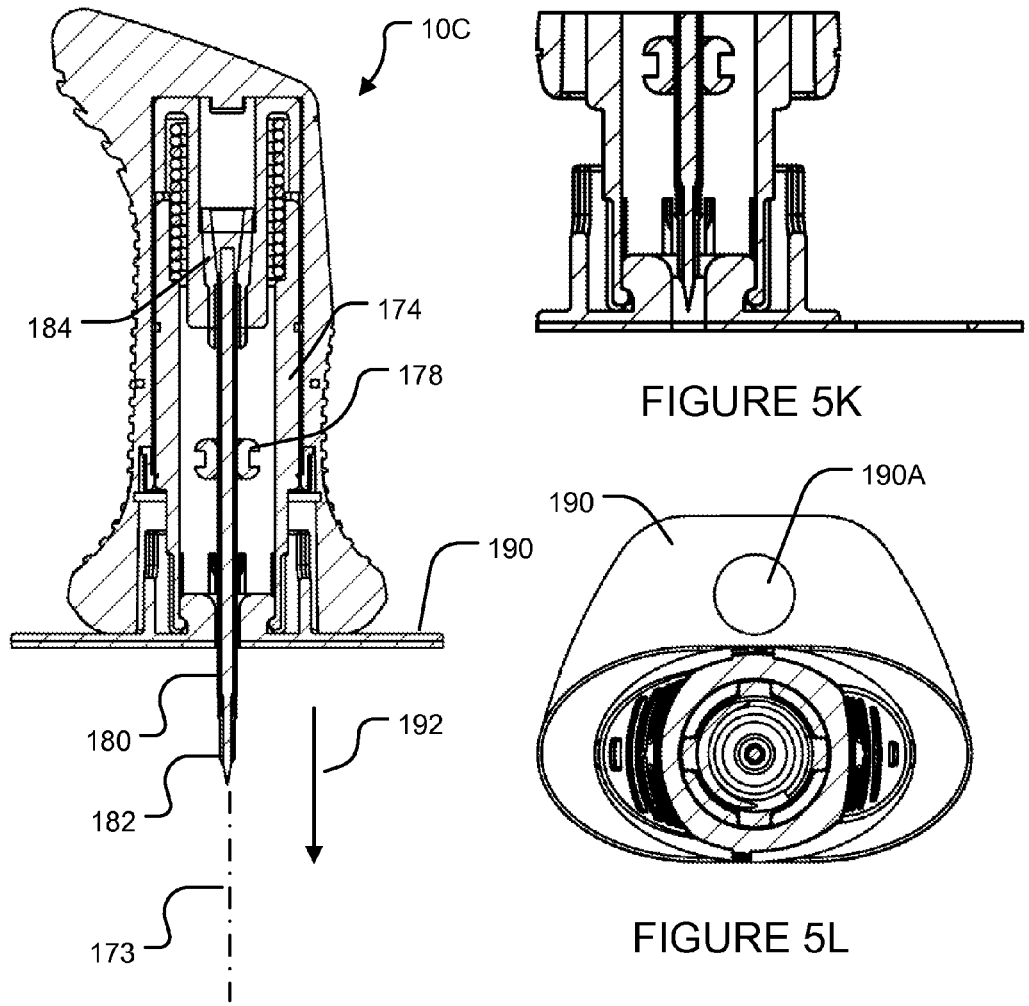
FIG. 5J, is a cross-sectional side elevation view of the introducer tool in an extended configuration.
FIG. 5K is a detail cross-sectional view showing stylet guides in a base.
FIGS. 5L and 5M are respectively cross-sectional views in the planes 5L-5L and 5M-5M shown in FIG. 5I.

FIGS. 5A to 5Q illustrate an introducer tool 10C according to another embodiment. Introducer tool 10C has a number of features in common with the introducer tools described above. One difference between introducer tool 10C and the introducer tools described above is that introducer tool 10C has a handle 170 that is coupled directly to a stylet 172 which carries a bone portal 113 during insertion of the bone portal. In this embodiment, forces exerted on handle 170 are transmitted directly to stylet 172 and any bone portal being carried on stylet 172. This can be advantageous in cases where the bone into a which a bone portal is being introduced has a hard, thick, or otherwise difficult-to-penetrate cortical layer.

Introducer tool 10C comprises a shield 174 which surrounds stylet 172. Shield 174 is spring loaded by a spring 176 which pushes shield 174 into an extended position wherein it covers up the sharp tip of stylet of 172. A user can press handle 170 toward the body of a subject, thereby compressing spring 176 and allowing shield 174 to retract so that the stylet 172 can penetrate the subject's tissues and push a bone portal into an underlying bone.

In the illustrated embodiment, one or more spacers 178 are provided between stylet 172 (and the tube 180 that connects portal 182 to fitting 184). Spacers 178 help to prevent stylet 172 from buckling as forces are applied to it. Spacers 178 may remain captured on tube 180 after insertion of bone portal 182. In some embodiments, spacers 178 are affixed to tube 180 and are designed to engage with strain relief fittings 186 on base 190.

Some embodiments are adapted to permit a user to rotate stylet 172 generally about its longitudinal axis 173 by rotating handle 170 while applying force to stylet 172 in direction 192. In such embodiments, stylet 172 and/or portal 182 may be shaped so that their rotation aid opening up a passage through the cortical layer of bone into which the portal is to be inserted. The application of such stylets and bone portals is not limited to introducer tools in which rotation is imparted by hand. Such stylets and bone portals could also be applied in embodiments in which a motor is provided to drive rotation of the stylets and/or bone portals.

Introducer tool 10C may be used by placing base 190 on the surface of a subject's skin so that hole 191 is located over a site on the subject's bone at which it is desired to implant bone portal 182. As above, an adhesive may be provided on base 190 for adhering base 190 to the subject's skin at the desired location. Base 190 is applied over the desired location and adhered in place.

Introducer tool 10C has a shape to facilitate alignment of a location at which a bone portal will be inserted with a desired location, for example, on a user's tibia, in which a bone portal can be best located. Graphics and/or configurational features on base 190 may be provided to help a user to properly position base 190 in the desired location. The graphics and/or configurational features may help the user to align a guide feature, as described above, on base 190 with the subject's tibial tuberosity.

In the illustrated embodiment, the hole 191 through which the stylet can be made to project is spaced apart from an aperture 190A in base 190. A user can properly locate base 190 so that bone portal 182 will be inserted at a desired site on the tibia by finding the subject's tibial tuberosity and placing the base 190 over the tibial tuberosity such that the tibial tuberosity can be felt by the user's fingers through aperture 190A.

Base 190 holds introducer tool 10C so that axis 173 is at a desired orientation relative to the bone. For example, axis 173 may advantageously be held so that it is essentially perpendicular to the surface of the bone at the intended point of insertion. In some embodiments, base 190 has a straight edge or other linear feature that can be aligned with an anatomical feature of a subject to achieve proper positioning of base 190 over a desired site for a portal.

The user then pushes down handle 170. Spring 176 becomes compressed and allows handle 170 to move toward base 190 until stylet 172 projects through hole 191 into the subject's tissues. The user continues to push handle 170 until the tip of the stylet is against the subject's bone. If it is necessary to do so to advance the tip of stylet 172 and the bone-penetrating part of the portal, the user may rotate handle 170 about axis 173 to help to open a path for the insertion of the portal into the subject's bone.

Different geometries of stylet and portal which facilitate penetration of a bone portal by rotation of the bone portal and stylet during introduction are described below. In some embodiments, the bone portal is coupled to the stylet with a ratchet mechanism which, upon a user turning handle 170 clockwise and counterclockwise about axis 173 in alternation, causes the portal to turn only clockwise or only counterclockwise in response to the rotation. In other embodiments, the stylet is coupled to handle 170 by a ratchet mechanism which causes the stylet and bone portal to rotate in one direction upon rotation of handle 170. In some embodiments the portal is keyed to the stylet so that it rotates together with the stylet.

After the user feels that the bone portal has penetrated into the bone, the user can withdraw handle 170. While doing so, the user preferably holds down base 190. Continued pull on handle 170 in the direction opposite to arrow 192 causes shield 174 to come out of engagement with base 190. Shield 174 continues to project so that it covers the sharp tip of stylet 172.

FIGS. 5N through 5Q illustrate a possible arrangement by which shield 174 may be detachably coupled to base 190 while permitting relative rotation of shield 174 and base 190. Projections 183A are on resilient tabs on shield 174. Projections 183A can engage a groove 183B on a boss projecting from base 190. Projections 183A can be pulled out of groove 183B if enough force is applied to pull handle 170 and shield 174 away from base 190.

After bone portal 182 has been inserted, an infusion tube 180 attached to portal 182 may be coupled to a strain relief fitting 186 on base 190 in order to prevent any tension applied the tube from dislodging the bone portal.

An advantage of introducer tool 10C is that it can be operated with one hand to insert a bone portal. This allows the user to stabilize the subject's body with his or her free hand. Providing a tool that can be operated with one hand is particularly beneficial when the bone into which the portal will be introduced is in a subject's limb. For example, where a portal is to be introduced into a subject's tibia, a user may wish to stabilize the subject's leg with one hand while using the other hand to insert the portal. An introducer tool which can be operated to introduce a portal using one hand facilitates this.

Figure 6A:
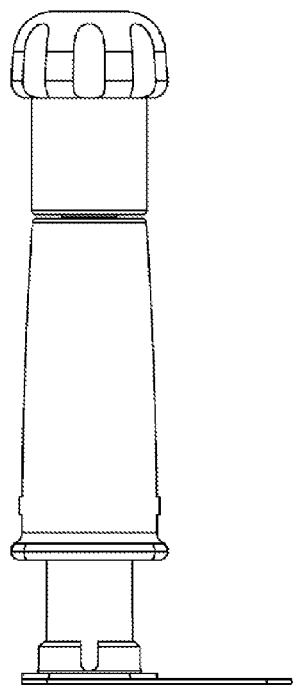
Figure 6B:
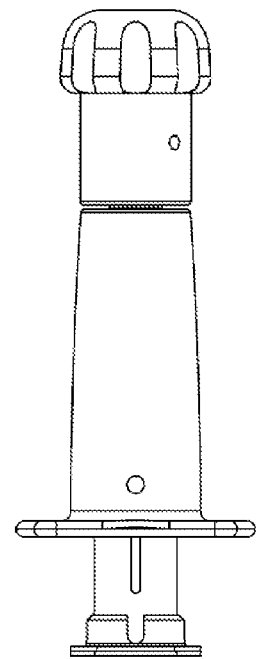
Figure 6C:
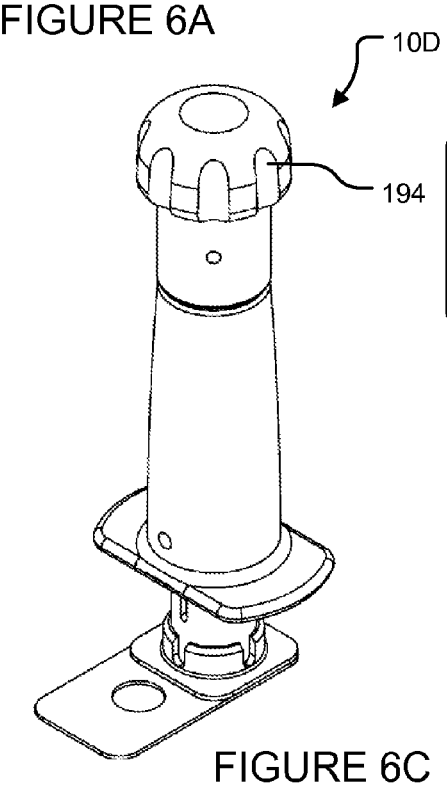
Figure 6D:
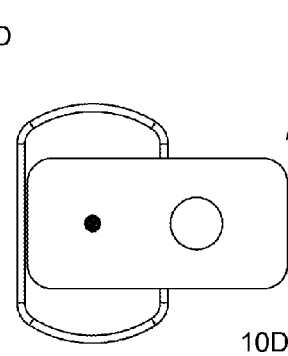
Figure 6E:
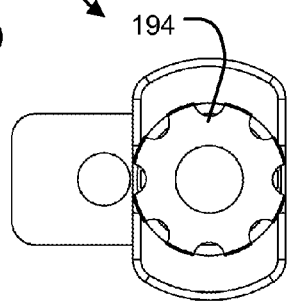
Figure 6K:
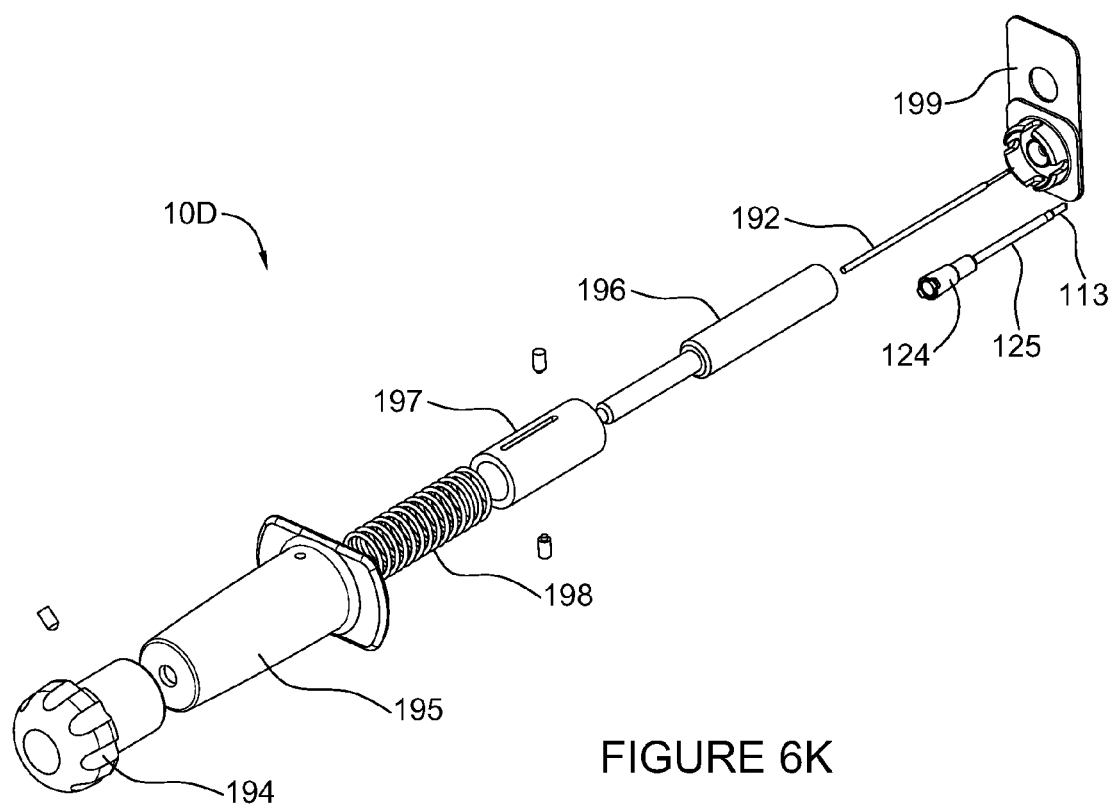
FIG. 6K is an exploded view of an introducer tool similar to that shown in FIGS. 6A to 6J.

FIGS. 6A to 6K show an introducer tool 10D according to another embodiment of the invention. FIG. 6K is an exploded view. Introducer tool 10D is similar to introducer tool 10C except that stylet 192 is coupled to be driven in rotation by a knob 194. In the illustrated embodiment, knob 194 is located at a distal end of handle 195. In the illustrated embodiment, stylet 192 is coupled to knob 194 by a stylet support member 196 which is disposed slidably within a shield 197. Knob 194 may be coupled to stylet 192 by a ratchet mechanism such that oscillating rotation of knob 194 results in uni-directional rotation of stylet 192. A spring 198 biases shield 197 so that it projects outwardly from handle 195. A distal end of shield 197 is detachably coupled to base 199. A method of using introducer tool 10D to insert bone portal 113 according to an example embodiment of the invention is described next.

Introducer tool 10D is removed from its sterile covering and adhesive beneath base 199 is exposed by peeling off a release sheet. Base 199 is aligned with anatomical features such that stylet 192 is positioned over the site on the subject's bone at which it is desired to introduce bone portal 113. Base 199 may comprise a transparent, die cut tab, for example. Similar to introducer tool 10C, graphics may be provided on base 199 to help a user to properly position base 199 in the desired location. The graphics and/or configurational features may help the user to align a guide feature on base 199 with the subject's tibial tuberosity, for example. A user may properly position base 199 so that bone portal 113 will be inserted at a desired site on the tibia (inside and medial of the tibial tuberosity) by finding the subject's tibial tuberosity and placing the base 199 over the tibial tuberosity such that the tibial tuberosity can be felt by the user's fingers through aperture 199A.

Base 199 is brought against the subject's skin. Base 199 holds shield 197 such that stylet 192 is generally perpendicular to the subject's bone. The user can then press handle 195 toward the subject's bone until stylet 192 contacts and begins to penetrate the bone. If it is necessary to do so in order to fully implant bone portal 113, the user can turn handle 194 about axis 193 while maintaining pressure on handle 195 (FIGS. 6F and 6G).

Figure 7A:
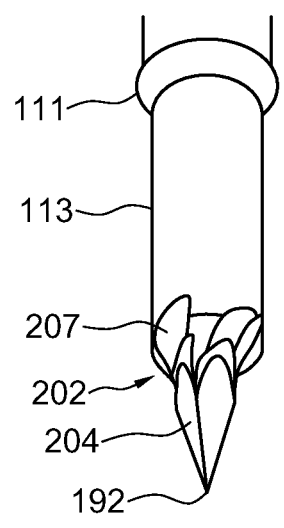
FIGS. 7A and 7B show a portal and stylet combination of the introducer tool of FIGS. 6A to 6K.
Figure 7B:
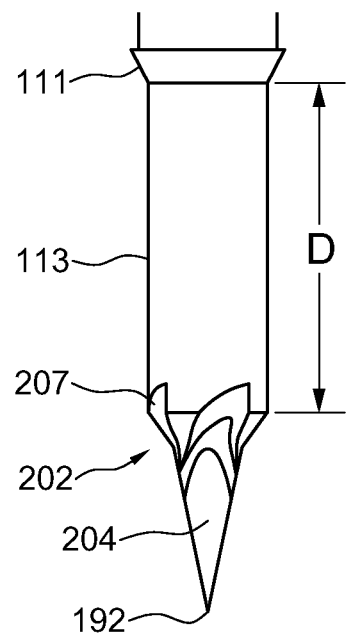
Figure 12A:
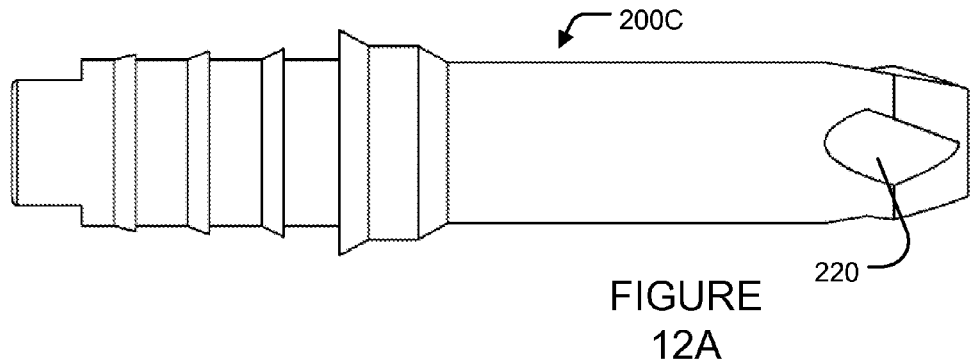
FIGS. 12A to 12E are views of a portal according to another embodiment of the invention.
Figure 12B:
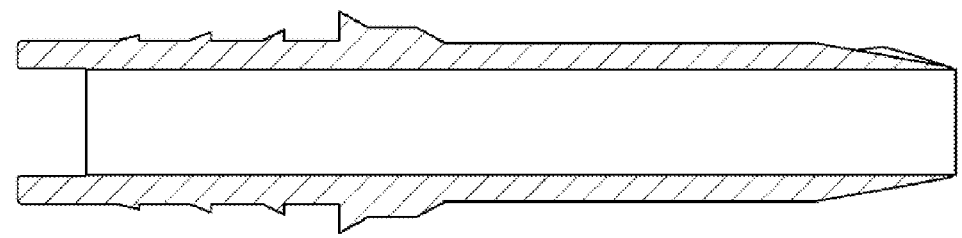
Figure 12C:
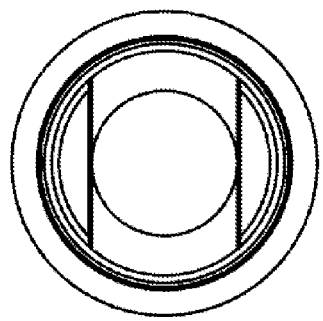
Figure 12D:
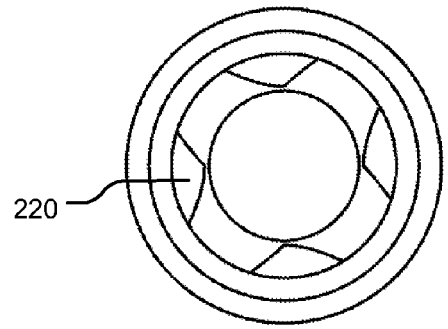
Figure 12E:
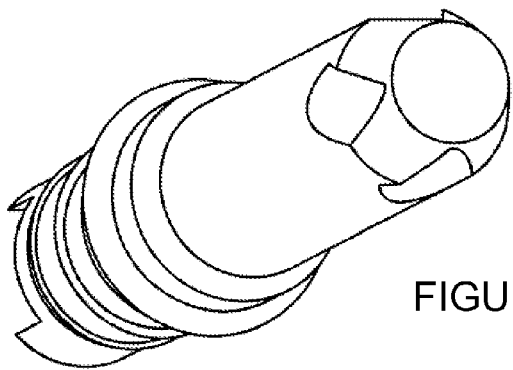

As shown in FIGS. 7A and 7B, stylet 192 may be equipped with facets 204 or other cutting features, and bone portal 113 may have cutting teeth 207 or other cutting features (e.g. serrations) on its leading edge 202. Facets 204 help stylet 192 to penetrate into the cortical bone CB as stylet 192 is being rotated into cortical bone CB. Facets 204 and cutting teeth 207 respectively help stylet 192 and bone portal 113 cut a clean passage through the cortical bone CB large enough to accept the bone-penetrating portion of bone portal 113. The length D of bone portal 113 for tibial portals may be slightly longer than that for sternal portals.

A guide 158 (shown in FIG. 6G) on base 199 centers and prevents buckling of stylet 192 so that it enters straight into the subject's tissues T. After bone portal 113 has been introduced to the desired depth (for example, such that bone stop 111 on bone portal 113 is against cortical bone CB thereby preventing deeper insertion of bone portal 113) introducer tool 10D may be removed by lifting handle 195 away from the subject. A tactile and/or audible snap, as described above with respect to introducer tool 10A, may be provided upon successful insertion of bone portal 113.

As handle 195 is lifted away from the subject, spring 198 causes shield 197 to be extended to avoid exposing stylet 192 which is pulled up as handle 195 is lifted. Further motion of handle 195 away from the subject disengages shield 197 from base 199, leaving bone portal 113 implanted in the subject's bone and the associated tube passing out through the subject's tissue and through the aperture in base 199. The user may use one hand to hold the base 199 down while the other hand is used to firmly pull handle 195 and shield 197 from base 199. Introducer tool 10D may then be discarded or processed for re-use. Infusion tube 125 extending from the now implanted bone portal 113 may be clipped to strain relief fittings on base 199. Fluids may be delivered to the subject or withdrawn from the subject by way of infusion tube 125 (e.g. a Luer fitting on infusion tube 125 may be fitted to a standard IV connector). Base 199 can optionally be used as a support for a sterile cover to cover the site of bone portal 113.

FIGS. 8A to 8C illustrates an introducer tool 10E according to another embodiment of the invention. Introducer 10E is similar to introducer tool 10D but is somewhat more compact and lacks a rotatable knob at the distal end of handle 310. FIGS. 8B and 8C show steps in using introducer 10E. Introducer tool 10E has an adhesive beneath base 312 that is exposed by peeling off release sheet 314. Base 312 is aligned with a subject's tibial tuberosity or other desired insertion site in a similar manner to that described above for introducer tool 10D. Base 312 is brought against the subject's skin and the user presses handle 310 toward the subject's bone until the bone portal has been introduced to the desired depth (for example, such that bone stop on bone portal is against cortical bone CB thereby preventing deeper insertion of bone portal). Introducer tool 10E may be removed by lifting handle 310 away from the subject, leaving the bone portal implanted in the subject's bone and the associated tube passing out through the subject's tissue and through an aperture in base 312. The user may use one hand to hold the base 312 down while the other hand is used to firmly pull handle 310. Base 312 can optionally be used as a support for a sterile cover, such as a dome, to cover the site of the bone portal.

FIGS. 9A to 9D illustrate a bone portal 200 according to one embodiment. Bone portal 200 has a bone-penetrating portion 201. A leading edge of portion 201 is tapered to ease the passage of bone-penetrating portion 201 into a subject's bone. The taper has an angle θ.

In some embodiments, the bone-penetrating portion 201 of the portal has a thin wall. This tends to reduce the outside diameter of the portal while preserving a desired capacity for fluid to flow through the portal. In an example embodiment, the portal has an outside diameter of less than about 1½ mm. In some embodiments, the walls of the bone-penetrating part of the portal have a thickness of about ¼ mm or less. These are examples only.

A bone stop 205 is provided on portal 200. Bone stop 205 may be provided by a portion of portal 200 integral with and having a diameter greater than that of bone-penetrating portion 201. In the illustrated embodiment, bone stop 205 has a tapered front face 206. Tapered front face 206 facilitates the penetration of bone stop 205 through soft tissues overlying the subject's bone. Face 206 is preferably tapered at an angle that is shallow enough that bone stop 205 tends not to wedge itself deeply into the subject's bone during insertion of portal 200.

To achieve penetration of the bone stop through tissues overlying a subject's bone, it is desirable that the leading edge of the bone stop have an angle of approximately 45 degrees to a centerline of the portal. For example, bone stop front face 206 may make an angle of about 40 degrees to 50 degrees with a longitudinal centerline of portal 200. In some embodiments, the bone stop may be somewhat sharper than this. For example in some embodiments bone stop 205 has an angle in the range of about 25 to 45 degrees to the centerline of portal 200. Other bone stop configurations may be provided in other embodiments.

A central passage 203 extends longitudinally through portal 200. Passage 203 may receive a stylet during insertion of portal 200. The stylet may be a sliding fit in central passage 203 so that it can be readily pulled out of portal 200 after insertion of the portal. During insertion of the portal, the stylet plugs passage 203 and prevents tissues from entering passage 203. After insertion, passage 203 permits fluids to be transported into the bone.

In the illustrated embodiment, barbs 208 are provided on a shank portion 209 of portal 200. Barbs 208 engage an inside of a flexible infusion tube which connects directly to portal 200. The infusion tube may be clamped around barbed shank 209 to prevent separation of the infusion tube from bone portal 200. For example, a collar (e.g. a band of stainless steel or other suitable metal or material) may be swaged around the tube over barbs 208 so that the tube is secured in place on bone portal 200.

In some embodiments, barbs 208 are graduated in size such that barbs closer to leading edge 202 are larger than barbs farther away from leading edge 202. This can be advantageous where the infusion tube is made from a relatively soft flexible material such as a suitable plastic or the like. Graduating the sizes of barbs 208 helps to distribute any strains caused by pulling on the tube over a number of barbs 208 thereby making the connection between the infusion tube and the bone portal 200 more secure than it would be if barbs 208 were all equal in size.

FIGS. 10A through 10D show a bone portal 200A according to another embodiment in which teeth 210 are provided on a leading edge of the bone portal. In bone portal 200A, teeth 210 have a geometry such that leading edge 212 of bone portal 200A is tapered. Front cutting edges 211 of teeth 210 are disposed at approximately 90 degrees to a centerline of portal 200A.

A rear edge of portal 200A has key or notch 213 in it for receiving a corresponding key or notch on a stylet or other driving member on a tool being used to drive the insertion of portal 200A.

FIGS. 11A to 11D show a portal 200B according to another embodiment of the invention. Portal 200B is similar to portal 200A with the exception that the teeth have a different geometry. In portal 200B, both leading and trailing edges of the teeth lie in a plane which includes longitudinal axis 215 of portal 200B. This allows the teeth to remove bone with portal 200B rotating in either direction.

FIGS. 12A to 12E show a portal 200C according to another embodiment in which cutting teeth 220 have a different geometry. In the illustrated embodiment, cutting teeth 220 are formed by grooving the outside of portal 200C in a location which straddles a boundary between a tapered leading edge of portal 200C and a generally parallel-sided tubular bone penetration portion of portal 200C. Teeth 220 do not penetrate entirely through the wall of portal 200C.

Figure 13:
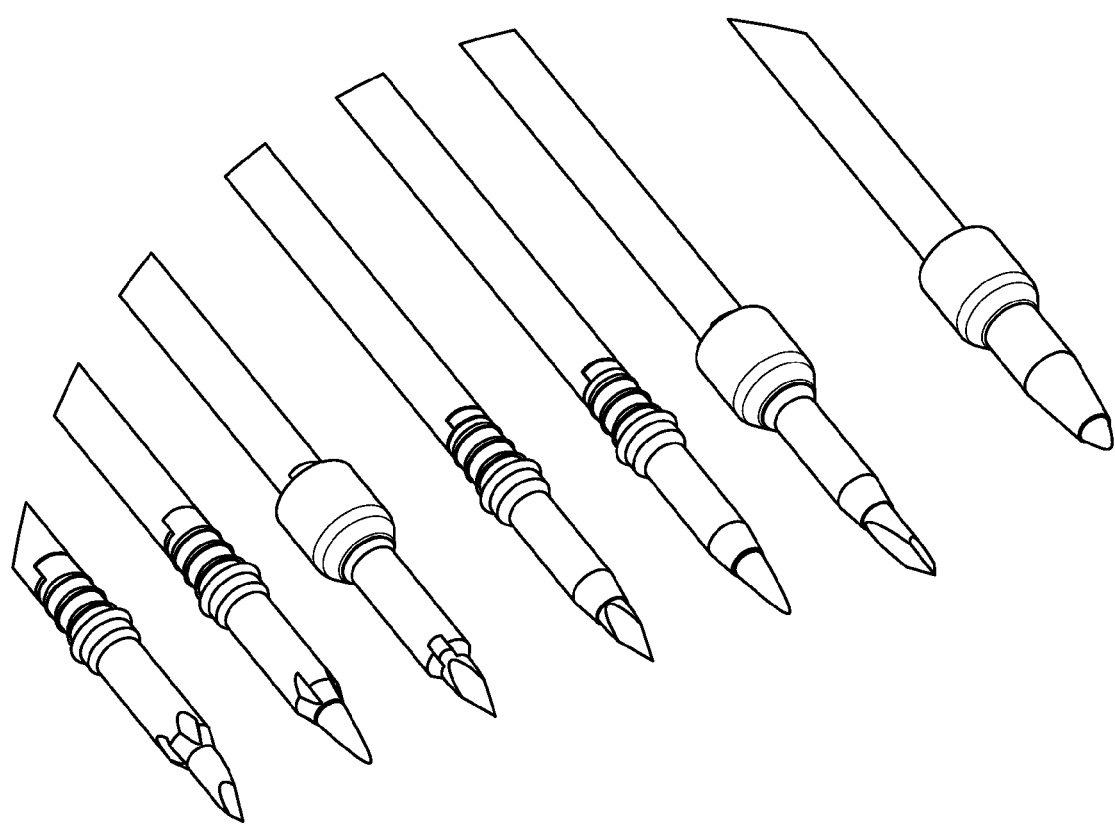
FIG. 13 shows portals according to various embodiments of the invention assembled onto stylets according to embodiments of the invention.
Figure 14A:
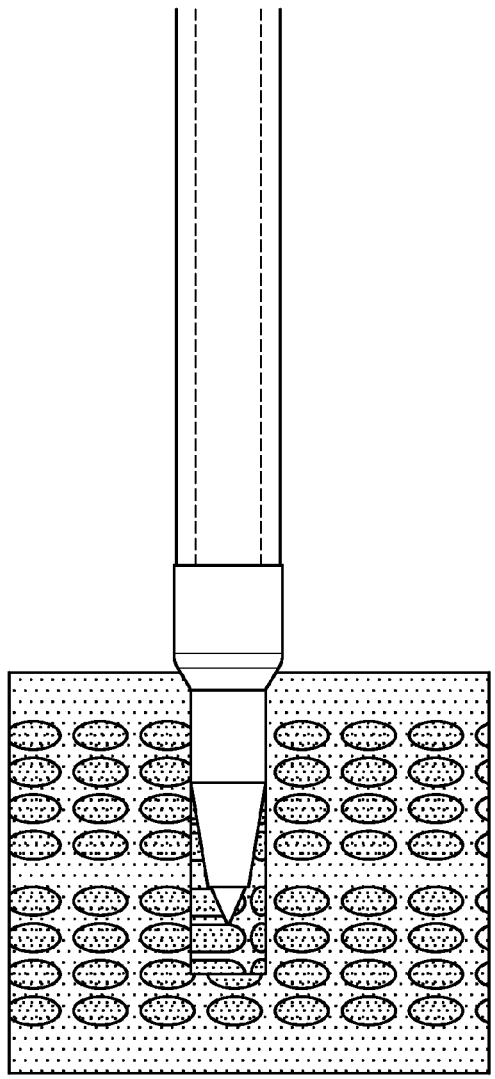
FIGS. 14A to 14E show various combinations of portals and stylets inserted into bone.
Figure 14B:
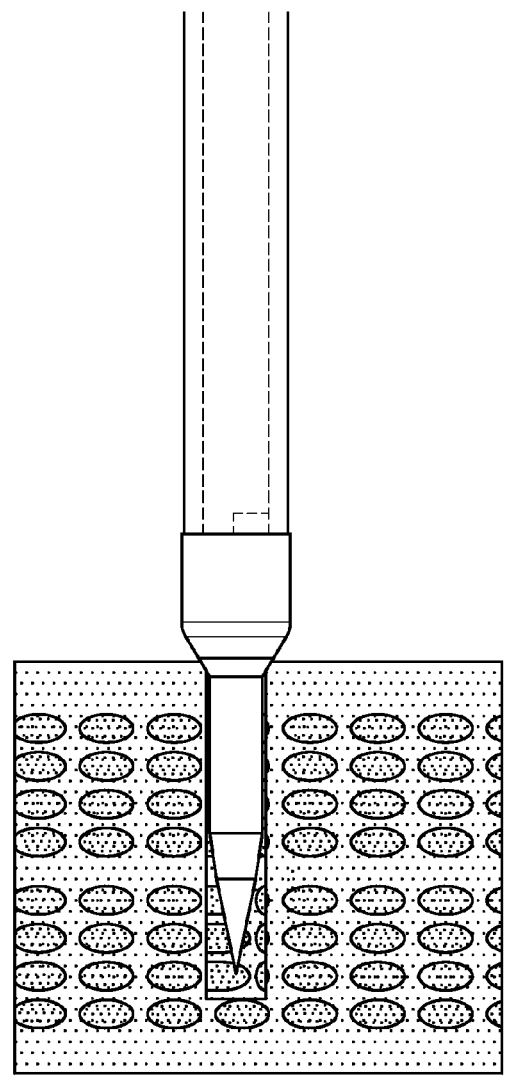
Figure 14C:
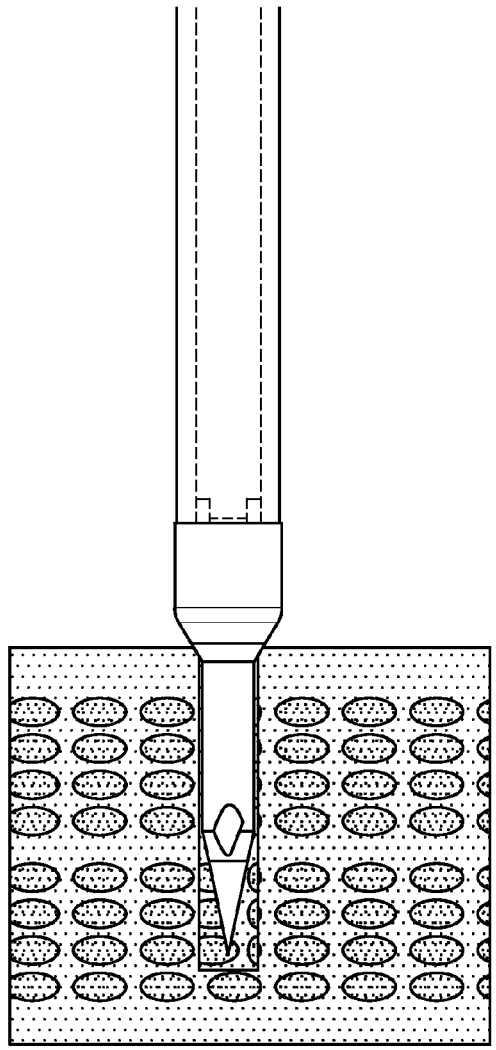
Figure 14D:
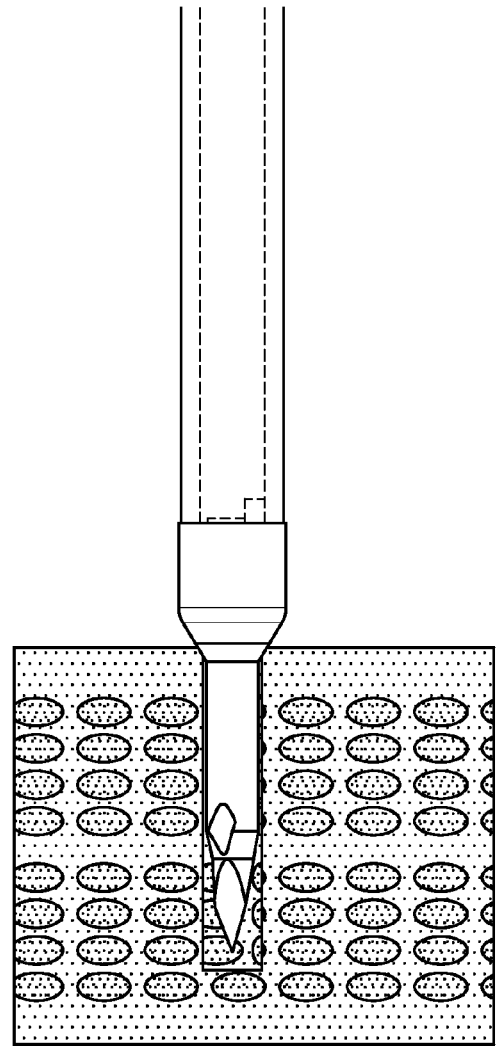
Figure 14E:
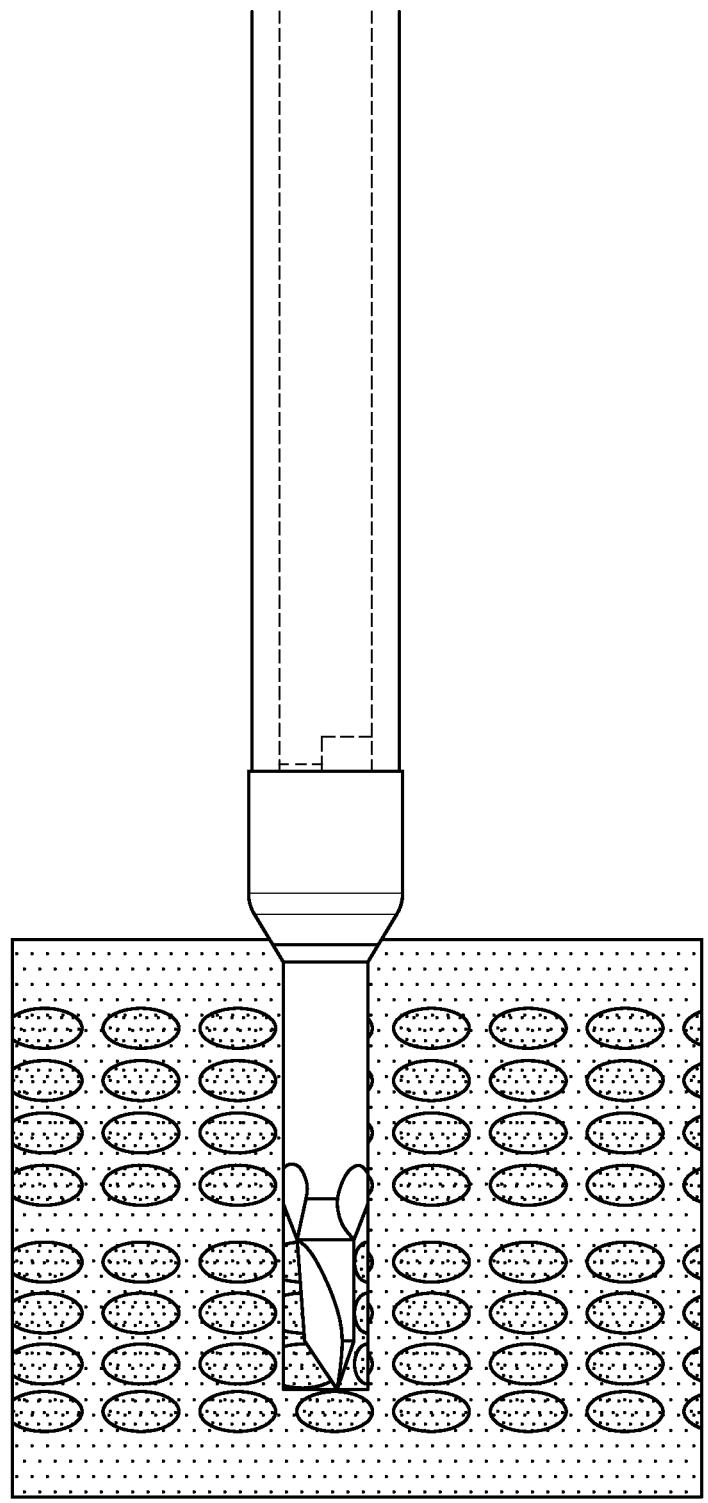

FIG. 13 shows bone portals according to various embodiments combined with stylets according to various embodiments. Infusion tubes are not shown in FIG. 13. Collars of a type that could be swaged around an infusion tube to hold the infusion tube to the shanks of the illustrated portals are shown on some of the portals for purpose of illustration. The collars are not present on other portals to reveal details of the shanks of the portals.

In general, in embodiments where a stylet will be introduced into bone without rotation of the stylet, the tip of the stylet may be conical or in the alternative may have facets teeth or the like on it. In embodiments where the stylet will be rotated to assist in penetrating bone it is generally desirable that the tip of the stylet be faceted or toothed or that the stylet tip has some other features that can chip or scrape away the bone when the stylet is rotated about its axis in order to assist in the placement of a bone portal.

FIGS. 14A to 14E show schematically various bone portals inserted into bone. The leading edge of each bone portal is in the marrow portion of the bone. The bone stop portion of the bone portal in each case is lodged against the tougher outer surface of the bone (e.g. against the cortical layer of the bone).

The various bone portals described herein are not limited in their application to the types of introducer tools for bone portals that are described herein. For example, the bone portals described herein have potential application in introducer tools that utilize different depth control mechanisms, different power sources (e.g. motorized), etc.

As noted above, different geometries of stylet may be provided. FIGS. 15A and 15B show a stylet 300 having a symmetrical conical tip. FIGS. 16A to 16C show a stylet 300A having a symmetrical faceted tip. Stylet 300A has facets 303 which meet at a sharp point 302 which is generally aligned with the centerline 301 of the stylet. Each facet has an angular extent of approximately 120 degrees.

In some embodiments it is desirable to provide a stylet which has a sharp point which is not aligned with the centerline of the stylet. Providing a point which is off-center can help to cause the stylet to make a hole in the bone when the stylet is rotated which is larger in diameter than the stylet itself. FIGS. 17A to 17D show, for example, a faceted stylet 300B in which one facet 303A is larger than the others, thereby providing a point 302 which is off-center. When stylet 330B as shown in FIGS. 17A to 17D is pressed into the surface of a bone and rotated, the stylet tends to wobble as it is rotated. Point 302 is not aligned with the central axis of the stylet. This wobbling results in the stylet cutting a hole in the subject's bone having a diameter that is somewhat larger than the diameter of the stylet itself. Such a hole assists in the placement of the bone-penetrating portion of a bone portal extending through the hole.

In some embodiments, the offset of the tip (dimension P in FIG. 17A) of the stylet is sufficient to make a hole that is about the same size as the outer diameter of the bone-penetrating part of the portal. In some embodiments, the offset of the point of the stylet from a centerline of the stylet is related to the outer diameter of the portal by the following equation:

$$\frac{D_{PORTAL}}{2} \geq \frac{D_{STYLET}}{2} + \text{OFFSET} \quad (1)$$

where $D_{PORTAL}$ is the outer diameter of the bone-penetrating part of the portal; $D_{STYLET}$ is the outer diameter of the stylet just behind the tip; and OFFSET is the amount of offset between the point of the stylet and the centerline of the stylet.

In some embodiments, the offset from the centerline of the tip of the stylet is approximately equal to the difference in radius of the stylet and portal which, in turn, may be equal to the wall thickness of the bone-penetrating part of the portal. It is not necessary that the hole made by the stylet be equal in diameter to the outer diameter of the portal. It is generally desirable that the bone-penetrating part of the portal should be a reasonably snug fit in the hole into which it penetrates the bone. This prevents excessive leaking around the portal.

It is desirable that the stylet tip and bone portal be shaped in such a manner that the insertion of the portal does not tend to create cracks in the bone or to create weaknesses that may eventually result in cracks in the bone. To facilitate this, it is desirable that the bone-penetrating portion of the portal be relatively small in outside diameter. This reduces the force required to insert the portal and minimizes the stresses on the bone during introduction of the portal. It is also desirable that the tip of the stylet be relatively sharp (in some embodiments the stylet tip has a point that is very sharp). For example the stylet tip may be sharper than fifteen degrees. In a prototype embodiment a stylet tip has a conical point having a cone angle of 12 degrees measured between a centerline of the stylet. In other embodiments, the stylet tip is faceted and the facets make an angle of approximately 12 degrees with a centerline of the stylet.

The stylets described herein are not limited to application with introducer tools for placing bone portals. For example, the stylets described herein have potential application in bone biopsy devices, as well as in other devices used in medical, veterinary, and research contexts that require procedures such as cutting, piercing, boring, drilling, perforating and the like of body tissues.

Figure 18A:
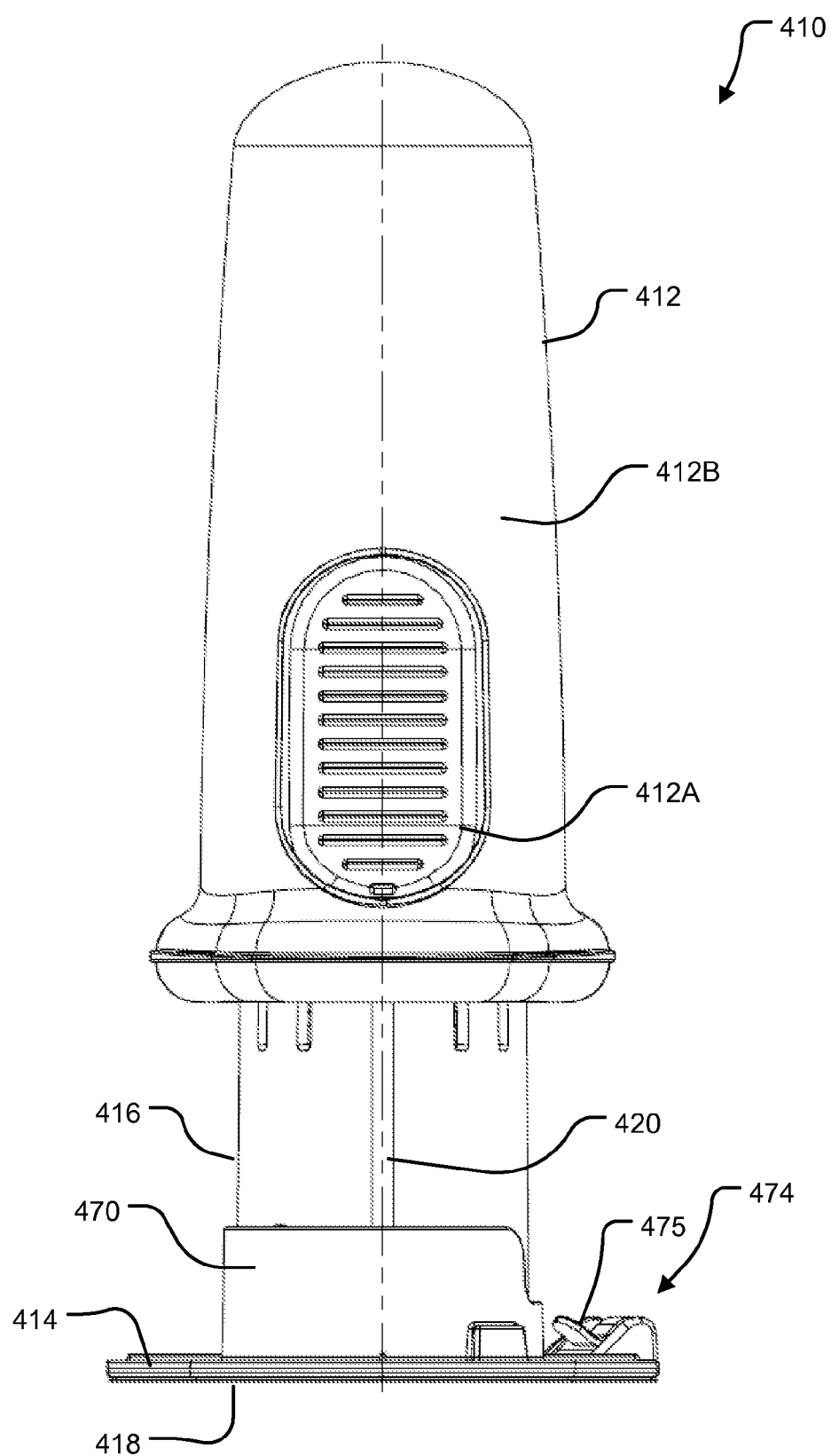
FIG. 18A is a front elevation view of an introducer tool according to an embodiment of the invention and FIG. 18B is a perspective view thereof.
Figure 18B:
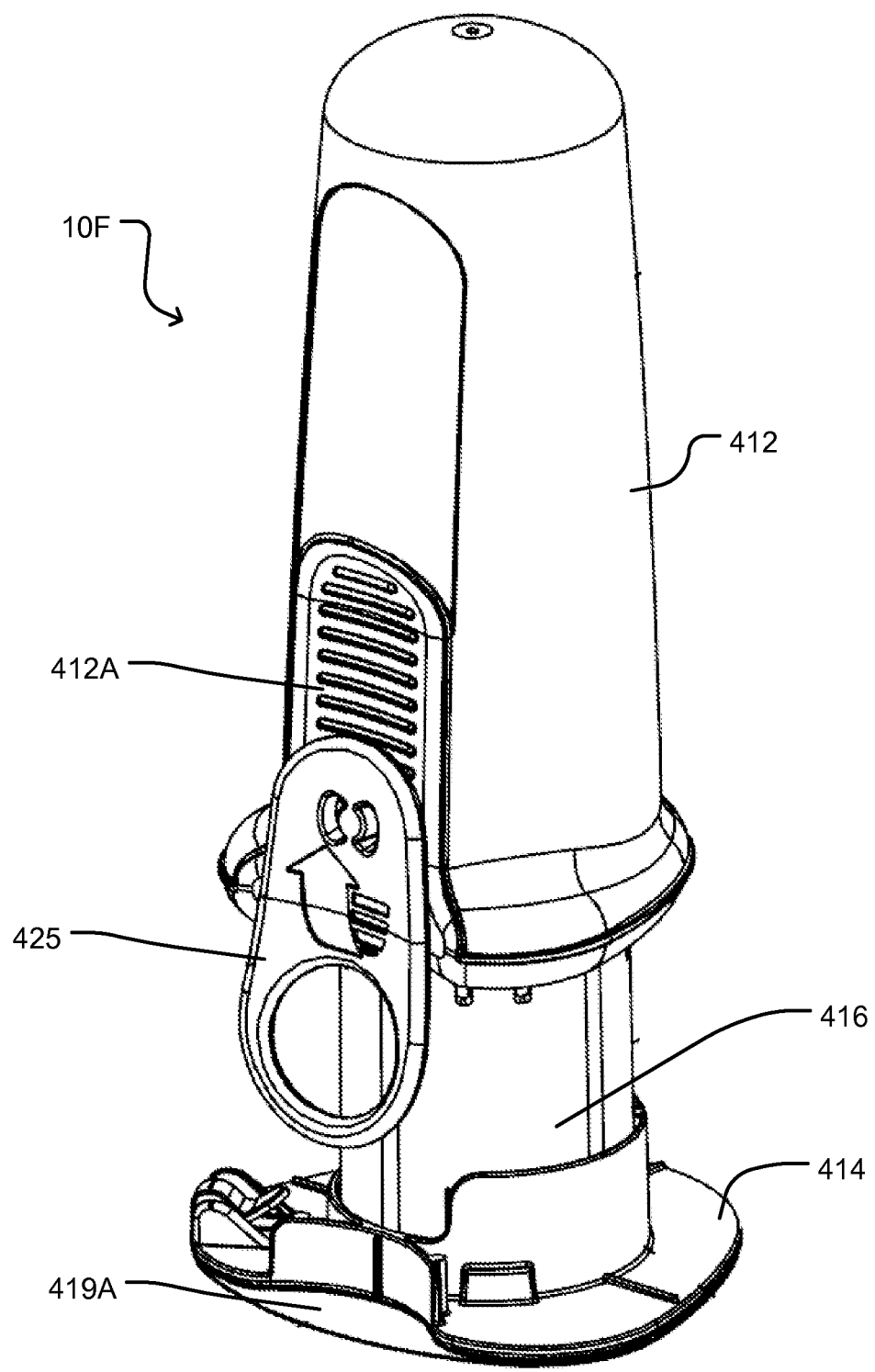
Figure 19:
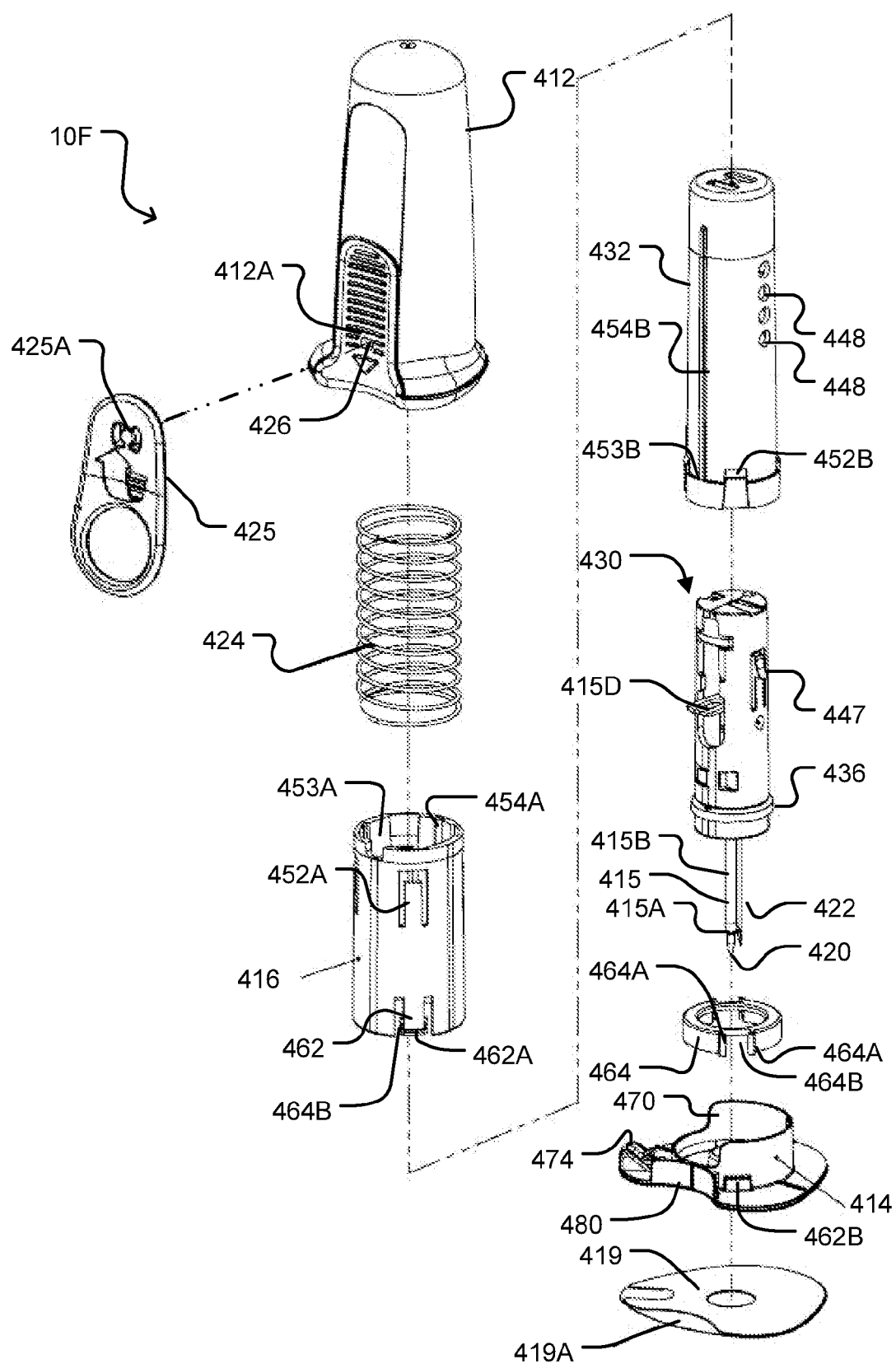
FIG. 19 is an exploded view of the introducer tool of FIG. 18A.
Figure 20:
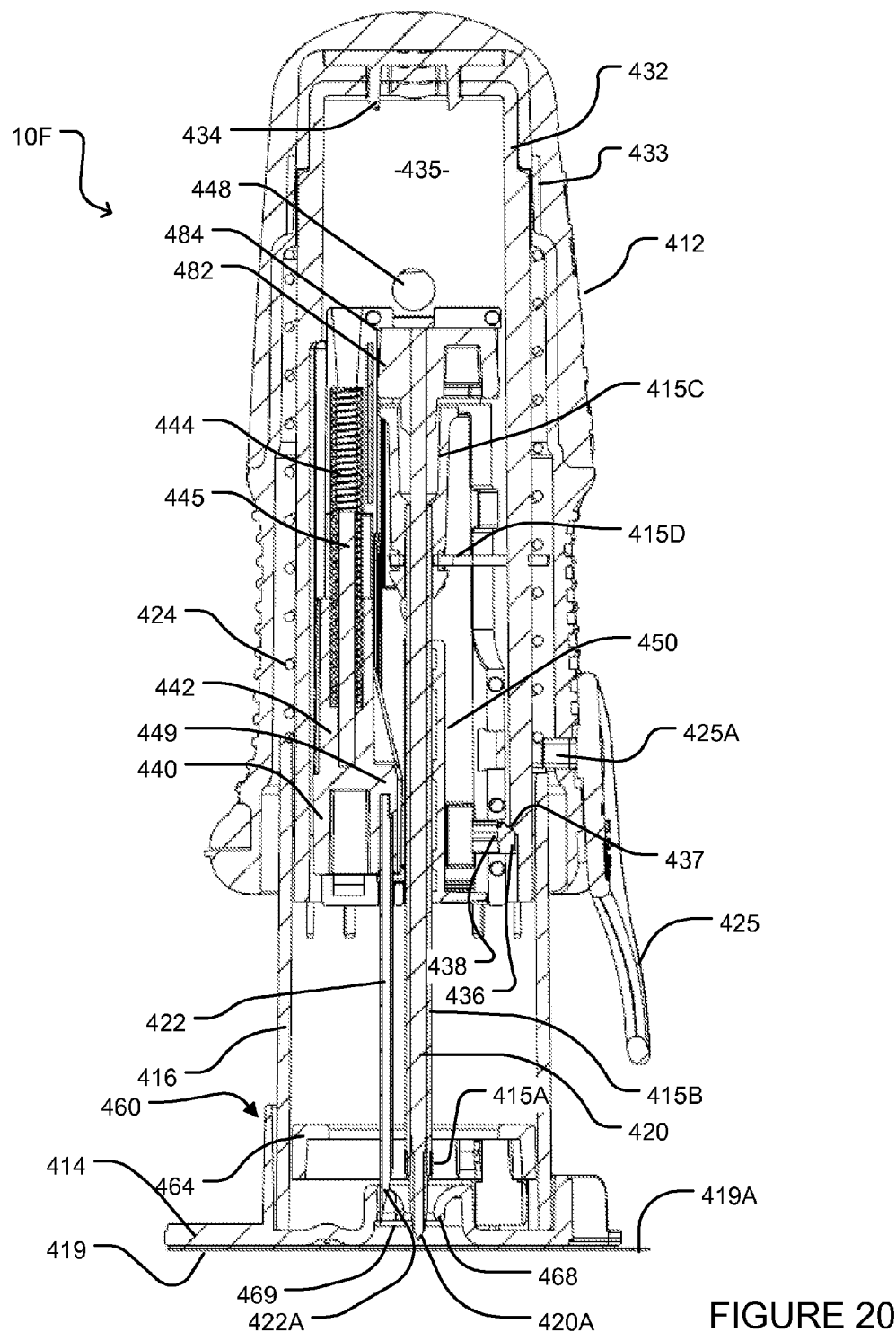
FIG. 20 is a cross-sectional side view of the introducer tool of FIG. 18A.

FIGS. 18 to 20 show an introducer tool 10F according to another embodiment of the invention. Introducer tool 10F has a handle 412 that can be grasped by a user and a base 414 that may be placed against a subject.

Handle 412 has a grip 412A. Surfaces 412B are coated in resilient material that provides a good grip. Handle 412 may be asymmetrical. For example, in the illustrated embodiment, handle 412 is indented in the vicinity of grip 412A. The shape of the proximal end of handle 412 is similar to that of base 414. This helps the user to quickly position base 414 in appropriate alignment with a subject for insertion of a bone portal. Base 414 is not required in all embodiments. In embodiments which lack a base 414, an asymmetrical handle 412 can aid in achieving correct orientation of handle 412 for introduction of a bone portal.

Introducer tool 10F may be used to apply an infusion tube assembly 415 to a subject such that a bone portal 415A of the infusion tube assembly is inserted at a desired location into the subject's bone. FIGS. 19 and 20 show an infusion tube assembly 415 mounted on stylet 420.

Figure 22A:
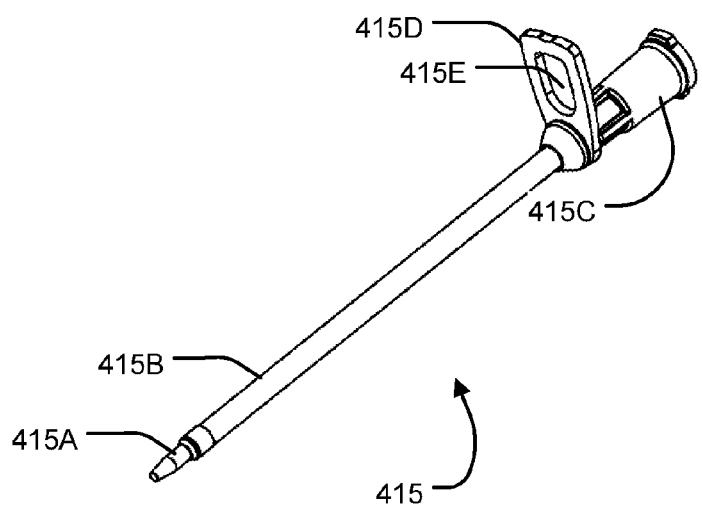
FIGS. 22A and 22B are respectively perspective and exploded views of an infusion tube assembly.
Figure 22B:
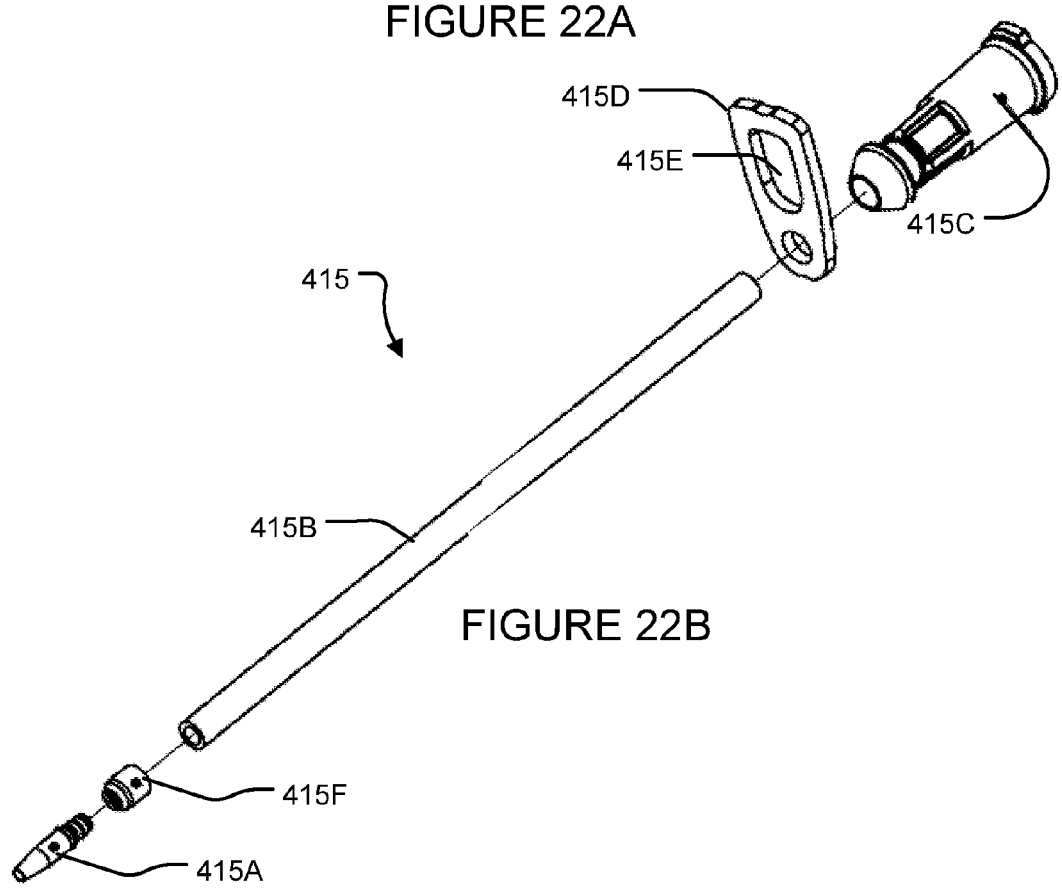

In the illustrated embodiment, infusion tube assembly 415 comprises a bone portal 415A, an infusion tube 415B, a fitting (in the example embodiment a Luer fitting) 415C and a strain relief member 415D. Advantageously, infusion tube 415B is flexible. Infusion tube assembly 415 is shown in detail in FIGS. 22A and 22B. In the illustrated embodiment bone portal 415A is connected to infusion tube 415B by way of a barbed fitting that fits into the bore of infusion tube 415B and a collar 415F that is swaged around the outside of infusion tube 415B to provide a reliable coupling. Suitable alternative means could be used for coupling portal 415A to infusion tube 415B.

Base 414 is supported on a retractable shield 416. Shield 416 protects a stylet 420 that carries an infusion tube assembly 415 comprising a bone portal 415A (see FIG. 19). Base 414 is coupled to shield 416 by a release mechanism. An example release mechanism is described below.

An adhesive 419 is provided on a lower face 418 of base 414. A release sheet 419A can be peeled off to expose adhesive 419. In the illustrated embodiment, release sheet 419A may be conveniently removed from base 414 by pulling on release sheet 419A in the region of a recess 479 in base 414. However, in alternative embodiments, release sheet 419A may be provided with a tab or tabs which a user may pull to peel off release sheet 419A. Release sheet 419A may comprise a single sheet or two or more separate parts. Further, in some embodiments the shape of release sheet 419A matches the shape of base 414 by including an indentation in the region of recess 479.

Introducer tool 10F may be operated by placing base 414 against the skin of a subject over a bone into which it is desired to insert a bone portal. In the illustrated embodiment, introducer tool 10F has guide features that help a user align the introducer over a subject's sternum. In other embodiments guide features are provided to facilitate alignment with anatomical landmarks at other infusion sites. Base 414 may then be adhered to the subject's skin by way of the adhesive 419 on surface 418. The user can operate introducer tool 10F to place a portal into the subject's bone by pushing on handle 412. As handle 412 is pushed, shield 416 telescopes into handle 412 and stylet 420 penetrates the subject's skin carrying bone portal 415A with it.

Base 414 assists in keeping introducer tool 10F over the desired location and in the desired orientation. In the illustrated embodiment, base 414 is more-or-less perpendicular to stylet 420 and assists in introducing stylet 420 straight into the subject's sternum. Base 414 may comprise guide features that assist a user in aligning stylet 420 with a desired infusion site, for example as described in the previous embodiments described above.

A release mechanism uncouples stylet 420 from handle 412 when portal 415A has penetrated the subject's bone to a desired depth. The depth is typically set so that the portal will stop when its tip is in the subject's bone marrow. The release mechanism comprises a bone probe 422 (see FIG. 20) and is illustrated in detail in FIGS. 21A through 21C.

After the release mechanism is triggered, a base release mechanism uncouples base 414 from shield 416. Handle 412 may then be withdrawn to leave in place base 414, the implanted portal 415A and the rest of infusion tube assembly 415. As handle 412 is withdrawn, shield 416 is urged outwardly from handle 412 so as to protect any users from inadvertent contact with stylet 420 or bone probe 422. Base 414 can remain adhered to the subject's skin to protect the infusion site and to provide an anchor for strain relief for any tubing that may be coupled to the infusion tube assembly, or to provide strain relief for other tubing systems, catheters, or the like.

In embodiments which do not have a base 414, alternative means such as a stiffener or other support mechanism may be provided to maintain the orientation of stylet 420 during insertion. In some embodiments a plurality of bone probes (for example 2 or 3 bone probes) are provided. The bone probes may be arranged so that they stabilize the introducer tool during insertion of a bone portal and facilitate holding stylet 420 over a desired location on the subject at a desired orientation during introduction of the bone portal. For example, three bone probes may be arranged in a triangle surrounding stylet 420.

A locking pin assembly 425 comprises a pin 425A that can be received through an aperture 426 in handle 412. Pin 425A must be removed before introducer tool 10F can be used. In the illustrated embodiment, pin 425A prevents operation of introducer tool 10F when inserted into aperture 426 by blocking shield 416 from telescoping into handle 412. Locking pin assembly 425 may be inserted during manufacture or before use of introducer tool 10F and removed to prepare introducer tool 10F for use.

A carrier assembly 430 supports stylet 420 and bone probe 422. Carrier assembly 430 is received within the bore of a sleeve 432 that is mounted in a cavity 433 inside handle 412. In the illustrated embodiment, a coupling 434 holds sleeve 432 in place. A spring 424 biases shield 416 proximally in handle 412. Spring 424 sits in an annular space surrounding sleeve 432.

Figure 21A:
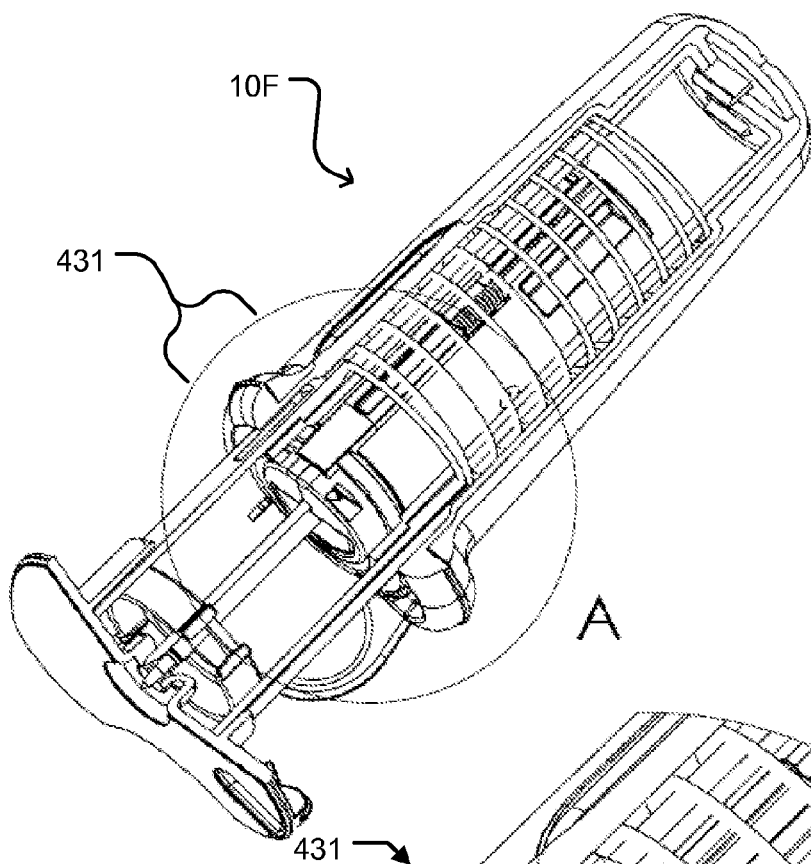
FIGS. 21A and 21B are cut-away views showing a release mechanism of the introducer tool of FIG. 18A
Figure 21B:
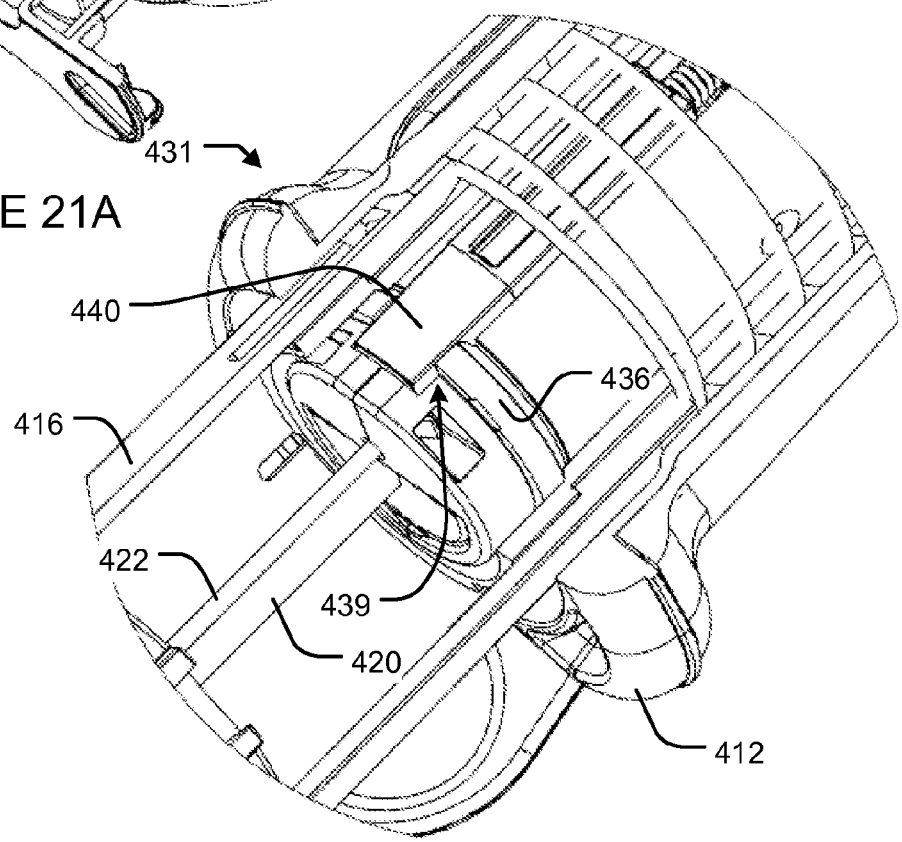
Figure 21C:
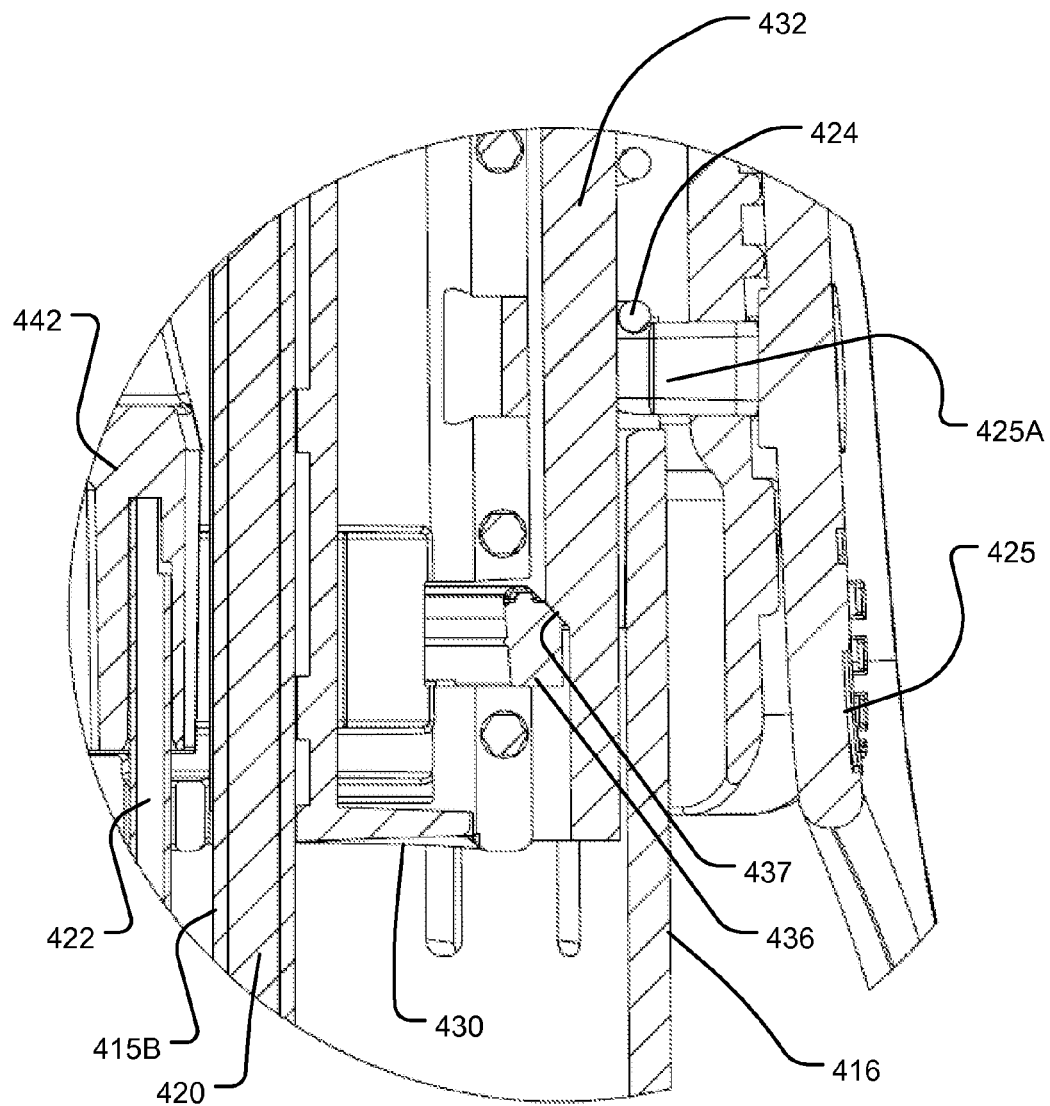
FIG. 21C is a cross-sectional detail view of a portion of the release mechanism.

Carrier assembly 430 is initially prevented from sliding into a space 435 inside sleeve 432 by a release mechanism 431. Release mechanism 431 causes longitudinal actuating forces to be transmitted from handle 412 via sleeve 432 to carrier assembly 430 and thus to stylet 420. FIGS. 21A and 21B show an example release mechanism 431.

In the example embodiment, a deformable member couples handle 412 via sleeve 432 to carrier assembly 430. The deformable member is prevented from deforming so as to permit relative motion of carrier assembly and handle 412 by another member. The other member is moved relative to the deformable member in response to bone probe 422 contacting a subject's bone. This permits the deformable member to deform in a way that uncouples handle 412 from carrier assembly 430. The deformable member may comprise a ring having a gap.

The illustrated release mechanism 431 (see FIGS. 21A to 21C) comprises a release ring 436 that abuts against an angled surface 437 of sleeve 432. Release ring 436 is received in a groove 438 that extends around carrier assembly 430. Release ring 436 has a gap 439 that is initially filled by a sliding block 440. When carrier assembly is urged toward space 435 for example, as a result of the application of force to handle 412 pushing the proximal end of stylet 420 into tissue or bone, the reaction forces exerted by angled surface 437 on release ring 436 transmit force to release ring 436 and also act to compress release ring 436 radially into groove 438. Release ring 436 resists being radially compressed and therefore remains in place, abutting against angled surface 437.

Sliding block 440 is part of a sliding carrier 442 to which bone probe 422 is attached. Carrier 442 is biased in the direction of the tip of bone probe 422 by a spring 444. Spring 444 has a spring constant sufficiently great that longitudinal forces expected when bone probe 422 passes through soft tissues such as skin, fat and muscle are not sufficient to displace carrier 442 enough that sliding block 440 moves out of gap 439 against the bias forces exerted by spring 444. Spring 444 is sufficiently weak that it cannot apply enough force to sliding carrier 442 to press bone probe 422 any significant distance into bone. In the illustrated embodiment a pin 445 guides spring 444 and prevents spring 444 from buckling.

The operation of release mechanism 431 can now be understood. When a user presses on handle 412, handle 412 begins to move toward a subject. The user must apply enough force to handle 412 to overcome the resistance provided by spring 424. As handle 412 moves toward the subject, stylet 420 and bone probe 422 are extended past the bottom surface 418 of base 414 and penetrate the subject's skin. When the tip of stylet 420 hits the subject's bone, stylet 420 penetrates the bone, carrying portal 415A with it.

Bone probe 422 also hits the subject's bone. However, bone probe 422 stops when it hits the surface of the bone because spring 444 is not strong enough to force bone probe 422 into the bone. Sliding carrier 442 is connected to bone probe 422 and also stops when bone probe 422 hits the subject's bone. Handle 412 continues to move toward the subject until release ring 436 has been carried past sliding block 440. This results in relative movement between sliding block 440 and release ring 436. When sliding block 440 is no longer in gap 439, release ring 426 can no longer resist being compressed radially inwardly into groove 438. This disengages handle 412 and sleeve 432 from carriage assembly 430.

Continued motion of handle 412 toward the subject causes carriage assembly 430 to move into space 435 at the distal end of sleeve 432. As carriage assembly 430 moves further into sleeve 432 it is held by a one-way mechanism that permits carriage assembly 430 to move into sleeve 432 but prevents the carriage assembly 430 from subsequently being pulled out of sleeve 432. The one-way mechanism may, for example, comprise a ratchet mechanism. In the illustrated embodiment, the ratchet mechanism comprises a pawl 447 that engages recesses 448 (which are apertures in the illustrated embodiment). The one-way ratchet mechanism holds carrier assembly 430 retracted within the bore of sleeve 432. This prevents reuse of introducer tool 10F. The one-way mechanism may comprise elements in addition to or instead of the illustrated pawl 447. For example one or hooks, locking rings, stops or the like may be arranged to permit carrier assembly 430 to move into sleeve 432 and to hold carrier assembly 430 from being subsequently moved outwardly in sleeve 432.

It can be seen that in the illustrated embodiment, bone probe 422 is very close to stylet 420. This is achieved by mounting bone probe 422 on a mounting base 449 that projects inwardly from sliding carriage 442. In the illustrated embodiment, tip 422A of bone probe 422 comprises an end face that is angled toward the tip 420A of stylet 420. Bone probe 422 may be tubular. Bone probe 422 may comprise a hypodermic needle, for example. Preferably, the tip of bone probe 422 is angled toward the tip 420A of stylet 420 so that force applied to the bone probe 422 upon insertion into a subject pushes bone probe 422 away from stylet 420, rather than towards stylet 420.

Stylet 420 can be subjected to significant forces during operation. As a precaution to prevent buckling of stylet 420 during insertion, a removable stiffener 450 may be clipped around stylet 420 outside of infusion tube 415B.

The construction and operation of shield 416 will now be described. As seen in FIG. 19, shield 416 comprises tabs 452A located toward its distal end. When shield 416 is assembled onto sleeve 432, tabs 452A engage recesses 452B on the outer surface of sleeve 432. In operation, a user must initially push on handle 412 with enough force to cause tabs 452A to ride out of recesses 452B. This ensures that the user will initiate introduction of a bone portal with sufficient force to properly implant the bone portal, and also provides sharps protection before the introducer tool 10F is in place on a subject.

When shield 416 is assembled onto sleeve 432 blocks 453A at the distal end of the bore of shield 416 abut against corresponding faces 453B on the outer surface of sleeve 432 and thereby prevent spring 424 from pushing shield 416 off of the proximal end of sleeve 432.

In the illustrated embodiment, shield 416 has guides that coact with corresponding features of sleeve 432 to prevent rotation of carrier assembly 430 relative to base 414 during insertion. In the illustrated embodiment, longitudinal grooves 454A in the bore of shield 416 receive corresponding ribs 454B on the outer surface of sleeve 432. Alternatively, grooves could be provided on the outer surface of sleeve 432 could receive corresponding ribs in the bore of shield 416.

Figure 23:
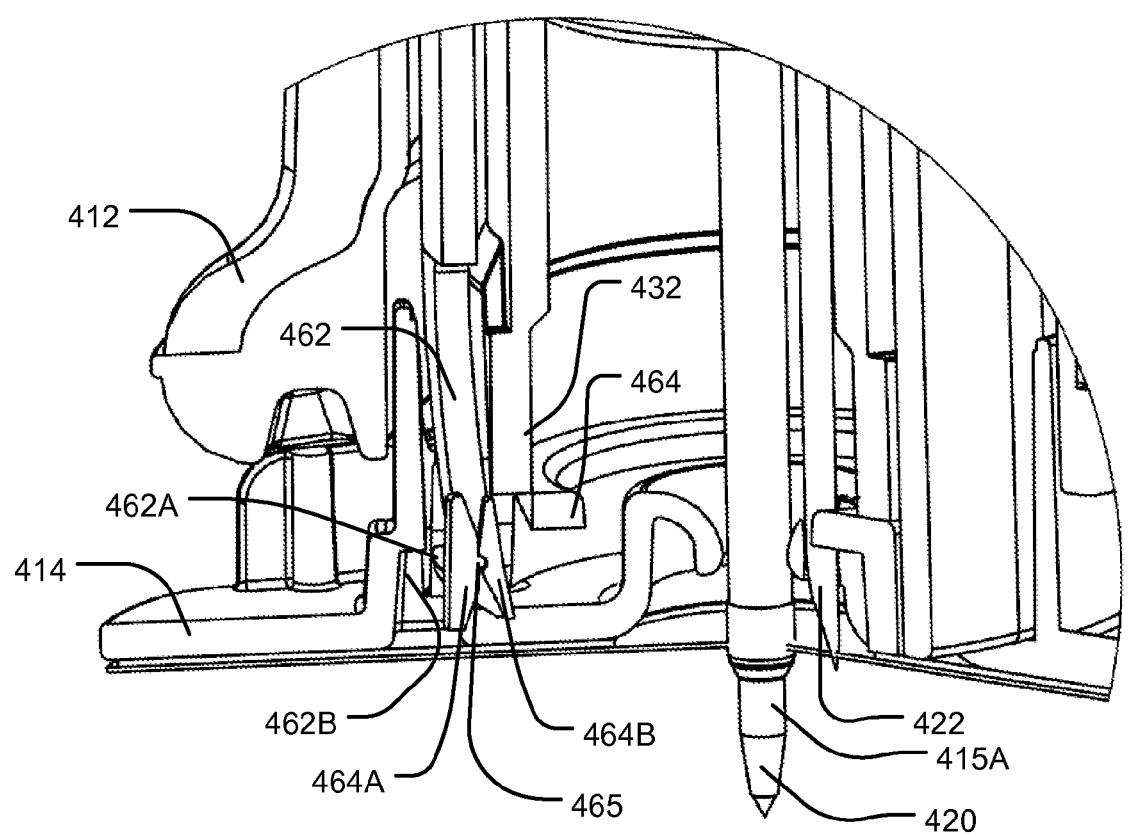
FIG. 23 is a cut-away detail view showing parts of a base release mechanism.

As noted above, base 414 is released from sleeve 416 during use of introducer tool 10F. The release mechanism advantageously completely releases base 414 from shield 416 so that shield 416 does not unduly pull on base 414 when the remainder of introducer tool 10F is removed after insertion. This can be achieved, for example, by providing a suitable base release mechanism that is mechanically actuated by the approach of handle 412 to base 414. An exemplary base release mechanism 460 is illustrated in detail in FIGS. 19 and 23. Base release mechanism 460 comprises a pair of tabs 462 carrying barbs 462A that engage corresponding recesses 462B in base 414. Prior to insertion and during the initial stages of insertion the engagement of barbs 462A in recesses 462B keeps base 414 firmly engaged on the end of shield 416. This protects users from coming into contact with the sharp ends of bone probe 422 and stylet 420 (i.e. provides sharps protection). This also helps to maintain a desired orientation of introducer tool 10F relative to a subject during introduction of bone portal 415A.

Base release mechanism 460 includes an actuating member 464. Actuating member 464 is located such that it is pushed in a proximal direction by handle 412, typically after release mechanism 431 releases. In the illustrated embodiment, movement of actuating member 464 pulls barbs 462A out of engagement with recesses 462B. This can be seen most clearly in FIG. 23.

Actuating member 464 comprises fingers 464A that engage corresponding profiles 464B on tabs 462. In the final stages of the introduction of a bone portal, the proximal end of sleeve 432 pushes actuating member 464 toward base 414. As shown best in FIG. 23, fingers 464A and profiles 464B are shaped so that they draw barbs 462A inwardly when actuating member is pushed in a proximal direction. This releases base 414 from shield 416. A holding feature 465 (for example a small projection from finger 464A that engages a corresponding recess in profile 464B or vice versa) keeps actuating member in position to hold barbs 462A retracted.

The detachable bases described herein are limited in their application to the types of introducer tools for bone portals that are described herein. For example, the detachable bases described herein have application in introducer tools that utilize different depth control mechanisms, different power sources (e.g. motorized), etc.

Figure 24:
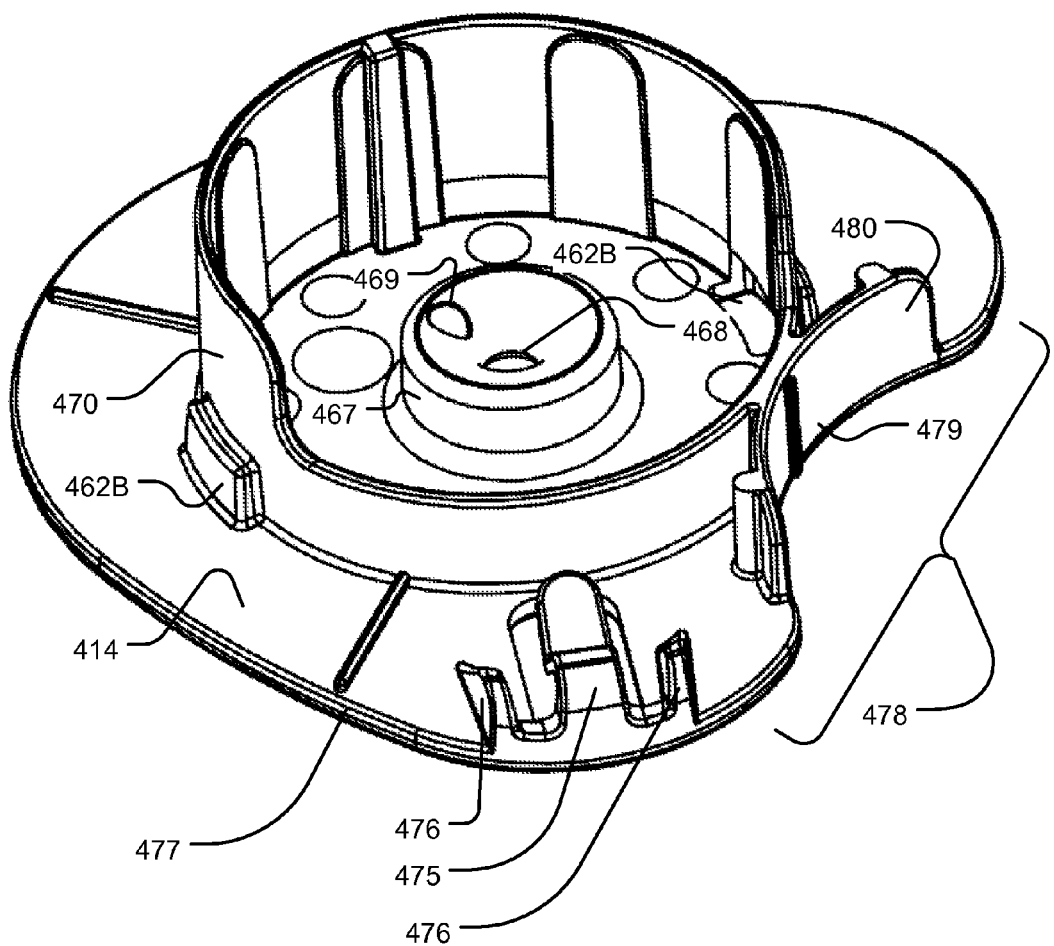
FIG. 24 is a perspective view of an example base.

Base 414 is shown in detail in FIG. 24. Base 414 helps to guide stylet 420 and bone probe 422 during introduction of a portal 415A. To this end, base 414 provides an aperture 468 which receives and guides stylet 420 and an aperture 469 which receives and guides bone probe 422. Aperture 468 is large enough to pass infusion tube 415B. The clearance between the sides of aperture 468 and infusion tube 415B may be small so that aperture 468 provides a seal around infusion tube 415B after introduction. Apertures 468 and 469 are located on a raised surface 467. A cavity under surface 467 may be provided over the vicinity of the infusion site.

Base 414 has a wall 470 that extends around the infusion site. After introduction of a bone portal, wall 470 prevents the infusion tube 415B projecting through guide aperture 468 from being crushed against the subject. Wall 470 is not necessarily continuous. A plurality of projections could be provided for a similar purpose.

Base 414 includes a strain relief fitting 474. After introduction of bone portal 415A, strain relief member 415D can be coupled to strain relief fitting 474. In the illustrated embodiment, strain relief fitting 474 comprises a hook 475 that passes through an aperture 415E in strain relief member 415D. Strain relief member 415D may be made of an elastic material to minimize shock on base 414 where there is a sudden pull on fitting 415C. In the illustrated embodiment, guide members 476 are provided to facilitate connection of strain relief member 415D to hook 475 and to discourage attempts to use hook 475 incorrectly. For example, guide members 476 prevent a user from inserting infusion tube 415B under hook 475.

Many alternative arrangements for a strain relief fitting are possible. For example, hook 475 may be oriented in a direction other than the radially-inward orientation that is depicted. Hook 475 could be oriented in a tangential direction on base 414. Hook 475 could have a curve or bend to permit member 415D to be engaged with hook 475 in a first direction and then pulled in a second direction for complete engagement. The first and second directions could be roughly at right angles to one another for example. As an alternative to hook 475 and aperture 415E, strain relief member 415D may comprise a ball or other expanded portion that can be engaged in a corresponding fitting on base 414.

In alternative embodiments one or more separate adhesive patches carrying strain relief fittings may be provided. The separate patches may be adhered to the subject's skin near to the insertion site before or after insertion of a bone portal.

The strain relief fittings described above are not limited in application to use with bone portal/infusion tube assemblies. Application in other medical contexts such as catheterization, intubation and the like are also encompassed by the scope of this invention.

The illustrated base 414 comprises an edge 477 that is profiled to assist a user in the proper placement of introducer tool 10F on a subject. For example, edge 477 has a section 478 that includes a recess 479 that can be aligned with the sternal notch of a subject. When recess 479 is aligned with the subject's sternal notch then stylet 420 is located over a target infusion site on the subject's sternum. A wall 480 projects upwardly along notch 479. A user can palpate the subject's sternal notch with a finger and position base 414 with notch 479 in registration with the palpating finger. Wall 480 helps the user to feel when base 414 is properly aligned with the subject's sternum.

As noted above, the design of introducer tool 10F permits bone probe 422 to be spaced closely to stylet 420. In some embodiments, bone probe 422 is spaced apart from the center of stylet 420 by a distance that is smaller than a radius of fitting 415C. In the illustrated embodiment, sliding carrier 442 has a dogleg portion that makes space for fitting 415C beside sliding carrier 422 while supporting bone probe 422 close to stylet 420.

Figure 25A:
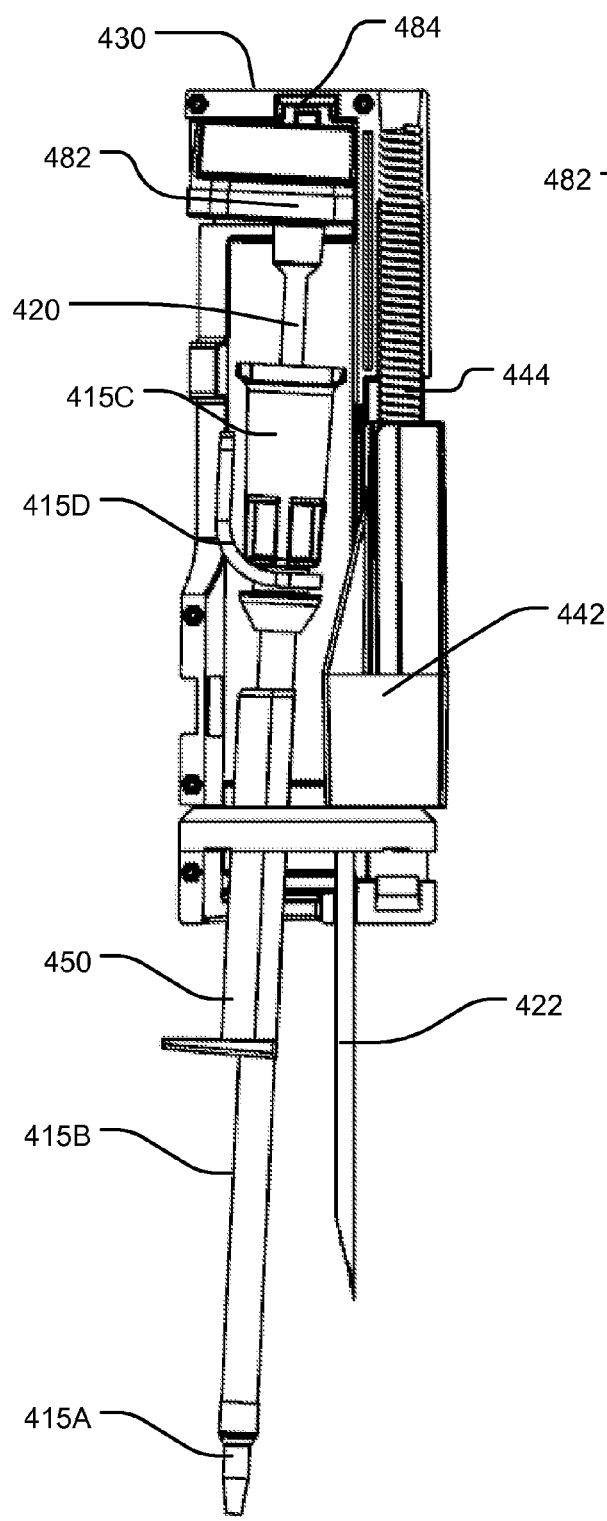
FIGS. 25A and 25B are views of a carrier assembly that illustrate an example mechanism for providing a stylet that can be pivoted to facilitate sliding an infusion tube assembly off of the stylet.
Figure 25B:
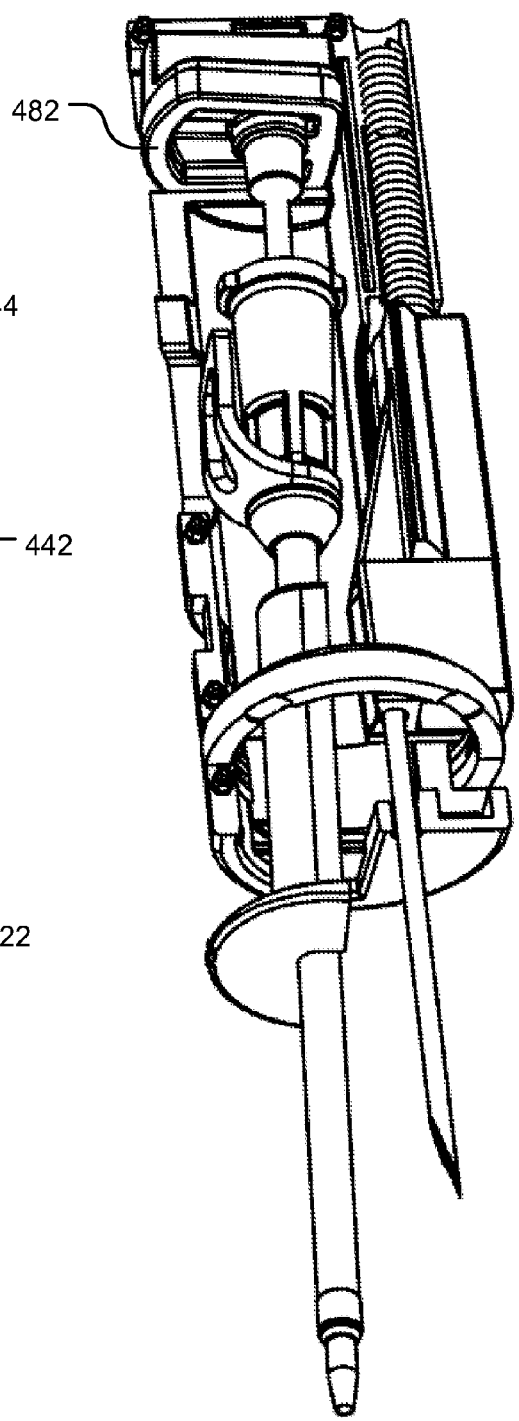

In embodiments in which bone probe 422 is spaced apart from the center of stylet 420 by a distance that is smaller than a radius of fitting 415C, stylet 420 and bone probe 422 may be movable relative to one another to permit stylet 420 to slide out of infusion tube assembly 415 after introduction. FIGS. 25A and 25B illustrate one such embodiment. In the illustrated embodiment, stylet 420 is mounted pivotally to carrier assembly 430. This permits stylet 420 to move far enough away from bone probe 422 to allow fitting 415C to slide along and off the tip of stylet 420. In other embodiments, the bone probe may be mounted pivotally to the carrier assembly permitting the bone probe to move far enough away from the stylet to allow the fitting to slide along and off the tip of the stylet.

Details of the mounting of stylet 420 in the illustrated embodiment can be seen in FIG. 20. Stylet 420 is mounted to a base 482 that is received in a cavity 484 in carrier assembly 430. Base 482 can rock sufficiently within cavity 484 to permit fitting 415C to clear bone probe 422. Stylet 420 is thus mounted pivotally to carrier assembly 430. Force applied to the handle 412 when placing a portal in the subject's bone by pushing on handle 412 is applied approximately axially along stylet 420, thereby causing stylet 420 to penetrate the subject's bone. During use to introduce a bone portal, stylet 420 is prevented from pivoting by its engagement in guide aperture 468 and/or additional supports.

Once bone portal 415A has been positioned within the subject's bone and stylet 420 has been withdrawn from guide aperture 468, force applied generally radially to handle 412 will cause stylet 420 to pivot relative to carrier assembly 430 and bone probe 422, thereby permitting fitting 415C to slide freely off the tip of the stylet 420. In some embodiments, stylet 420 is withdrawn from guide aperture 468 upon detachment of the rest of the introducer tool from base 414.

Alternative methods of pivotally mounting stylet 420 to carrier assembly 430 include mounting the stylet 420 in an elastomeric base, or mounting stylet 420 by way of a hinge, pivot pin, or the like which permits stylet 420 to pivot relative to carrier assembly 430.

Figure 26A:
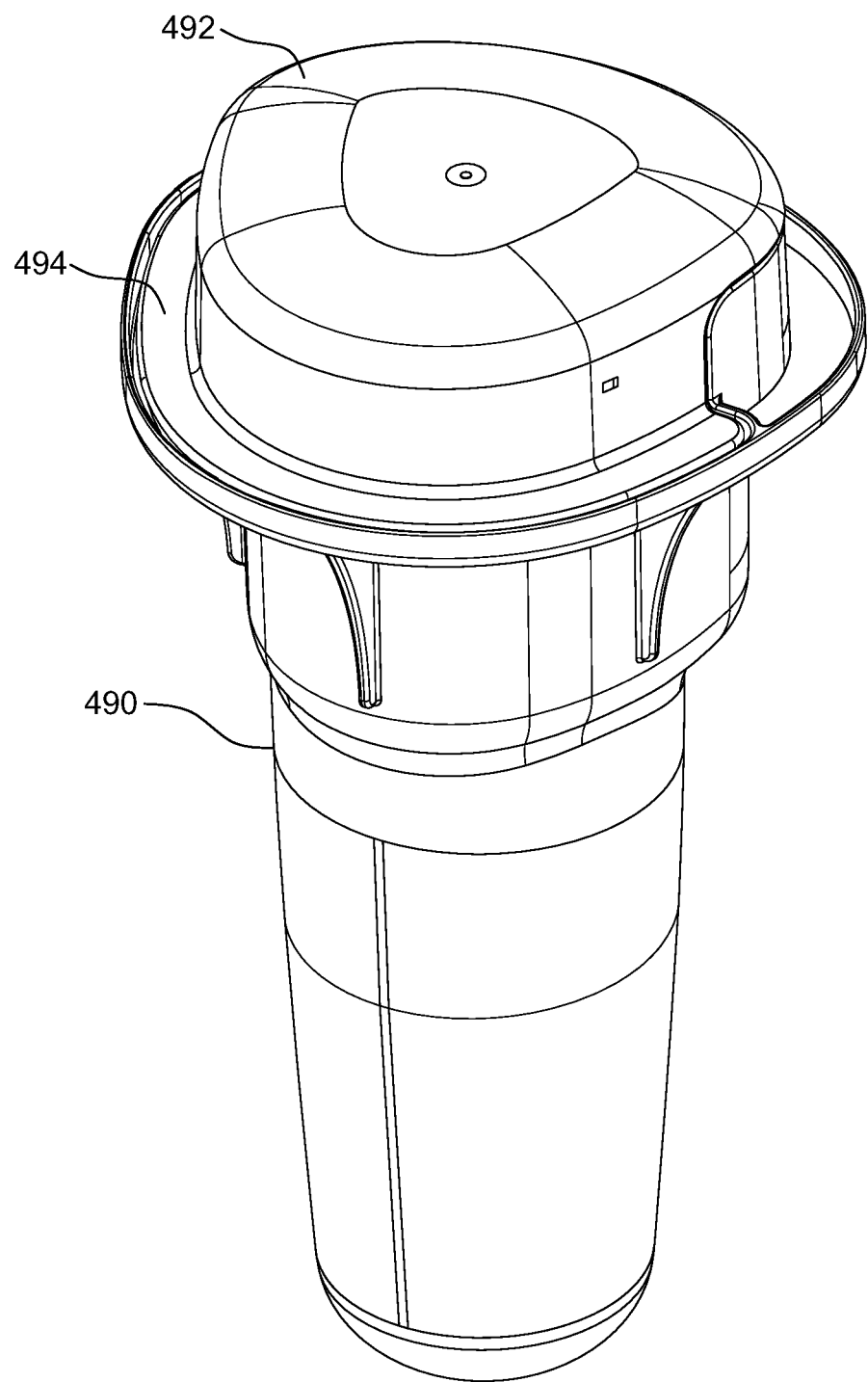
FIGS. 26A and 26B are respectively perspective and end views showing packaging for an introducer tool.
Figure 26B:
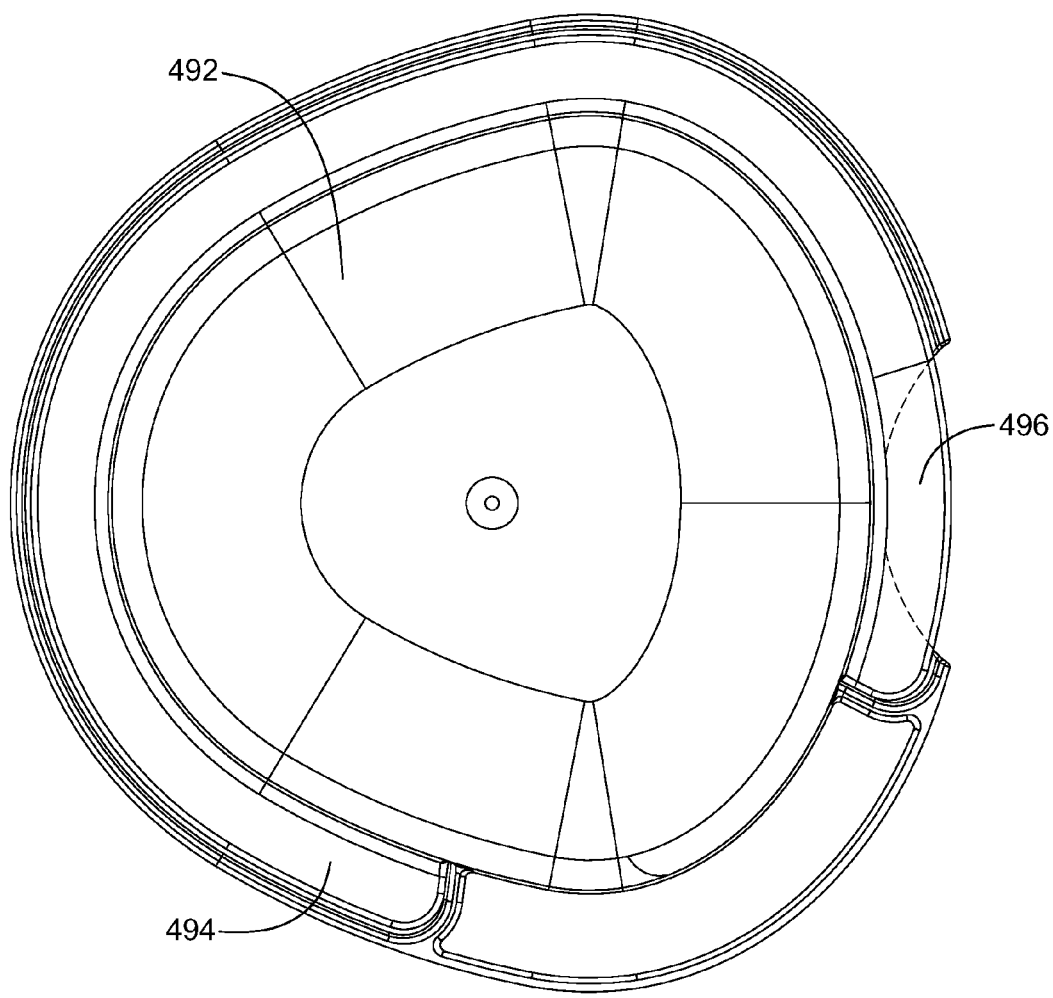
Figure 27:
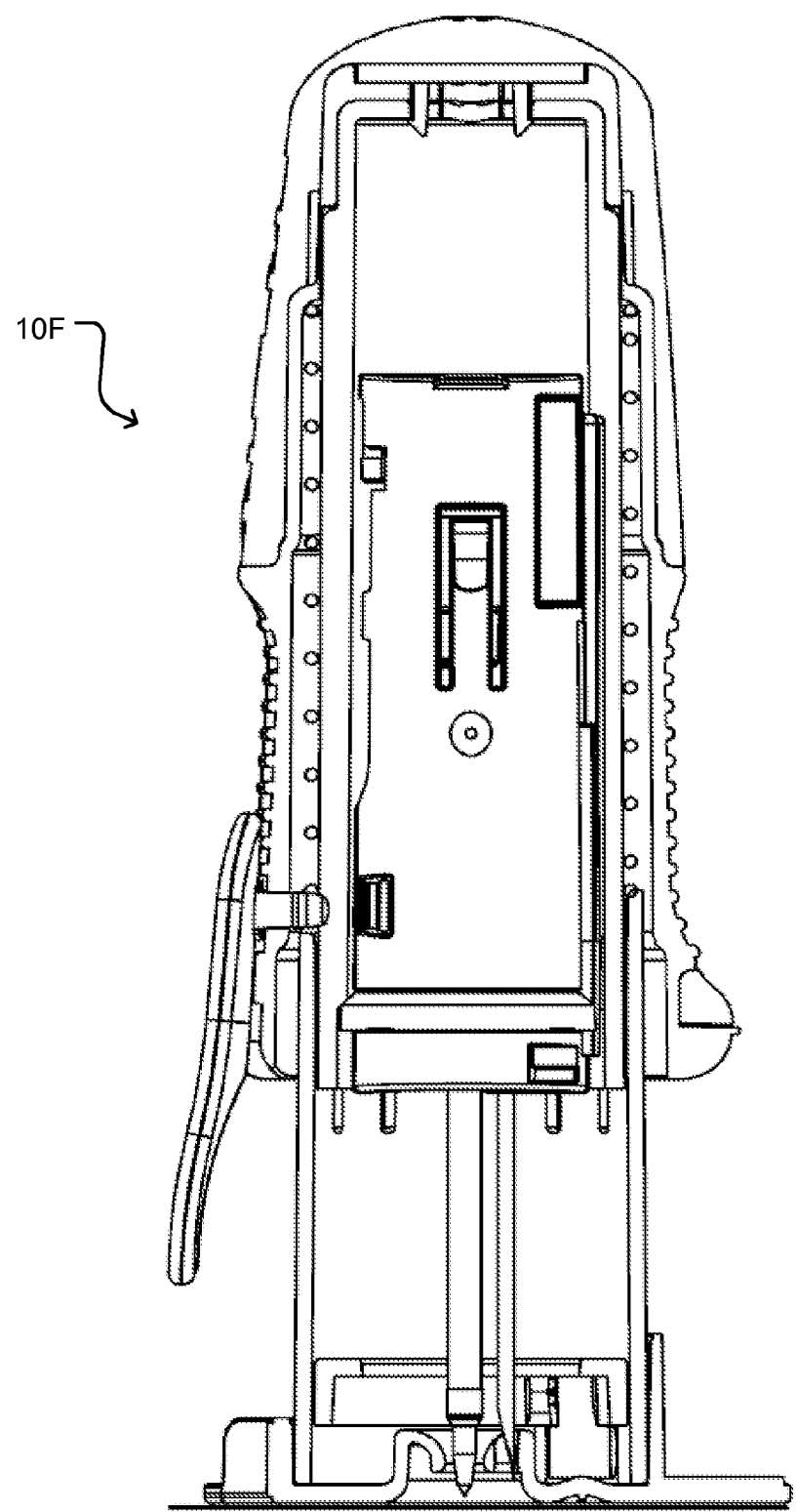
FIGS. 27, 28 and 29 are cut away views showing the introducer tool of FIG. 18A at various stages of deployment.
Figure 28:
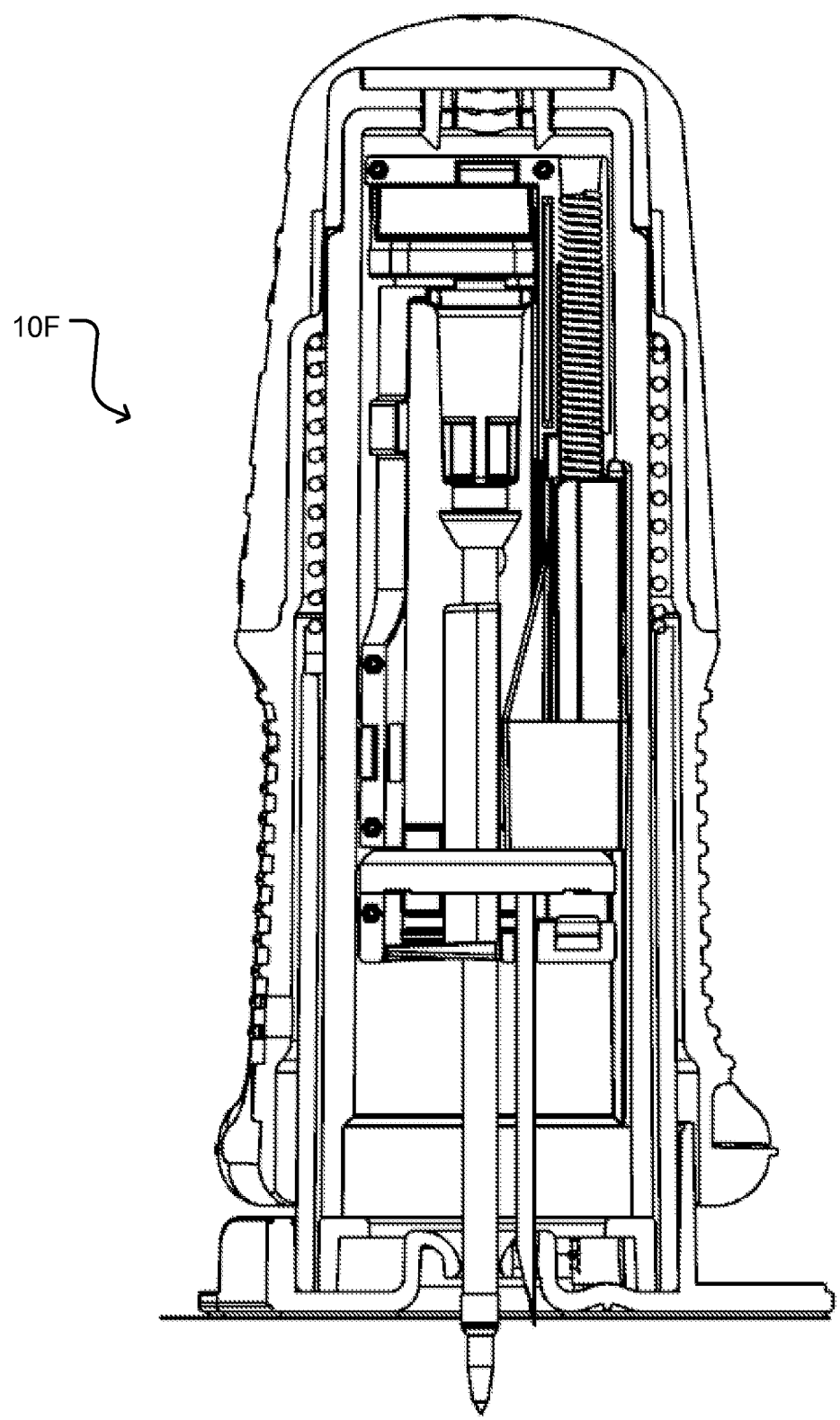
Figure 29:
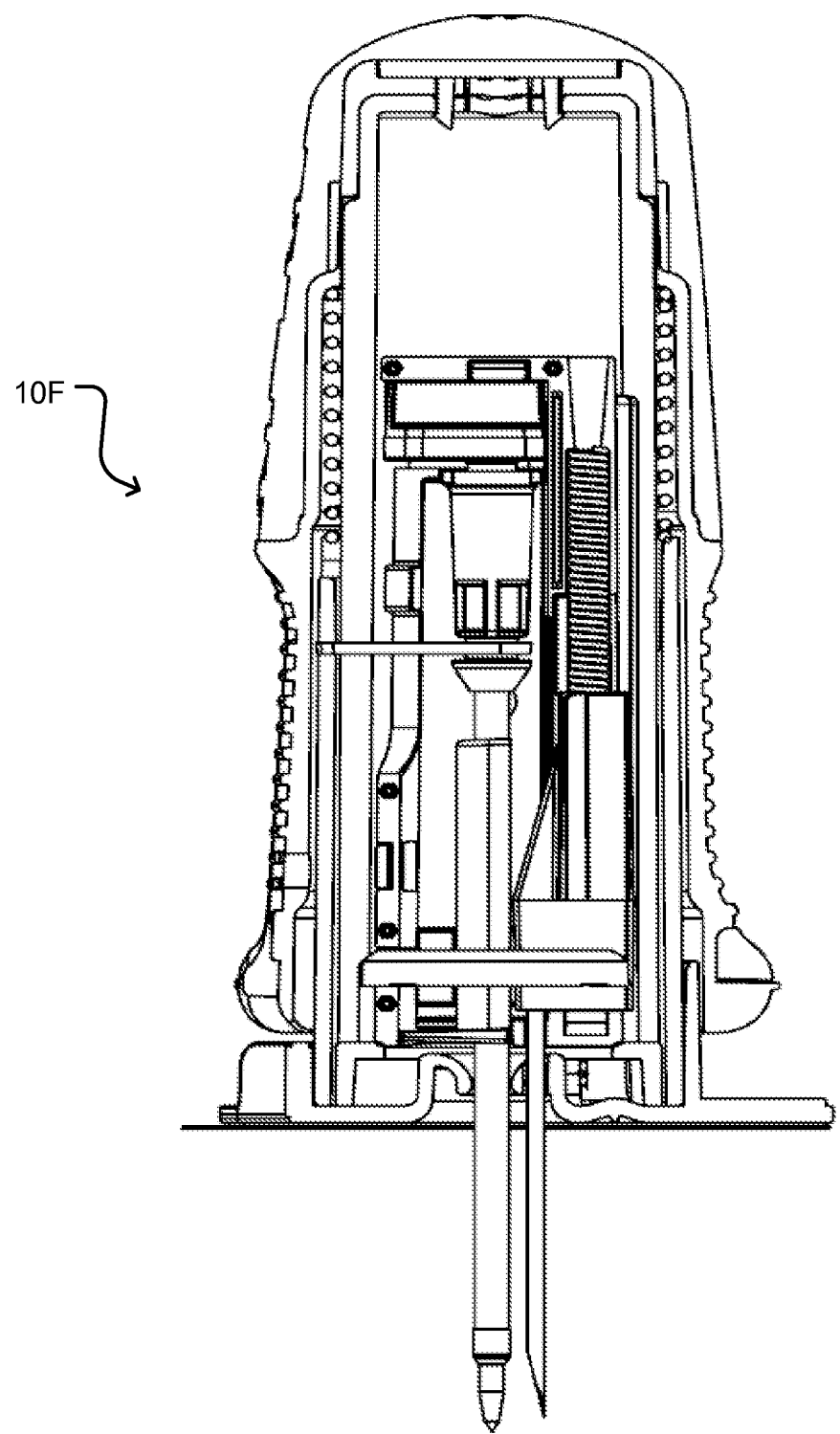

Introducer tool 10F or other introducer tools such as those, for example, that are described herein may be supplied in a sterile condition in sealed packaging. FIGS. 26A and 26B show packaging 490 that includes a removable lid portion 492. In some embodiments, lid portion 492 is adapted to be used as a cover for base 414 after a bone portal has been introduced into a subject. In such embodiments, lid portion 492 comprises a flange 494 carrying an adhesive (not shown) covered by a release sheet 496. After packaging 490 has been opened by removing lid 492, the user can remove release sheet 496. After the user has used introducer tool 10F to place a bone portal in a subject, the user may place lid portion 492 over base 414 and the projecting parts of infusion tube assembly 415 and secure the lid portion in place with the adhesive. This adds an extra layer of protection for the infusion site. Lid portion 492 may be transparent to permit viewing of the infusion site through lid portion 492. Lid portion 492 provides additional support to prevent infusion tube 415B from being crushed against the subject.

Packaging 490 may also include one or more ribs, Velcro™, loops, hooks, or hook and eyelet fasteners for securing introducer tool 10F in a medic's pack, for example.

Dual use packaging of the type described above is not limited to use with introducer tools for bone portals. Packaging comprising a plurality of parts, wherein at least one of the parts comprises a lid portion with an adhesive flange has application in other medical contexts where protection of a vulnerable or delicate working site is desired. For example, the packaging may be used for various types of catheters (e.g. peripheral venous, epidural), body electrodes, and the like.

In some embodiments, a detent or other suitable mechanism, as described above, may be provided to provide both tactile and/or auditory feedback to indicate full insertion of a bone portal.

While, in some applications, it is acceptable to treat the introducer tool as disposable, in other cases it may be desirable to make significant portions of the introducer tool reusable. In such cases, a disposable stylet may be provided in a form of a cartridge which can be inserted and received within the introducer tool. In such cases, the introducer tool may be made in such a manner that it can be readily cleaned and sterilized for re-use. The introducer tool may then be re-used upon the insertion of a new cartridge containing a new stylet and a new base.

In embodiments in which a force-limiting coupling is not provided, the bone stop on the portal may be made larger or an additional backup bone stop may be provided to help to ensure that overpenetration of the portal will not occur during insertion.

In some embodiments, absorbent material is provided on the top side of the base to assist in soaking up blood or other fluids that may be located near the insertion site. The adhesive layer and/or the absorbent material, if present, may incorporate anti-bacterial and/or anti-viral agents to help to avoid any infection.

In some embodiments, the tube which is connected to the portal has a diameter that is much greater than the diameter of the passage which extends through the bone-penetrating portion of the portal. Further, the bone penetrating portion of the portal is relatively short compared to the length of the tube. Thus, an infusion tube as described herein can provide much less restriction to the flow of fluids than prior needles or the like which have highly elongated narrow bores.

In some embodiments, the portal comprises a longitudinally-extending passage for conveying fluids into the bone. In such embodiments the method may comprise placing a stylet through the longitudinally-extending passage such that a tip of the stylet extends past a distal end of the portal and, after introduction of the portal into the bone, withdrawing the tip of the stylet. In some embodiments, a flexible tube is connected to the portal and the stylet extends through the flexible tube. In some embodiments the stylet comprises an offset point and the method comprises rotating the stylet while continuing to push on the portal.

Where a component (e.g. an assembly, device, spring, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

While a number of exemplary aspects and embodiments have been discussed above, those of skill in the art will recognize certain modifications, permutations, additions and sub-combinations thereof. All such modifications, permutations, additions and sub-combinations as are novel and inventive are included in the inventive concepts disclosed herein.

What is claimed is:

1. Apparatus for introducing a bone portal into a bone, the apparatus comprising:
    a stylet configured to support an infusion tube assembly comprising a bone portal;
    a handle drivingly coupled to the stylet by a release mechanism, the release mechanism comprising a bone probe that, in a first configuration, extends generally parallel to the stylet, the release mechanism operative to uncouple the driving coupling between the handle and the stylet upon axial motion of the bone probe relative to the handle;
    wherein the stylet and bone probe are movable apart from one another from the first configuration to a second configuration, wherein a spacing between the stylet and the bone probe in a direction transverse to the stylet is greater in the second configuration than in the first configuration.

2. Apparatus according to claim 1 comprising an infusion tube assembly removably supported on the stylet, the infusion tube assembly comprising a tube having a bone portal at a first end thereof and a fitting at another end thereof, the fitting extending transversely outward of the stylet for a distance greater than a spacing between the stylet and the bone probe when the bone probe is in the first configuration.

3. Apparatus according to claim 2 wherein the fitting comprises a Luer fitting.

4. Apparatus according to claim 1 wherein the stylet and bone probe are mounted to a carrier assembly that is received in a bore within the handle and the stylet is pivotally mounted to the carrier assembly.

5. Apparatus according to claim 1 wherein the stylet and bone probe are mounted to a carrier assembly that is received in a bore within the handle and the bone probe is pivotally mounted to the carrier assembly.

6. Apparatus according to claim 1 wherein the bone probe comprises a tip configured such that insertion of the tip into a subject results in a normal force on the tip having a component in a direction away from stylet.

7. Apparatus according to claim 6 wherein the tip has a facet, wherein the bone probe is oriented with the facet facing the stylet.

8. Apparatus according to claim 1 comprising a base coupled to the handle, the base comprising a first guide configured to maintain the stylet and bone probe in the first configuration.

9. Apparatus according to claim 8 wherein the first guide comprises an aperture in a raised portion of the base and the stylet passes through the aperture.

10. Apparatus according to claim 9 wherein:
the stylet and bone probe are mounted to a carrier assembly that is received in a bore within the handle; and
operation of the release mechanism releases the carrier assembly to move in a distal direction within the handle.

11. Apparatus according to claim 9 wherein the base comprises a second guide configured to guide the bone probe when the stylet and bone probe are in the first configuration.

12. Apparatus according to claim 9 wherein the base is releasably coupled to the handle.

13. Apparatus according to claim 12 wherein the base is coupled to the handle by a tubular shield that is telescopic with the handle and extends around the stylet and bone probe.

14. Apparatus according to claim 1 wherein the stylet and bone probe are mounted to a carrier assembly that is received in a bore within the handle wherein operation of the release mechanism releases the carrier assembly to move in a distal direction within the handle.

15. Apparatus according to claim 1 wherein an angle between a longitudinal axis of the stylet and a longitudinal axis of the bone probe is greater in the second configuration than in the first configuration.

16. Apparatus for introducing a bone portal into a subject, the apparatus comprising:
a handle;
a stylet and a probe mounted to a carrier assembly coupled to the handle, the stylet and probe extending proximally from the handle; and
a release mechanism operable by axial force on the probe to allow the carrier assembly to move distally into the handle;
wherein the stylet and probe are movable apart from one another in a direction transverse to a longitudinal axis of the stylet at least when the carrier assembly has been moved distally into the handle.

17. Apparatus according to claim 16 comprising a base apertured to receive ends of the stylet and probe wherein the stylet and probe are movable apart from one another when the end of at least one of the stylet and probe has been retracted clear of the base.

18. Apparatus according to claim 17 wherein the base is detachably coupled to a guide and the guide is telescopically coupled to the handle.

19. Apparatus according to claim 18 comprising an infusion tube assembly removably supported on the stylet, the infusion tube assembly comprising a tube having a bone portal at a first end thereof and a fitting at another end thereof, the fitting extending transversely outward of the stylet for a distance greater than a spacing between the stylet and the probe.

20. Apparatus according to claim 16 wherein the stylet and probe are coupled such that moving the stylet and probe apart from one another results in an increase in an angle between a longitudinal axis of the probe and the longitudinal axis of the stylet.

\* \* \* \* \*